US006500641B1

(12) United States Patent
Chen et al.

(10) Patent No.: US 6,500,641 B1
(45) Date of Patent: Dec. 31, 2002

(54) COMPOSITIONS AND METHODS FOR IDENTIFYING ANTIGENS WHICH ELICIT AN IMMUNE RESPONSE

(75) Inventors: Si-Yi Chen, Pearland; Zhaoyang You, Houston, both of TX (US)

(73) Assignee: Wake Forest University School of Medicine, Winston-Salem, NC (US)

( * ) Notice: Subject to any disclaimer, the term of this patent is extended or adjusted under 35 U.S.C. 154(b) by 0 days.

(21) Appl. No.: 09/566,420

(22) Filed: May 5, 2000

Related U.S. Application Data

(60) Provisional application No. 60/132,752, filed on May 6, 1999, and provisional application No. 60/132,750, filed on May 6, 1999.

(51) Int. Cl.[7] ............ C12P 21/06; C12P 21/08; C12Q 1/68; C07K 16/00; A61K 39/42

(52) U.S. Cl. .......... 435/69.1; 435/6; 530/387.3; 530/388.3; 424/159.1

(58) Field of Search ................. 435/6, 69.1; 530/387.3, 530/388.3; 424/159.1

(56) References Cited

U.S. PATENT DOCUMENTS

| | | | |
|---|---|---|---|
| 5,169,628 A | 12/1992 | Wathen | 424/89 |
| 5,580,563 A | 12/1996 | Tam | 424/197.11 |
| 5,587,455 A | 12/1996 | Berger et al. | 530/324 |
| 5,637,483 A | 6/1997 | Dranoff et al. | 424/93.21 |
| 5,679,647 A | 10/1997 | Carson et al. | 514/44 |
| 5,703,057 A | 12/1997 | Johnston et al. | 514/44 |
| 5,851,756 A | 12/1998 | Steinman et al. | 435/2 |
| 6,224,870 B1 | 5/2001 | Segal et al. | 424/184.1 |

FOREIGN PATENT DOCUMENTS

| | | |
|---|---|---|
| WO | 9408601 | 4/1994 |
| WO | WO 97/00321 | 1/1997 |
| WO | 9722349 | 6/1997 |
| WO | 9833523 | 8/1998 |
| WO | WO 94/21680 | 9/1999 |
| WO | 9947646 | 9/1999 |

OTHER PUBLICATIONS

Bennink & Yewdell, Recombinant Vaccinia Viruses as Vectors for Studying T Lymphocyte Specificity and Function, *Current Topics in Microbiology & Immunology* 163:154–84 (190).

Chattergoon et al., Specific Immune Induction Following DNA–Based Immunization Through In Vivo Transfection and Activation of Macrophages/Antigen–Presenting Cells, *J. Immunology* 160:5707–18 (1998).

Corr et al., Gene Vaccination With Naked Plasmid DNA: Mechanism of CTL Priming, *J. Experimental Med.* 184:1555–60 (1996).

(List continued on next page.)

*Primary Examiner*—Hankyel T. Park
(74) *Attorney, Agent, or Firm*—Morgan, Lewis & Bockius, LLP.

(57) ABSTRACT

This invention relates to an expression vector wherein said expression vector comprises a polynucleotide promoter sequence, a polynucleotide encoding a signal sequence, a polynucleotide encoding an antigen protein or peptide, a polynucleotide encoding a cell binding element, and a polynucleotide polyadenylation sequence all operatively linked. More particularly, it relates to the method of eliciting an immune response directed against an antigen in a mammal comprising the steps of introducing the expression vector into a cell, expressing the vector to produce an antigen under conditions wherein the antigen is secreted from the cell, endocytosing the secreted antigen into the cell, processing the antigen, and presenting fragments to a receptor to elicit a T-cell response. In addition, this invention relates to a vaccine and a method of use. The invention also relates to the method of identifying MHC-II restricted epitopes.

119 Claims, 34 Drawing Sheets

OTHER PUBLICATIONS

Eager et al., Murine Cell Lines Stably Expressing the Influenza Virus Hemagglutinin Gene Introduced by a Recombinant Retrovirus Vector Are Constitutive Targets for MHC Class I–and Class II–Restricted T Lymphocytes, *J. Immunology* 143:2328–35 (1989).

Germain, Antigen Processing and CD4+T Cell Depletion in AIDS, *Cell* 54:441–4 (1988).

Guyre et al., Increased Potency of Fc–Receptor–Targeted Antigens, *Cancer Immunology & Immunotherapy* 45:146–8 (1997).

Haddad et al., Differential Induction of Immunoglobulin G Subclasses by Immunization With DNA Vectors Containing or Lacking a Signal Sequence, *Immunology Letters* 61:201–4 (1998).

Jacobson et al., HLA Class II–Restricted Presentation of Cytoplasmic Measles Virus Antigens to Cytotoxic T Cells, *J. Virology* 63:1756–62 (1989).

Lekutis et al., HIV–1 env DNA Vaccine Administered to Rhesus Monkeys Elicits MHC Class II–Restricted CD4+T Helper Cells That Secrete IFN–$\gamma$ and TNF–$\alpha$, *J. Immunology* 158:4471–7 (1997).

Lombard–Platet et al., Invariant Chain Expression Similarly Controls Presentation of Endogenously Synthesized and Exogenous Antigens by MHC Class II Molecules, *Cellular Immunology* 148:60–70 (1993).

Polydefkis et al., Anchor Sequence–Dependent Endogenous Processing of Human Immunodeficiency Virus 1 Envelope Glycoprotein gp160 for CD4+T Cell Recognition, *J. Experimental Med.* 171:875–87 (1990).

Sanderson et al., Expression of Endogenous Peptide–Major Histocompatibility Complex Class II Complexes Derived From Invariant Chain–Antigen Fusion Proteins, *Proc. Natl. Acad. Sci.* USA 92:7217–21 (1995).

Syrengelas, Chen, & Levy, DNA Immunization Induces Protective Immunity Against B–Cell Lymphoma, *Nature Med.* 2:1038–41 (Sep. 1996).

Syrengelas & Levy, DNA Vaccination Against the Idiotype of a Murine B Cell Lymphoma: Mechanism of Tumor Protection, *J. Immunology* 162:4790–5 (1999).

Wu et al., Engineering an Intracellular Pathway for Major Histocompatability Complex Class II Presentation of Antigens, *Proc. Natl. Acad. Sci.* USA 92:11671–5 (1995).

IL-5 for cell-binding (HbeAg, Hepatitis B Virus)
LNC-IL5-HBeAg 
LNC-I

PET Cell-binding domain for HIV-1

LNC-PE-gp120   —| LTR | ΔNGFR | CMV | PE | gp120 | Fc | LTR |—

LNC-PE-gag    —| LTR | ΔNGFR | CMV | PE | gag | LTR |—

LNC-S-gag     —| LTR | ΔNGFR | CMV | S | gag | LTR |—

LNC-gag       —| LTR | ΔNGFR | CMV | gag | LTR |—

LNC-PE        —| LTR | ΔNGFR | CMV | PE | LTR |—

Figure 2C

SEQ. ID. NO. 19  M H G D T P T L H E Y M L D L Q P E T T D

L Y C Y E Q L S ⎢D S S E E E D E⎢ I D G P A G

Q A E P D R A H Y N I V T F C C K C D S T L

R L C V Q S T H V D I R T L E D L L M G T L

G I V C P I C S Q K P

FIGURE 17 pCMV-HBeAg-Fc pCMV-HBeAg pCMV-HBcAg

PCMV-Fc

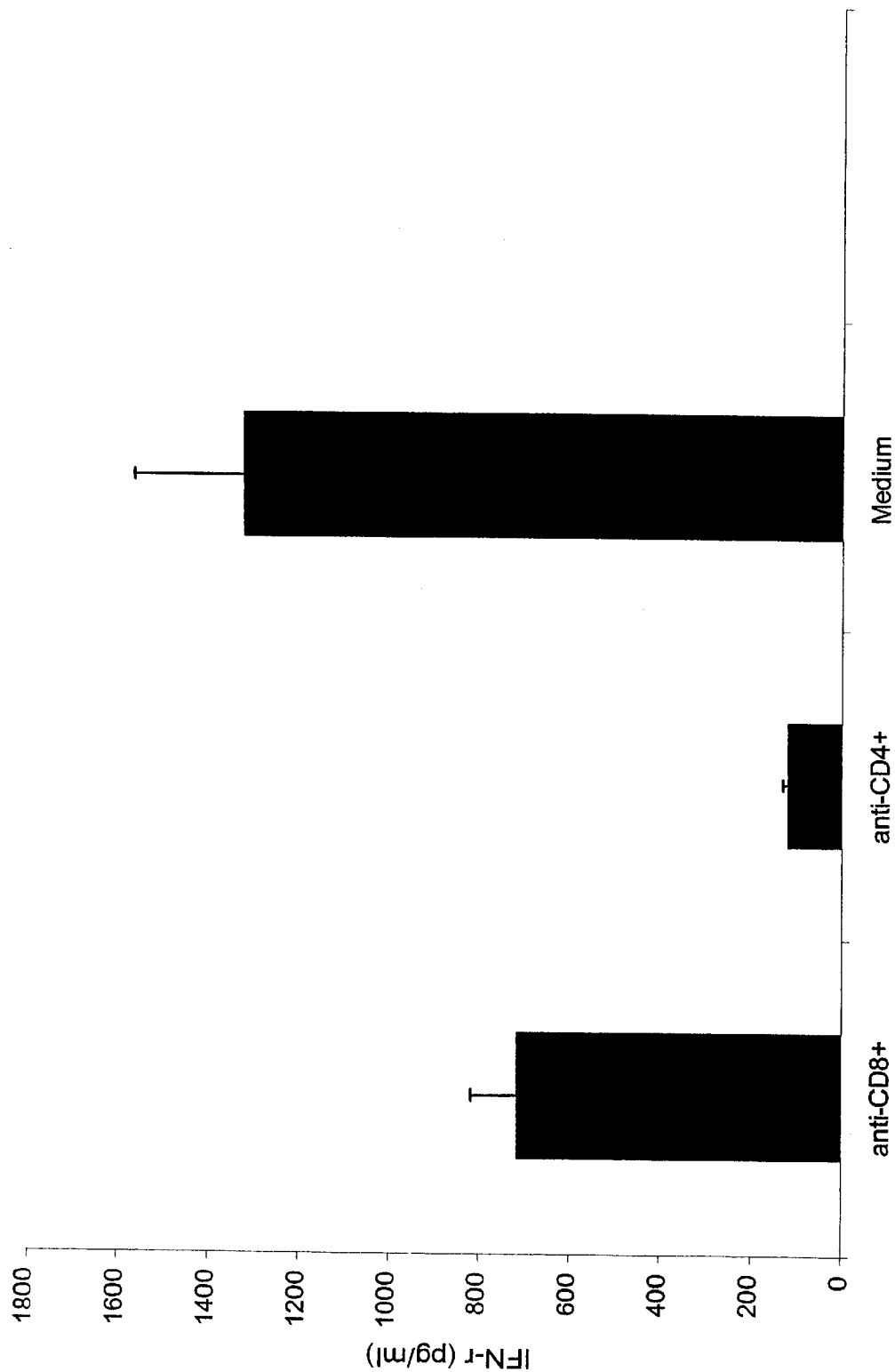

COMPOSITIONS AND METHODS FOR IDENTIFYING ANTIGENS WHICH ELICIT AN IMMUNE RESPONSE

This application claims priority to U.S. Provisional Application No. 60/132,752, filed May 6, 1999 and U.S. Provisional Application No. 60/132,750, filed May 6, 1999.

This invention was made using funds obtained from the U.S. Government (National Institutes of Health Grant No. RO1 A1419595-01) and the U.S. Government may therefore have certain rights in the invention.

FIELD OF THE INVENTION

This invention relates to an expression vector and its use to elicit a complete immune response in a mammal. More particularly it relates the processing of an endogenous antigen as an exogenous antigen for presentation on MHC-II. This invention also relates to a vaccine and its method of use to immunize a mammal.

BACKGROUND OF THE INVENTION

Inadequate antigen presentation in humans results in the failure of human immune system to control and clear many pathogenic infections and malignant cell growth. Successful therapeutic vaccines and immunotherapies for chronic infection and cancer rely on the development of new approaches for efficient antigen presentation to induce a vigorous immune. response which is capable of controlling and clearing the offensive antigens.

The ability of T cells to recognize an antigen is dependent on association of the antigen with either MHC Class I (MHC-I) or Class II (MCH-II) proteins. For example, cytotoxic T cells respond to an antigen in association with MHC-I proteins. Thus, a cytotoxic T cell that kills a virus-infected cell will not kill a cell infected with the same virus if the cell does not also express the appropriate MHC-I protein. Helper T cells recognize MHC-II proteins. Helper T cell activity depends in general on both the recognition of the antigen on antigen presenting cells and the presence on these cells of "self" MHC-II proteins. This requirement to recognize an antigen in association with a self-MHC protein is called MHC restriction. MHC-I proteins are found on the surface of virtually all nucleated cells. MHC-II proteins are found on the surface of certain cells including macrophages, B cells, and dendritic cells of the spleen and Langerhans cells of the skin.

A crucial step in mounting an immune response in mammals, is the activation of CD4+ helper T-cells that recognize major histocompatibility complexes (MHC)-II restricted exogenous antigens. These antigens are captured and processed in the cellular endosomal pathway in antigen presenting cells, such as dendritic cells (DCs) (Zajac et al., 1998; Bona et al., 1998; Kalams et al., 1998; Mellman et al., 1998; Banchereau et al., 1998). In the endosome and lysosome, the antigen is processed into small antigenic peptides that are presented onto the MHC-II in the Golgi compartment to form an antigen-MHC-II complex. This complex is expressed on the cell surface, which expression induces the activation of CD4+ T cells.

Other crucial events in the induction of an effective immune response in an animal involve the activation of CD8+ T-cells and B cells. CD8+ cells are activated when the desired protein is routed through the cell in such a manner so as to be presented on the cell surface as processed proteins, which are complexed with MHC-I antigens. B cells can interact with the antigen via their surface immunoglobulins (IgM and IgD) without the need for MHC proteins. However, the activation of the CD4+ T-cells stimulates all arms of the immune system. Upon activation, CD4+ T-cells (helper T cells) produce interleukins. These interleukins help activate the other arms of the immune system. For example, helper T cells produce interleukin-4 (IL-4) and interleukin-5 (IL-5), which help B cells produce antibodies; interleukin-2 (IL-2), which activates CD4+ and CD8+ T-cells; and gamma interferon, which activates macrophages.

Since helper T-cells that recognize MHC-II restricted antigens play a central role in the activation and clonal expansion of cytotoxic T-cells, macrophages, natural killer cells and B cells, the initial event of activating the helper T cells in response to an antigen is crucial for the induction of an effective immune response directed against that antigen. Attempts to stimulate helper T-cell activation using a sequence derived from the lysosomal transmembrane proteins have been reported (Wu, 1995). However, these attempts did not result in the induction of effective immune responses with respect to CD8+ T-cells and B cells in the mammals being tested.

Thus, there is a long felt need in the art for efficient and directed means of eliciting an immune response for the treatment of diseases in mammals. The present invention satisfies this need.

SUMMARY OF THE INVENTION

An embodiment of the present invention is an expression vector comprising a polynucleotide promoter sequence, a polynucleotide encoding a signal sequence, a polynucleotide encoding an antigen, a polynucleotide encoding a cell binding element, and a polynucleotide polyadenylation sequence all operatively linked.

In specific embodiments of the present invention, the polynucleotide promoter sequence is selected from the group consisting of a constitutive promoter, an inducible promoter and a tissue specific promoter.

In another specific embodiment of the present invention, the polynucleotide encoding a signal sequence is selected from the group consisting of a hepatitis B virus E antigen signal sequence, an immunoglobulin heavy chain leader sequence, and a cytokine leader sequence.

An embodiment of the present invention is an expression vector wherein the polynucleotide encoding an antigen comprises a polynucleotide sequence for at least one epitope, wherein said at least one epitope induces a B cell response in a mammal.

A further embodiment of the present invention is an expression vector wherein the polynucleotide encoding an antigen comprises a polynucleotide sequence for at least one epitope, wherein said at least one epitope induces a CD4+ T-cell response in a mammal.

Another embodiment of the present invention is an expression vector wherein the polynucleotide encoding an antigen comprises a polynucleotide sequence for at least one epitope, wherein said at least one epitope induces a CD8+ T-cell response in a mammal.

A specific embodiment of the present invention is an expression vector wherein the polynucleotide sequence encoding an antigen comprises a polynucleotide sequence for at least one epitope, wherein said at least one epitope induces a B cell response, a CD4+ T-cell response and a CD8+ T-cell response in a mammal into which said antigen is introduced.

A further specific embodiment of the present invention is an expression vector wherein the polynucleotide sequence encoding an antigen comprises a polynucleotide sequence for a plurality of epitopes, wherein said plurality of epitopes induces a B cell response, a CD4+ T-cell response and a CD8+ T-cell response in a mammal into which said antigen is introduced.

A further embodiment of the present invention is an expression vector wherein the polynucleotide encoding a cell binding element is a polynucleotide sequence of a ligand which binds to a cell surface receptor. In specific embodiments, the cell binding element sequence is selected from the group consisting of polynucleotide sequences which encode a Fc fragment, a toxin cell binding domain, a cytokine, a small peptide and an antibody. In specific embodiments, the polynucleotide encoding a cell binding element is a homologous polynucleotide sequence or a heterologous polynucleotide sequence.

An additional embodiment of the present invention is a transformed cell comprising an expression vector wherein said expression vector comprises a polynucleotide promoter sequence, a polynucleotide encoding a signal sequence, a polynucleotide encoding an antigen, a polynucleotide encoding a cell binding element, and a polynucleotide polyadenylation sequence all operatively linked.

Another specific embodiment of the present invention is a fusion protein wherein the fusion protein comprises a signal sequence, an antigen and a cell binding element. In specific embodiments, antigen presenting cells have been transduced with the fusion protein in vitro. In further embodiments, the fusion protein is administered directly to a mammal.

A specific embodiment of the present invention is a vaccine comprising an expression vector wherein said expression vector comprises a polynucleotide promoter sequence, a polynucleotide encoding a signal sequence, a polynucleotide encoding an antigen, a polynucleotide encoding a cell binding element, and a polynucleotide polyadenylation sequence all operatively linked. In specific embodiments, a vaccine comprises antigen presenting cells, wherein said antigen presenting cells are transduced in vitro with the expression vector. In further embodiments, a vaccine comprises antigen presenting cells, wherein said antigen presenting cells are transduced in vitro with the fusion protein.

Another specific embodiment of the present invention is an expression vector comprising at least a polynucleotide encoding a signal sequence, a polynucleotide encoding an antigen and a polynucleotide encoding a cell binding element.

A further embodiment of the present invention is a method to elicit an immune response directed against an antigen, comprising the steps of: introducing an expression vector into a cell, wherein said expression vector comprises a polynucleotide promoter sequence, a polynucleotide encoding a signal sequence, a polynucleotide encoding an antigen, a polynucleotide encoding a cell binding element, and a polynucleotide polyadenylation sequence, all operatively linked; and expressing said vector to produce an antigen under conditions wherein said antigen is secreted from the cell; said secreted antigen is endocytosed into the cell; said endocytosed antigen is processed inside the cell; and said processed antigen is presented to a cell surface protein, to elicit a T-cell mediated immune response. In specific embodiments, the antigen is secreted by a first cell and internalized by a second cell wherein the first and second cells are antigen presenting cells. In further embodiments, the first cells is a non-antigen presenting cell and the second cell is an antigen presenting cell.

Another specific embodiment of the present invention is a method to identify a polynucleotide sequence which encodes at least one MHC-II restricted epitope that is capable of activating CD4+ helper T-cells, said method comprising the steps of: introducing an expression vector into an antigen presenting cell to produce a transduced antigen presenting cell, wherein said expression vector comprises a polynucleotide promoter sequence, a polynucleotide encoding a signal sequence, a polynucleotide encoding a test polypeptide, a polynucleotide encoding a cell binding element, and a polynucleotide polyadenylation sequence, all operatively linked; contacting said transduced antigen presenting cell with naive or primed T-cells; and assessing whether any naive T-cells or primed T-cells are activated upon contact with said transduced antigen presenting cell, wherein activation of any of said T-cells indicates that the polynucleotide encoding the test polypeptide is a gene or fragment thereof capable of activating CD4+ helper T-cells. In specific embodiments, the polynucleotide encoding a test polypeptide is selected from the group of cDNA libraries consisting of viral genomes, bacterial genomes, parasitic genomes and human genomes.

Another embodiment of the present invention is a method to identify a polynucleotide sequence which encodes at least one MHC-II restricted epitope that is capable of eliciting an immune response in vivo, said method comprising the steps of: introducing an expression vector into antigen presenting cells to produce transduced antigen presenting cells, wherein said expression vector comprises a polynucleotide promoter sequence, a polynucleotide encoding a signal sequence, a polynucleotide encoding a test polypeptide, a polynucleotide encoding a cell binding element, and a polynucleotide polyadenylation sequence, all operatively linked; administering said transduced antigen presenting cells to a mammal via a parenteral route; collecting T-cells from splenocytes and co-culturing with dendritic cells; and assessing activation of T-cells, wherein said activation of T-cells indicate that the polynucleotide encoding the test polypeptide is a gene or fragment thereof capable of activating CD4+ helper T-cells. In specific embodiments, the polynucleotide encoding a test polypeptide is selected from the group of cDNA libraries consisting of viral genomes, bacterial genomes, parasitic genomes and human genomes.

A specific embodiment of the present invention is a method to identify a polynucleotide sequence which encodes at least one MHC-II restricted epitope that is capable of eliciting an immune response in vivo, said method comprising the steps of: administering to a mammal via parenteral route an expression vector, wherein said expression vector comprises a polynucleotide promoter sequence, a polynucleotide encoding a signal sequence, a polynucleotide encoding a test polypeptide, a polynucleotide encoding a cell binding element, and a polynucleotide polyadenylation sequence, all operatively linked; administering said transduced antigen presenting cells to a mammal via a parenteral route; collecting T-cells from splenocytes and co-culturing with dendritic cells; and assessing activation of T-cells, wherein said activation of T-cells indicate that the polynucleotide encoding the test polypeptide is a gene or fragment thereof capable of activating CD4+ helper T-cells. In specific embodiments, the polynucleotide encoding a test polypeptide is selected from the group of cDNA libraries consisting of viral genomes, bacterial genomes, parasitic genomes and human genomes.

A specific embodiment of the present invention is a method of treating cancer comprising the steps of identifying a test polypeptide which encodes at least one MHC-II restricted epitope, wherein said polypeptide is identified under the conditions of transducing antigen presenting cells with an expression vector into antigen presenting cells to produce transduced antigen presenting cells, wherein said expression vector comprises a polynucleotide promoter sequence, a polynucleotide encoding a signal sequence, a polynucleotide encoding a test polypeptide, a polynucleotide encoding a cell binding element, and a polynucleotide polyadenylation sequence, all operatively linked and assessing activation of T-cells, wherein said activation of T-cells indicate that the polynucleotide encoding the test polypeptide is a gene or fragment thereof capable of activating CD4+ helper T-cells; and administering antigen presenting cells to a mammal via a parenteral route, wherein said antigen presenting cells are transduced with the test polypeptide.

Another specific embodiment of the present invention is a method of treating cancer comprising the steps of identifying a test polypeptide which encodes at least one MHC-II restricted epitope, wherein said polypeptide is identified under the conditions of transducing antigen presenting cells with an expression vector into antigen presenting cells to produce transduced antigen presenting cells, wherein said expression vector comprises a polynucleotide promoter sequence, a polynucleotide encoding a signal sequence, a polynucleotide encoding a test polypeptide, a polynucleotide encoding a cell binding element, and a polynucleotide polyadenylation sequence, all operatively linked and assessing activation of T-cells, wherein said activation of T-cells indicate that the polynucleotide encoding the test polypeptide is a gene or fragment thereof capable of activating CD4+ helper T-cells; and administering to a mammal via a parenteral route an expression vector, wherein said expression vector comprises at least the polynucleotide encoding the test polypeptide and a polynucleotide encoding a cell binding element said antigen presenting cells are transduced with the test polypeptide.

A further specific embodiment of the present invention is a method of treating a viral infection comprising the steps of identifying a test polypeptide which encodes at least one MHC-II restricted epitope, wherein said polypeptide is identified under the conditions of transducing antigen presenting cells with an expression vector into antigen presenting cells to produce transduced antigen presenting cells, wherein said expression vector comprises a polynucleotide promoter sequence, a polynucleotide encoding a signal sequence, a polynucleotide encoding a test polypeptide, a polynucleotide encoding a cell binding element, and a polynucleotide polyadenylation sequence, all operatively linked and assessing activation of T-cells, wherein said activation of T-cells indicate that the polynucleotide encoding the test polypeptide is a gene or fragment thereof capable of activating CD4+ helper T-cells; and administering antigen presenting cells to a mammal via a parenteral route, wherein said antigen presenting cells are transduced with the test polypeptide.

Another embodiment of the present invention is a method of treating a viral infection comprising the steps of identifying a test polypeptide which encodes at least one MHC-II restricted epitope, wherein said polypeptide is identified under the conditions of transducing antigen presenting cells with an expression vector into antigen presenting cells to produce transduced antigen presenting cells, wherein said expression vector comprises a polynucleotide promoter sequence, a polynucleotide encoding a signal sequence, a polynucleotide encoding a test polypeptide, a polynucleotide encoding a cell binding element, and a polynucleotide polyadenylation sequence, all operatively linked and assessing activation of T-cells, wherein said activation of T-cells indicate that the polynucleotide encoding the test polypeptide is a gene or fragment thereof capable of activating CD4+ helper T-cells; and administering to a mammal via a parenteral route an expression vector, wherein said expression vector comprises at least the polynucleotide encoding the test polypeptide and a polynucleotide encoding a cell binding element said antigen presenting cells are transduced with the test polypeptide.

Another embodiment of the present invention is a method of treating an autoimmune disease comprising the steps of identifying a test polypeptide which encodes at least one MHC-II restricted epitope, wherein said polypeptide is identified under the conditions of transducing antigen presenting cells with an expression vector into antigen presenting cells to produce transduced antigen presenting cells, wherein said expression vector comprises a polynucleotide promoter sequence, a polynucleotide encoding a signal sequence, a polynucleotide encoding a test polypeptide, a polynucleotide encoding a cell binding element, and a polynucleotide polyadenylation sequence, all operatively linked and assessing activation of T-cells, wherein said activation of T-cells indicate that the polynucleotide encoding the test polypeptide is a gene or fragment thereof capable of activating CD4+ helper T-cells; and administering antigen presenting cells to a mammal via a parenteral route, wherein said antigen presenting cells are transduced with the test polypeptide.

A specific embodiment of the present invention is a method of treating an autoimmune disease comprising the steps of identifying a test polypeptide which encodes at least one MHC-II restricted epitope, wherein said polypeptide is identified under the conditions of transducing antigen presenting cells with an expression vector into antigen presenting cells to produce transduced antigen presenting cells, wherein said expression vector comprises a polynucleotide promoter sequence, a polynucleotide encoding a signal sequence, a polynucleotide encoding a test polypeptide, a polynucleotide encoding a cell binding element, and a polynucleotide polyadenylation sequence, all operatively linked and assessing activation of T-cells, wherein said activation of T-cells indicate that the polynucleotide encoding the test polypeptide is a gene or fragment thereof capable of activating CD4+ helper T-cells; and administering to a mammal via a parenteral route an expression vector, wherein said expression vector comprises at least the polynucleotide encoding the test polypeptide and a polynucleotide encoding a cell binding element said antigen presenting cells are transduced with the test polypeptide.

A further embodiment of the present invention is a method of producing a vaccine to immunize a mammal comprising the steps of: transducing antigen presenting cell by introducing an expression vector into a cell, wherein said expression vector comprises a polynucleotide promoter sequence, a polynucleotide encoding a signal sequence, a polynucleotide encoding an antigen, a polynucleotide encoding a cell binding element, and a polynucleotide polyadenylation sequence, all operatively linked; and expressing said vector to produce an antigen under conditions wherein said antigen is secreted from the cell. In specific embodiments, antigen presenting cells are transduced with the antigen in vitro or ex vivo prior to administering the antigen presenting cells to the mammal.

Another specific embodiment of the present invention is a method of inducing an immune response comprising the steps of co-administering to a mammal a cytokine expression vector and a retrogen expression vector, wherein the retrogen expression vector comprises a polynucleotide promoter sequence, a polynucleotide encoding a signal sequence, a polynucleotide encoding an antigen, a polynucleotide encoding a cell binding element, and a polynucleotide polyadenylation sequence all operatively linked.

A further embodiment of the present invention is a method of inducing an immune response comprising the steps of co-administering to a mammal one expression vector, wherein said expression vector comprises a polynucleotide sequence encoding a cytokine protein and a polynucleotide sequence encoding a fusion protein under transcriptional control of one promoter, wherein said fusion protein comprises an antigen and a cell binding element. In specific embodiments, the polynucleotide sequence encoding the cytokine protein and the polynucleotide sequence encoding the fusion protein are under separate transcriptional control, and wherein the polynucleotide sequence encoding the cytokine protein and the polynucleotide sequence encoding the fusion protein are in tandem in the one expression vector.

Another embodiment of the present invention is a method of inducing an immune response comprising the steps of co-administering to a mammal two different retrogen expression vectors, wherein a first retrogen expression vector comprises a polynucleotide promoter sequence, a polynucleotide encoding a signal sequence, a polynucleotide encoding a first antigen, a polynucleotide encoding a cell binding element, and a polynucleotide polyadenylation sequence all operatively linked; and a second retrogen expression vector comprises a polynucleotide promoter sequence, a polynucleotide encoding a signal sequence, a polynucleotide encoding a second antigen, a polynucleotide encoding a cell binding element, and a polynucleotide polyadenylation sequence all operatively.

Another specific embodiment of the present invention is a method of inducing an immune response comprising the steps of administering to a mammal one expression vector, wherein said expression vector comprises a polynucleotide sequence encoding a first fusion protein and a polynucleotide sequence encoding a second fusion protein under transcriptional control of one promoter, wherein said first fusion protein comprises a first antigen and a first cell binding element and said second fusion protein comprises a second antigen and a first cell binding element. In specific embodiments, the first and second antigens are different antigens and the cell binding elements is a Fc fragment. In further embodiments, the first and second antigens are different antigens and the first and second cell binding elements are different cell binding elements. An additional embodiment includes that the polynucleotide sequence encoding the first fusion protein and the polynucleotide sequence encoding the second fusion protein are under separate transcriptional control, and wherein the polynucleotide sequence encoding the first fusion protein and the polynucleotide sequence encoding the second fusion protein are in tandem in one expression vector.

A specific embodiment of the present invention is a method of simultaneously inducing both CD4+ and CD8+ T-cells comprising the steps of administering a fusion protein wherein the protein comprises both a MHC-I and MHC-II epitope fused to a cell binding element.

A further embodiment of the present invention is a method of producing a fusion protein comprising the steps of introducing an expression vector into a cell, wherein said expression vector comprises a polynucleotide promoter sequence, a polynucleotide encoding a signal sequence, a polynucleotide encoding an antigen, a polynucleotide encoding a cell binding element, and a polynucleotide polyadenylation sequence, all operatively linked and expressing said vector to produce a fusion protein under conditions wherein said fusion protein is secreted from the cell. In specific embodiments, antigen presenting cells are transduced with the fusion protein in vitro.

A specific embodiment of the present invention is a method of secreting an intracellular protein comprising the steps of introducing an expression vector into a cell, wherein said expression vector comprises a polynucleotide promoter sequence, a polynucleotide encoding a signal sequence, a polynucleotide encoding an intracellular protein, a polynucleotide encoding a cell binding element, and a polynucleotide polyadenylation sequence, all operatively linked and expressing said vector to produce a fusion protein under conditions wherein said fusion protein is secreted from the cell. More specifically, the polynucleotide sequence encoding the intracellular protein is truncated or mutated to increase efficiency of secretion.

Another specific embodiment of the present invention is a method of secreting a membrane protein comprising the steps of introducing an expression vector into a cell, wherein said expression vector comprises a polynucleotide promoter sequence, a polynucleotide encoding a signal sequence, a polynucleotide encoding a membrane protein, a polynucleotide encoding a cell binding element, and a polynucleotide polyadenylation sequence, all operatively linked and expressing said vector to produce a fusion protein under conditions wherein said fusion protein is secreted from the cell. More specifically, the polynucleotide sequence encoding the membrane protein is truncated or mutated to increase efficiency of secretion.

BRIEF DESCRIPTION OF THE DRAWINGS

FIG. 1A and FIG. 1B are diagrams representing the retrogen strategy of the invention. The retrogen of the invention is produced in a cell, for example, a muscle cell (FIG. 1A), and is then taken up by an antigen presenting cell (FIG. 1B). The retrogen is processed in the antigen presenting cell and is expressed thereon as a MHC-I or a MHC-II complex, or presented to B cell receptors as shown in the FIG. 1A and FIG. 1B. MHC-I presentation of the retrogen results in the activation of cytotoxic CD8+ T-cells and MHC-II presentation of the retrogen results in the activation of CD4+ T-cells.

FIG. 2A, FIG. 2B and FIG. 2C are a series of schematic representations of the expression vectors. FIG. 2A illustrates a vector comprising HBeAg (secretory), HBcAg (cytosolic), or the Fc fragment with a signal sequence (secretory) constructed by generating a fusion gene as shown in the diagram, and cloning the gene into the retroviral vector (LNC-NGFR) or the expression vector pRc/CMV. FIG. 2B and FIG. 2C illustrate additional vectors that were constructed.

FIG. 3 is an image of a Western blot depicting expression and secretion of the HBe-retrogen. COS cells were transfected with various expression vectors. The culture medium (M) and cell lysates (C) were then precipitated with an anti-IgG or anti-HbeAg antibody and analyzed by SDS-PAGE.

FIG. 4A, FIG. 4B and FIG. 4C are a series of graphs depicting transduction and expression of retrogen in dendritic cells. Murine bone marrow cells were transduced with various recombinant retroviral vectors; the cells were matured into dendritic cells in the presence of GM-CSF, TNF, and IL-4 and stained with the anti-NGFR. They are measured by a flow cytometric assay. FIG. 4A shows the untransduced dendritic cells. FIG. 4B shows the transduced dendritic cells. FIG. 4C is a negative control.

FIG. 5A, FIG. 5B, FIG. 5C, FIG. 5D and FIG. 5E are a series of graphs depicting the presence of surface markers (MHC-I, MHC-II, co-stimulation, and adhesion molecules (CD11C, CD54, CD80 and CD86)) on dendritic cells as determined by flow cytometric assays. FIG. 5A shows the presence of CD11C surface marker. FIG. 5B shows the presence of CD54 surface marker. FIG. 5C shows the presence of CD80 surface marker. FIG. 5D shows the presence of CD86 surface marker. And FIG. 5E shows the presence of MHC-II.

FIG. 6A and FIG. 6B illustrate two bar graphs depicting in vitro activation of naive CD4+ T-cells by retrogen-transduced dendritic cells. FIG. 6A shows levels of GM-CSF in co-culture. FIG. 6D shows the levels of IFN-γ in the co-culture medium.

FIG. 7A and FIG. 7B illustrate the MHC-II-dependent activation. FIG. 7A shows the cytokine concentration (IFN-γ) from cells obtained from MHC-II-knockout (KO) or wild-type (WT) C57BL/6 mice transduced with the HBe-retrogen and co-cultured and naive CD4+ T-cells from wild type mice. FIG. 7B shows the GM-CSF cytokine concentration.

FIG. 8 shows antibody responses in the sera of immunized mice.

FIG. 9A, FIG. 9B, FIG. 9C, FIG. 9D, FIG. 9E and FIG. 9F show the construction and expression of s-MAGE-3-Fc fusion proteins. FIG. 9A shows the schematic representation of recombinant retroviral vectors. (S: the signal sequence. IRES: Internal ribosome entry site sequence.) FIG. 9B shows the expression of different constructs in dendritic cells as determined by Western blot analysis stained with the mouse anti-MAGE-3 and an anti-mouse IgG HRP conjugate. FIG. 9C shows the protein band intensity of the Western blot of FIG. 9B analyzed by a PhosphorImager (Molecular Dynamics) with an Image-Quant software. FIG. 9D, FIG. 9E and FIG. 9F illustrate the flow cytometric analysis of transduced dendritic cells transduced with each construct and stained for MHC-II (FIG. 9E) (M5/114.15.2), CD40 (FIG. 9D) (HM40-3), and CD86/B7.2 (FIG. 9F) (GL1) (PharMingen).

FIG. 10A, FIG. 10B, FIG. 10C and FIG. 10D show the in vivo induction of CD4+ Th1 responses of mice immunized with dendritic cells transduced with different vectors in the media after co-culture of CD4+ T-cells. FIG. 10A shows the concentrations of IFN-γ. FIG. 10B shows the concentrations of IL-2. FIG. 10C shows the concentrations of TNF-α. FIG. 10D shows the concentrations of IL-4.

FIG. 11A and FIG. 11B show the IFN-γ levels in CD4+ T-cells isolated from s-MAGE-3-Fc-dendritic cells immunized mice co-cultured with s-MAGE-3-Fc-dendritic cells in the presence or absence of anti-CD4 or anti-CD8 antibodies (FIG. 11A), or co-cultured with HBcAg transduced dendritic cells (FIG. 11B).

FIG. 12A, FIG. 12B, FIG. 12C and FIG. 12D show the cytokine levels in CD4+ T-cells isolated from pooled splenocytes of mice immunized with dendritic cells co-cultured with dendritic cells isolated from draining lymph nodes (LN) of the same immunized mice at a ratio of 1000:1. FIG. 12A shows the concentrations of IFN-γ. FIG. 12B shows the concentrations of IL-2. FIG. 12C shows the concentrations of TNF-α. FIG. 12D shows the concentrations of IL-4.

Figure 16A:
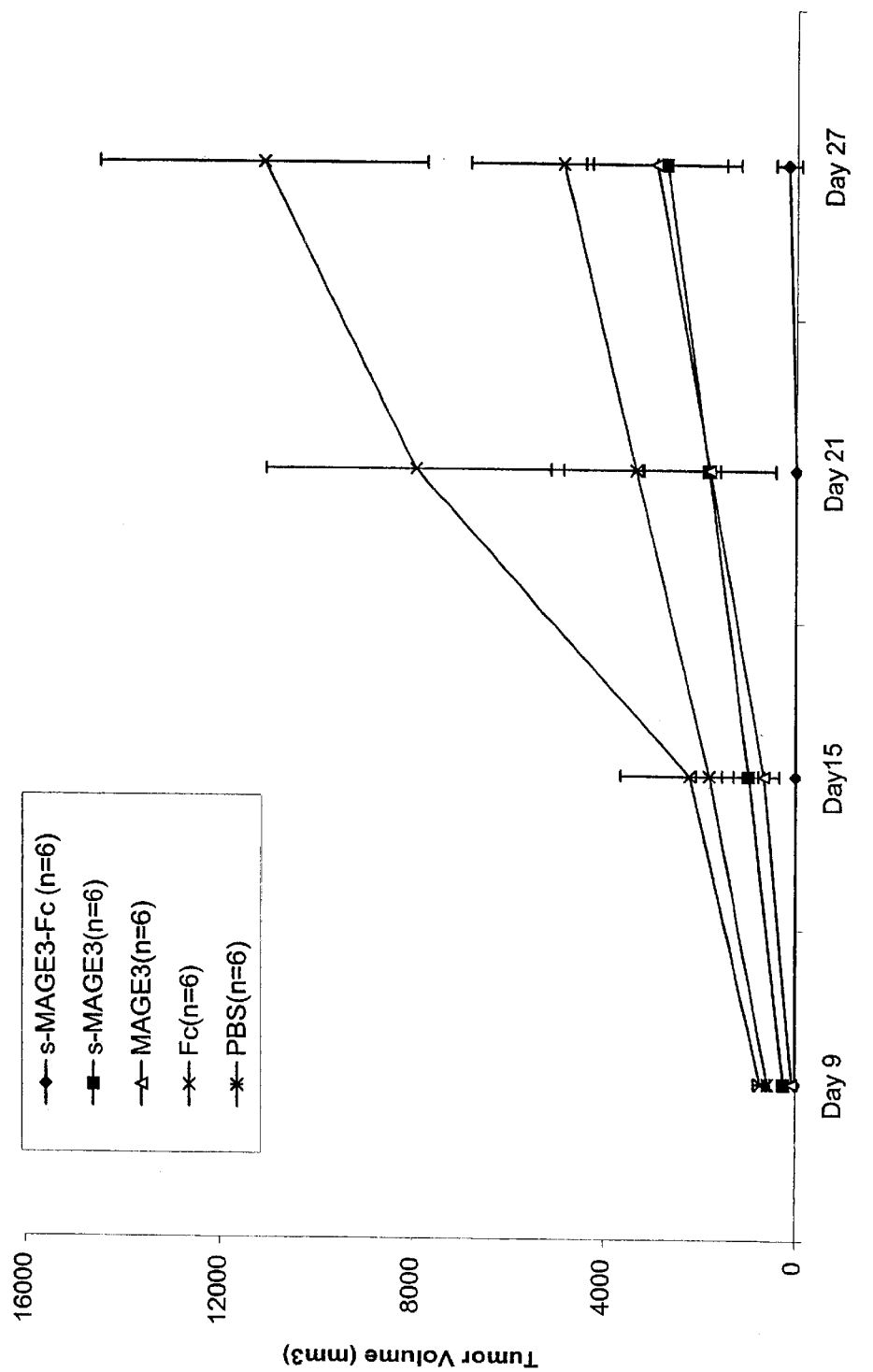
Figure 16B:
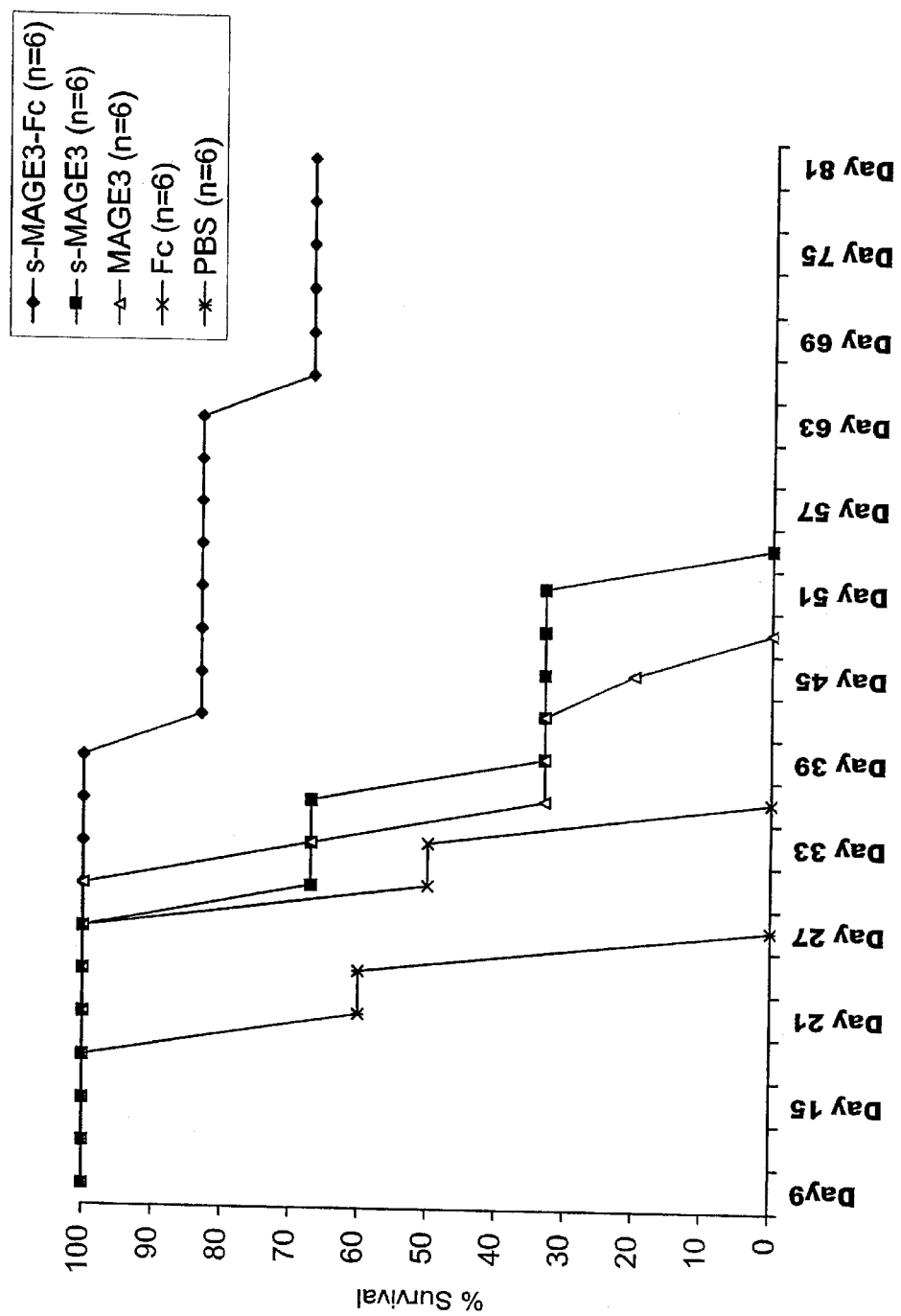

FIG. 16A and FIG. 16B show the antitumor immunity of mice that were immunized by i.v. injection with 1×10$^5$ dendritic cells transduced with different constructs before inoculated intradermally inoculated EL4-MAGE-3 tumor cells. FIG. 16A shows the tumor volumes. FIG. 16B shows the percentage of surviving mice in each group.

FIG. 17 illustrates the charged amino acid residues of HPV 16E7, which were deleted to stabilize the protein and facilitate secretion.

Figure 18:
Figure 18:
Figure 18:
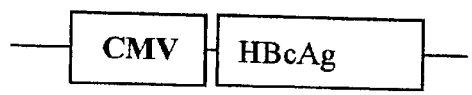
Figure 18:
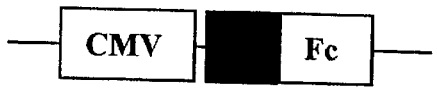

FIG. 18 illustrates a schematic representation of expression vectors. The HBe-Fc fusion gene, HBcAg (cytosolic) gene, HBeAg (secretory) gene, or Fc cDNA fragment with a signal sequence (secretory) was cloned into the pRc/CMV vector under the CMV promoter control, respectively. The black square represents the signal sequence.

Figure 19A:
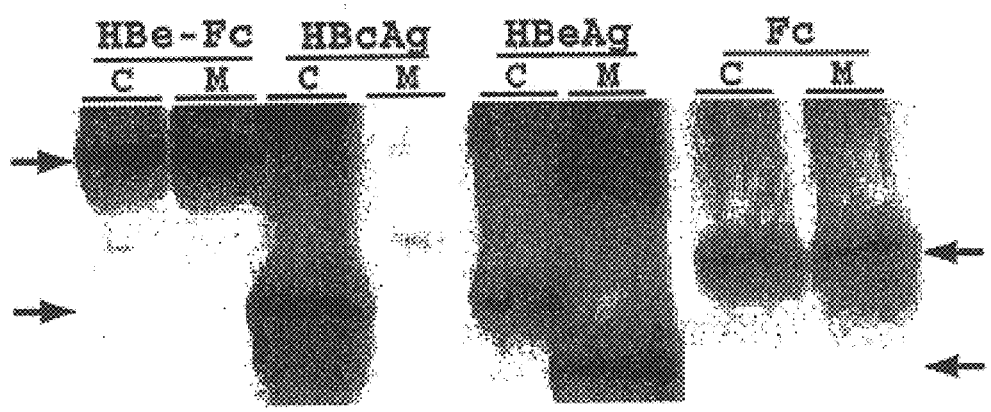
Figure 19B:
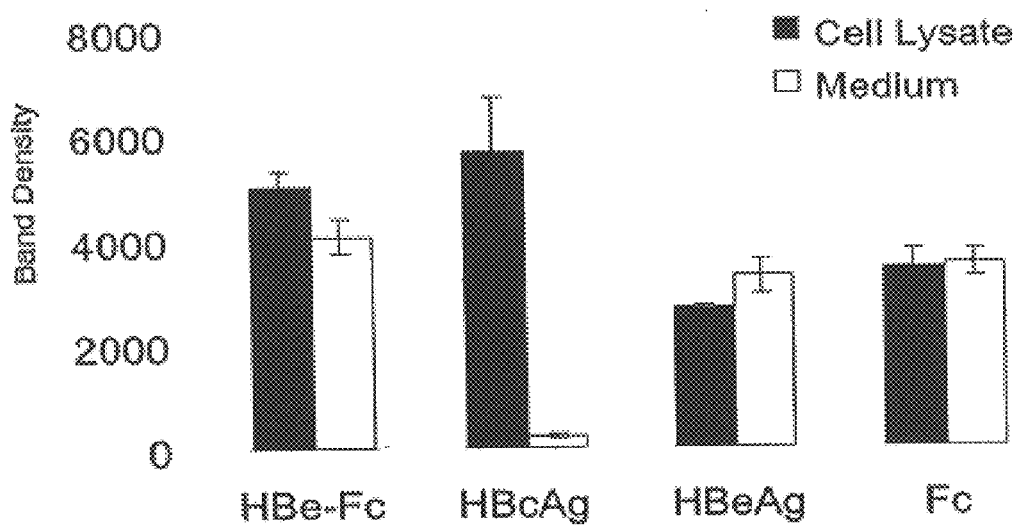

FIG. 19A and FIG. 19B show the expression of HBe-Fc, HBcAg, HBeAg, and Fc constructs. FIG. 19A shows the expression of the different constructs expressed in cells as determined by Western blot analysis. FIG. 19B shows the protein band intensity of the Western blot in FIG. 19A analyzed by a PhosphoImager (Molecular Dynamics) with an Image-Quant software.

Figure 20:
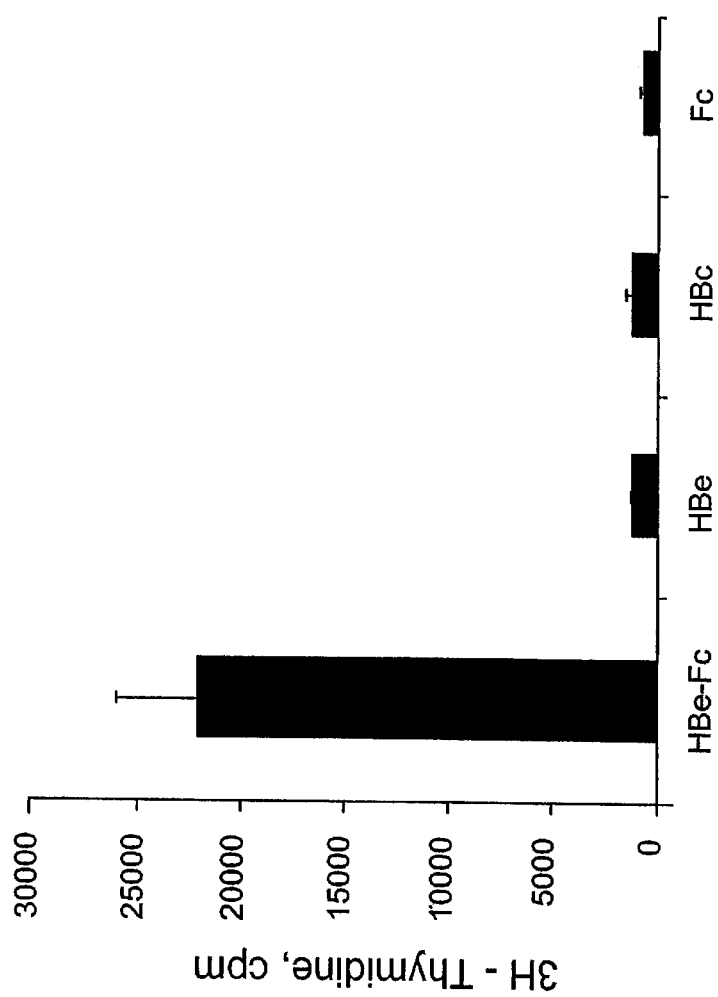

FIG. 20 illustrates the in vivo induction of T-cell responses of mice after DNA immunization with different plasmids or primed T cells that were sacrificed 4 weeks after immunization. Splenocytes were re-stimulated by HBe/cAg recombinant proteins for 5 days.

Figure 21A:
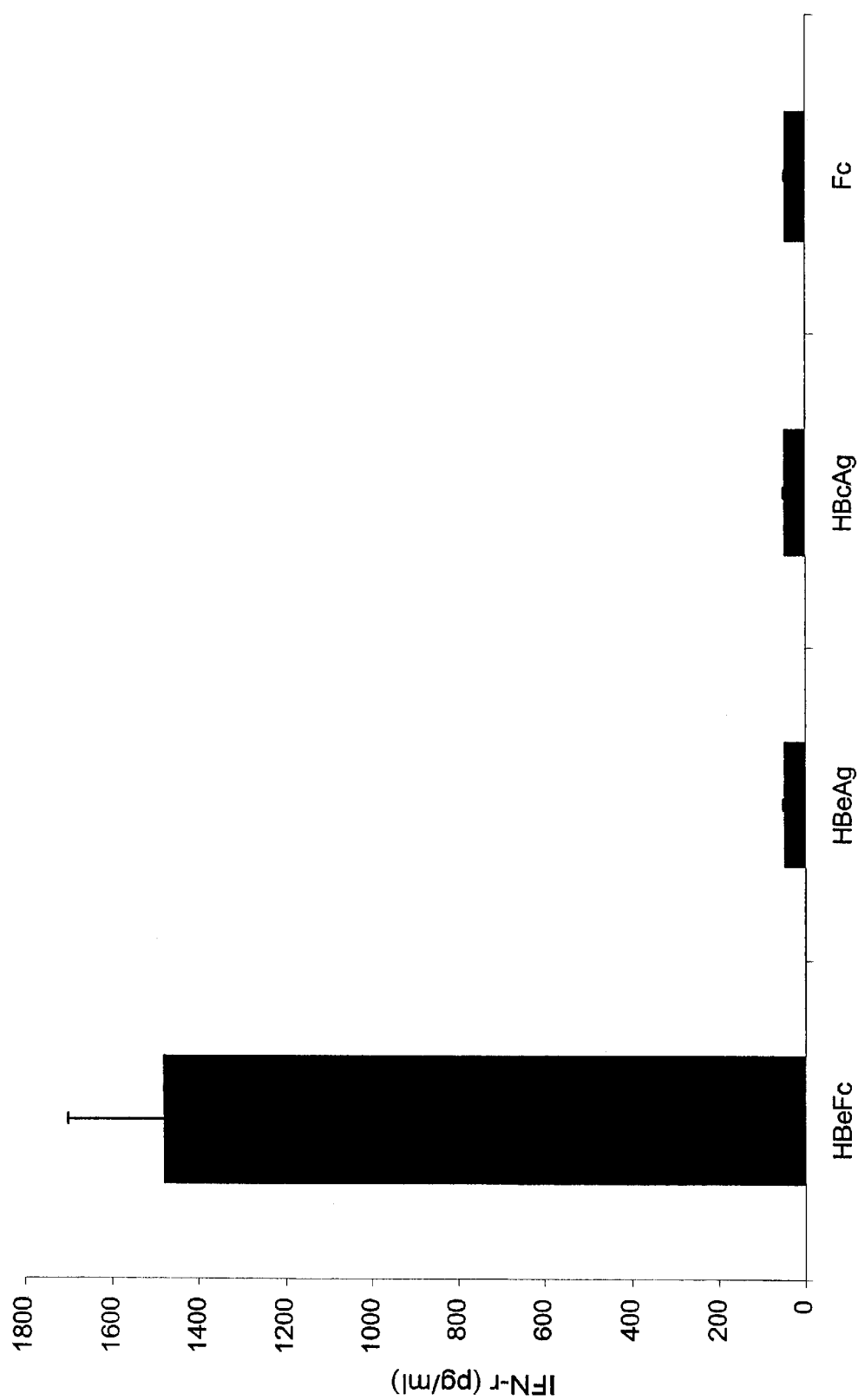
Figure 21B:
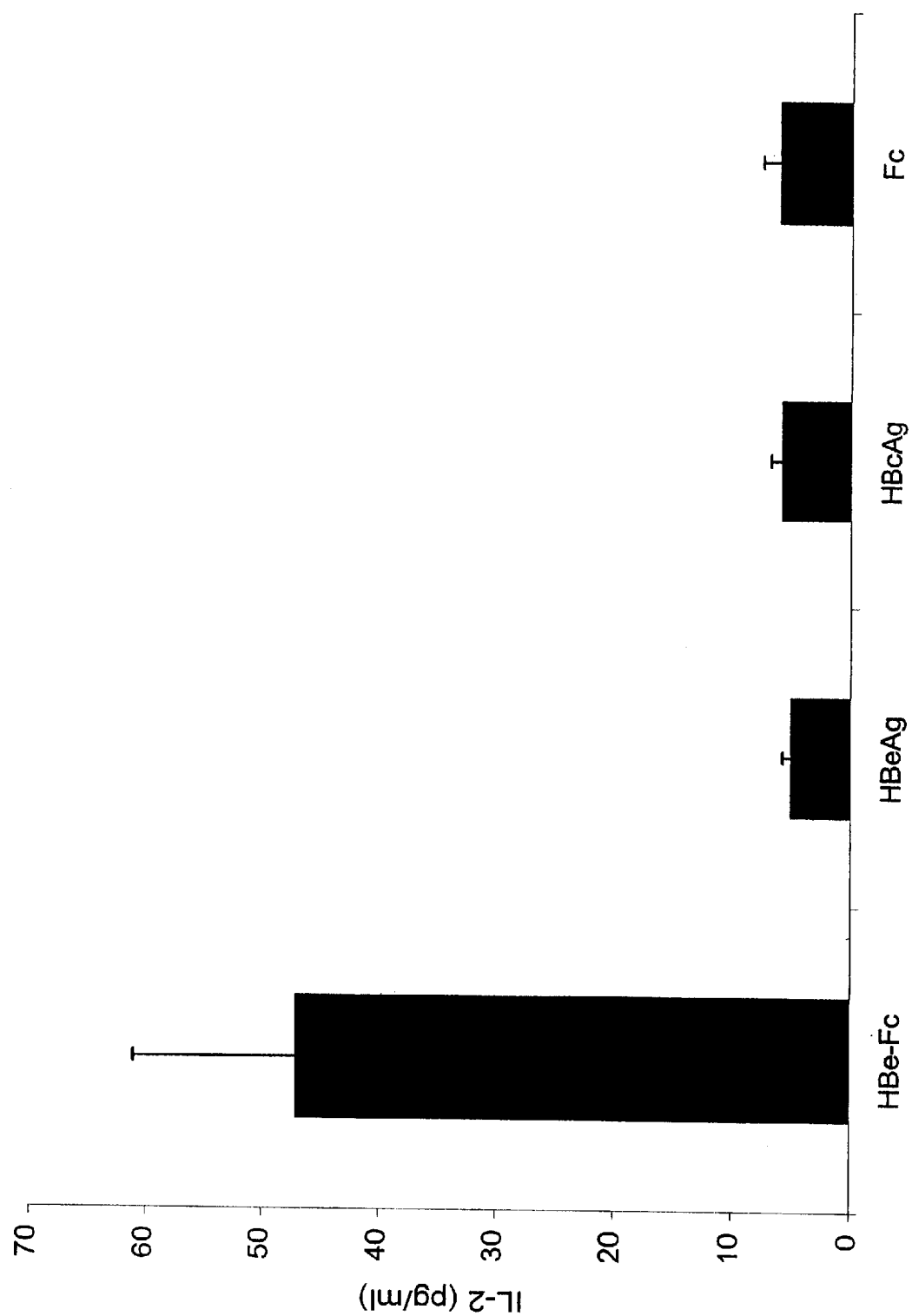
Figure 21D:
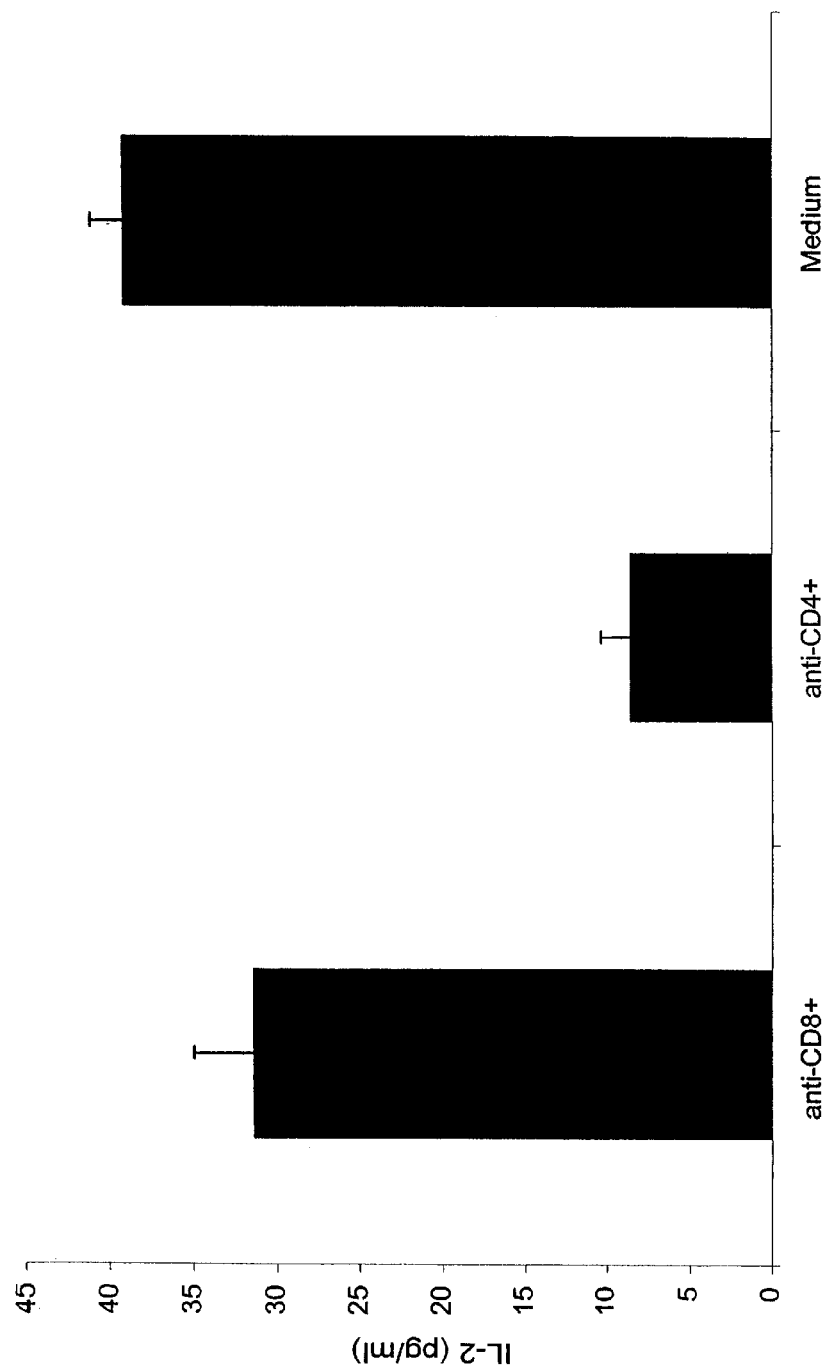

FIG. 21A, FIG. 21B, FIG. 21C and FIG. 21D illustrate the in vivo induction of CD4+ T-cell responses of mice that were immunized with different plasmids and sacrificed 4 weeks after immunization. FIG. 21A and FIG. 21B show CD4+ T cells that were co-cultured in duplicate with HBe/cAg pulsed-dendritic cells. FIG. 21C and FIG. 21D show CD4+ T cells from the HBeFc immunized mice that were co-cultured with HBe/cAg pulsed-dendritic cells in the presence or absence of anti-CD4+ or anti-CD8+ antibodies. The concentrations of IFN-γ and IL-2 in the media were determined by ELISA after 72 hours of co-culture.

Figure 22:
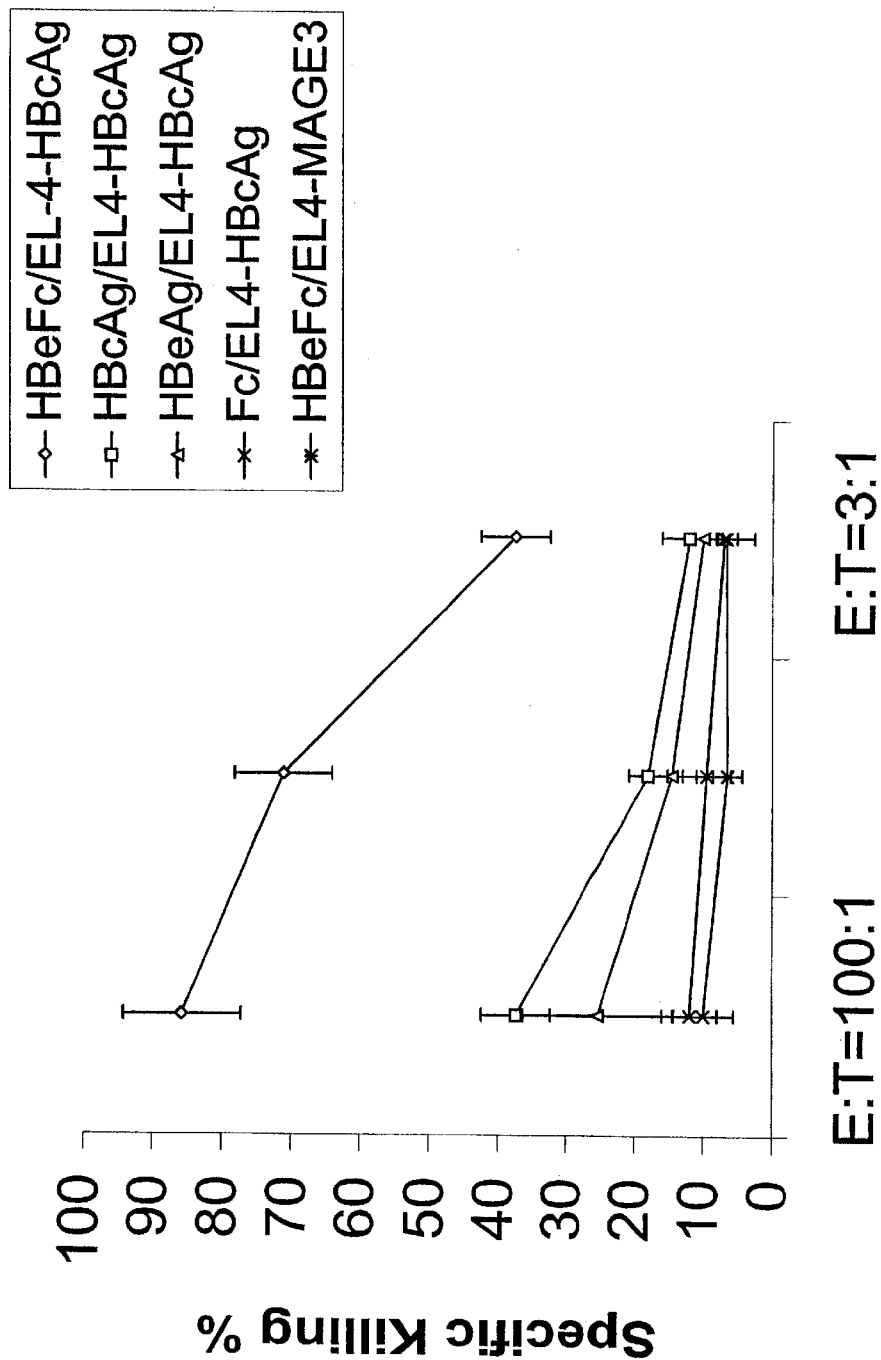

FIG. 22 illustrates the in vivo induction of CTL responses in splenocytes that were isolated from DNA immunized mice and restimulated in vitro with irradiated EL4-HBcAg cells for 5 days. The restimulated splenocytes (E) were co-cultured for 4 hr with the $^3$H-labeled target cells, EL4-HbcAg or EL4-MAGE3 (control) (T).

Figure 23:
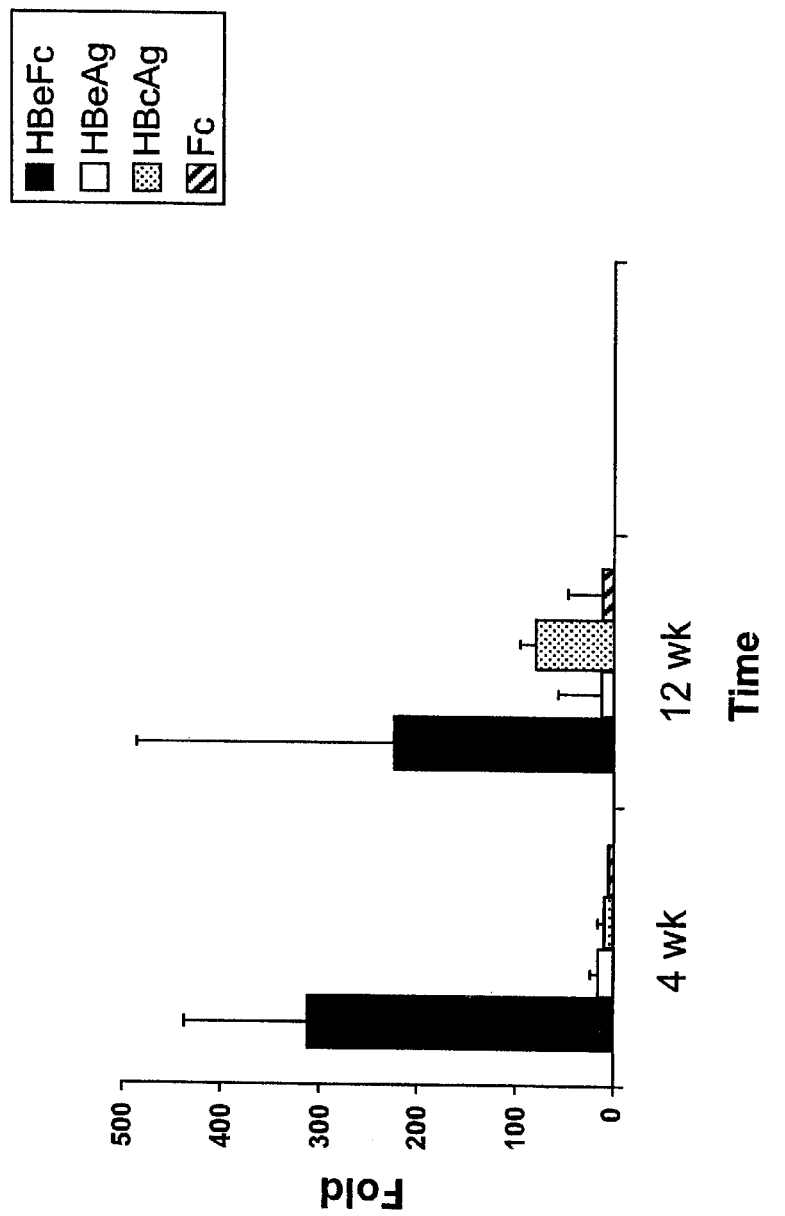

FIG. 23 shows the induction of antibody responses. The HBc/eAg-specific IgG antibodies from mice at 4–6 weeks after DNA immunization were determined by ELISA.

Figure 24:
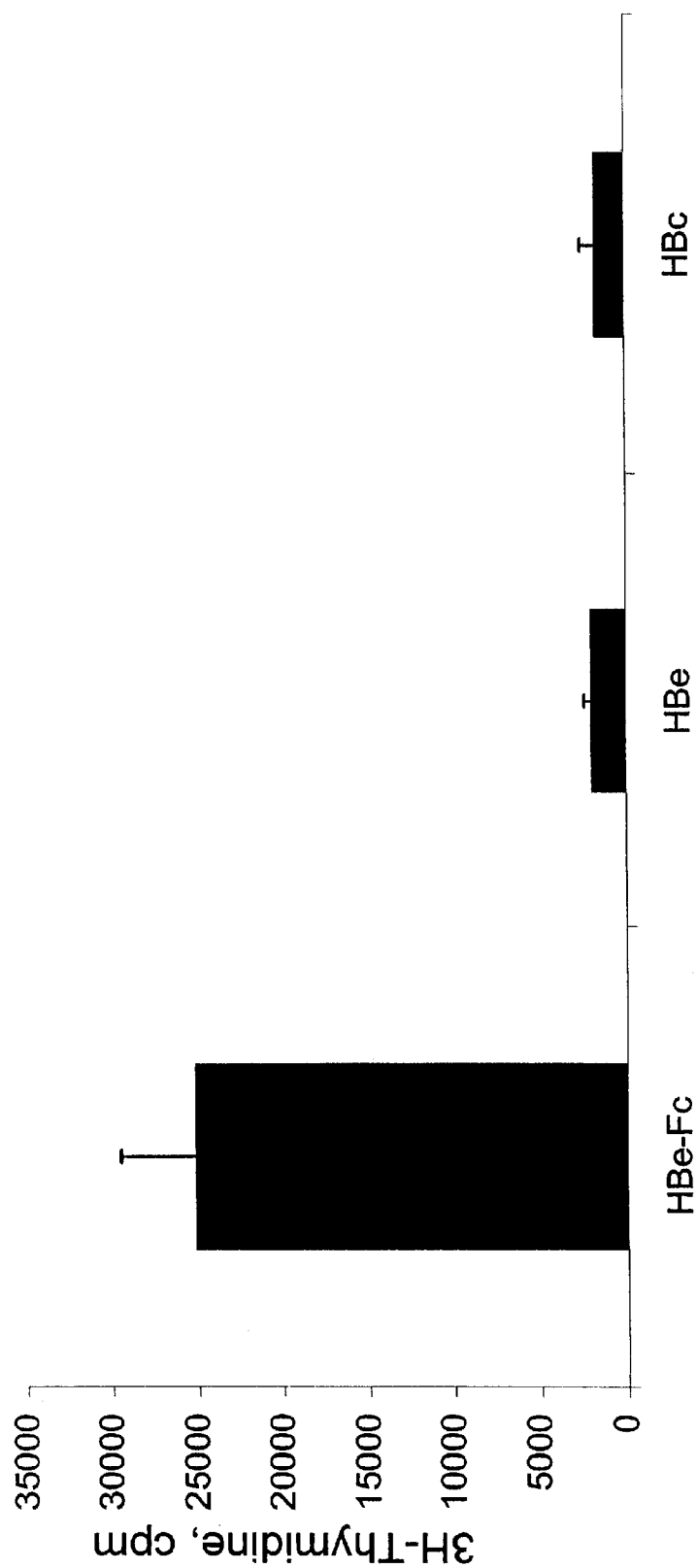

FIG. 24 illustrates data from the dendritic cell transfer experiment. The CD11C+ dendritic cells were isolated from the splenocytes of donor mice immunized with DNA vaccines. The primed-dendritic cells were injected into the lateral tail vein of syngeneic naive recipients. Two to four weeks after the adoptive transfer, T-cell proliferation assays were performed.

Figure 25:
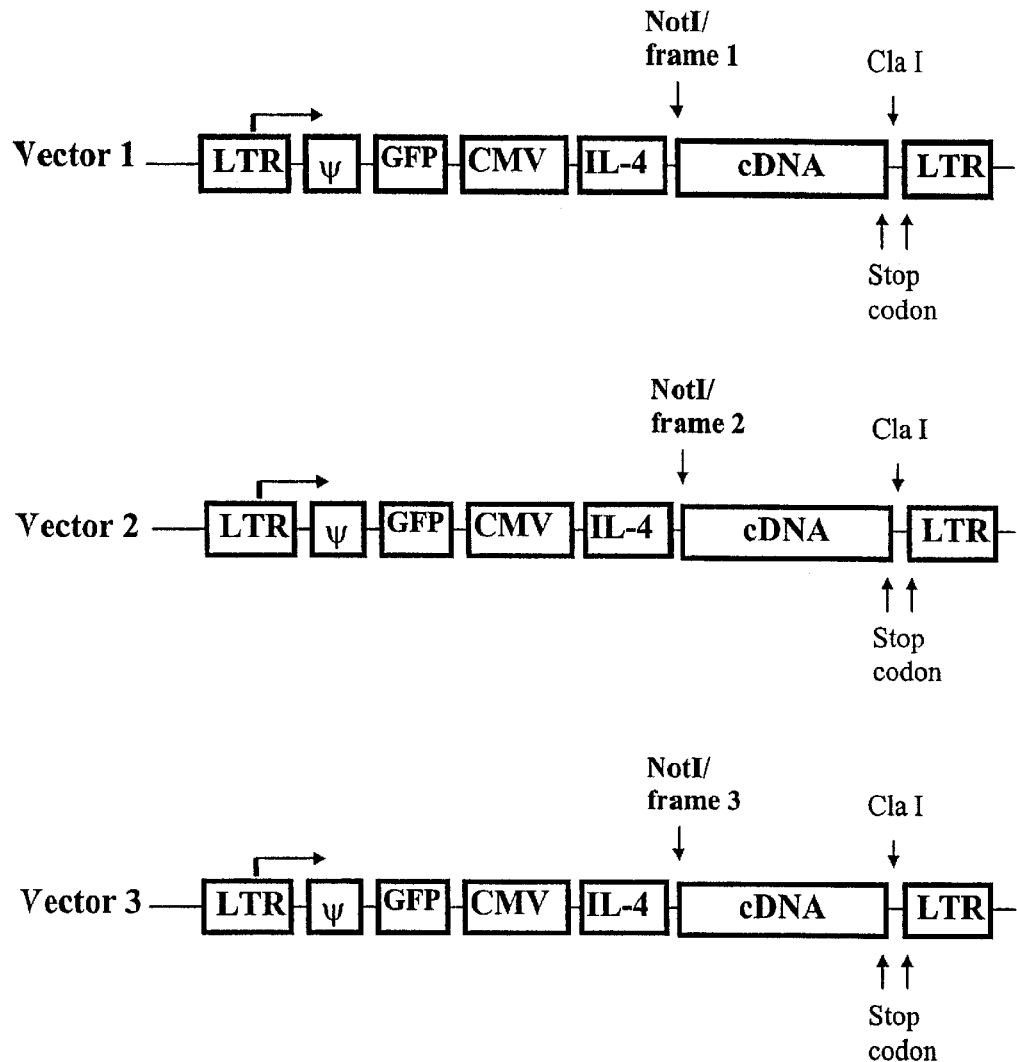

FIG. 25 illustrates a schematic of retroviral vectors for the construction of cDNA libraries to identify MHC-II restricted epitopes.

Figure 26:
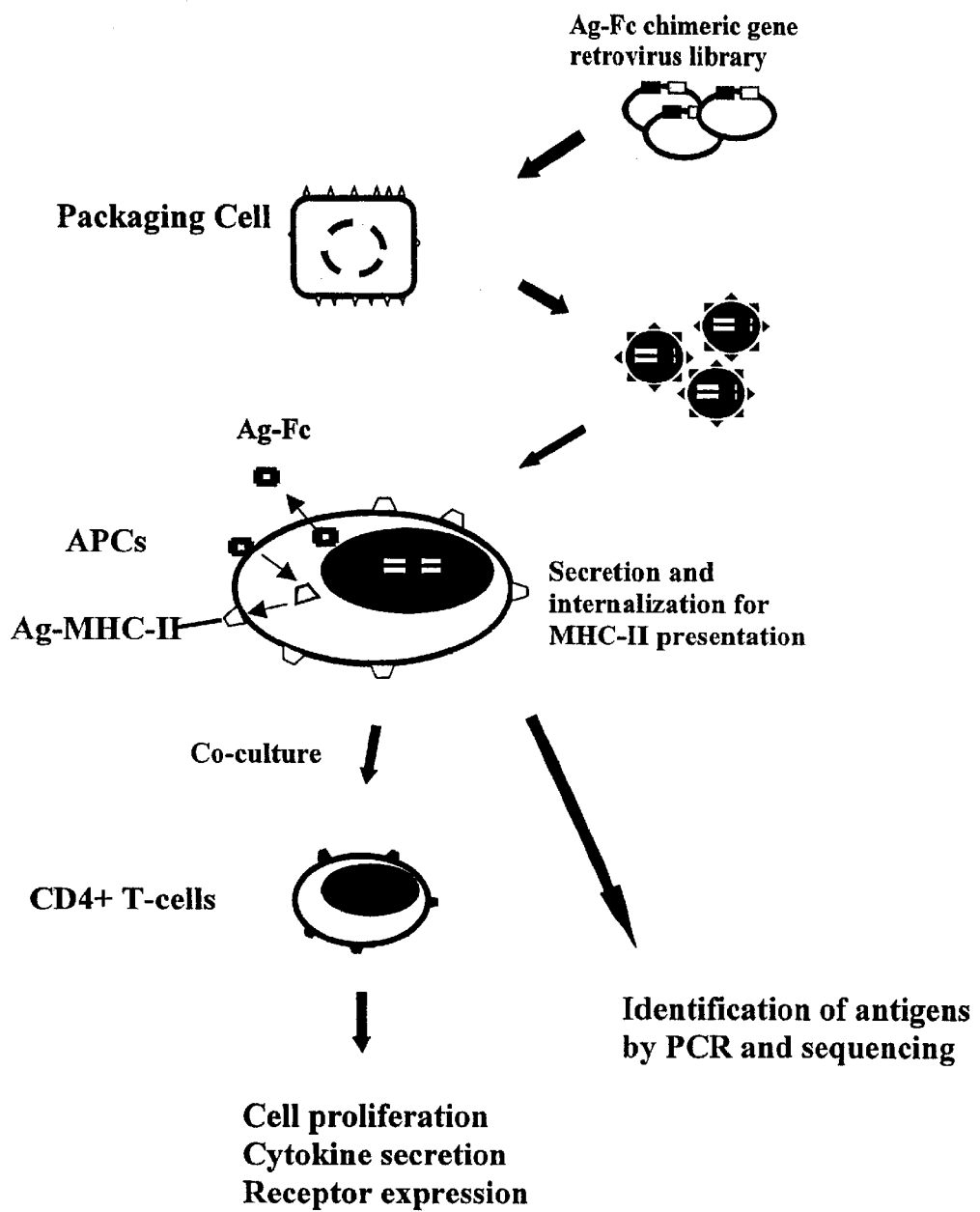

FIG. 26 illustrates a schematic of the process to identify MHC-II restricted epitopes capable of eliciting a CD4+ helper T-cell response.

DETAILED DESCRIPTION

It is readily apparent to one skilled in the art that various embodiments and modifications may be made to the invention disclose d in this Application without departing from the scope and spirit of the invention.

The term "antibody" as used herein, refers to an immunoglobulin molecule, which is able to specifically bind to a specific epitope on an antigen. Antibodies can be intact immunoglobulins derived from natural sources or from recombinant sources and can be immunoactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1988; Houston et al., 1988; Bird et al., 1988).

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates. Exemplary organisms include but are not limited to, Helicobacters, Campylobacters, Clostridia, *Corynebacterium diphtheriae, Bordetella pertussis*, influenza virus, parainfluenza viruses, respiratory syncytial virus, *Borrelia burgdorfei*, Plasmodium, herpes simplex viruses, human immunodeficiency virus, papillomavirus, *Vibrio cholera, E. coli*, measles virus, rotavirus, shigella, *Salmonella typhi, Neisseria gonorrhea*. Therefore, a skilled artisan realizes that any macromolecule, including virtually all proteins or peptides, can serve as antigens. Furthermore, antigens can be derived from recombinant or genomic DNA. A skilled artisan realizes that any DNA, which contains nucleotide sequences or partial nucleotide sequences of a pathogenic genome or a gene or a fragment of a gene for a protein that elicits an immune response results in synthesis of an antigen. Furthermore, one skilled in the art realizes that the present invention is not limited to the use of the entire nucleic acid sequence of a gene or genome. It is readily inherent that the present invention includes, but is not limited to, the use of partial nucleic acid sequences of more than one gene or genome and that these nucleic acid sequences are arranged in various combinations to elicit the desired immune response.

The term "autoimmune disease" as used herein is defined as a disorder that results from autoimmune responses. Autoimmunity is an inappropriate and excessive response to self-antigens. Examples include but are not limited to, Addision's disease, Graves' disease, Type I-Diabetes mellitus, Multiple sclerosis, Myxedema, Pernicious anemia, Rheumatic fever, Rheumatoid arthritis, Systemic lupus erythematous, and ulcerative colitis.

The term "cancer" as used herein is defined a proliferation of cells whose unique trait-loss of normal controls-results in unregulated growth, lack of differentiation, local tissue invasion, and metastasis. Examples include but are not limited to, breast cancer, prostate cancer, ovarian cancer, cervical cancer, skin cancer, pancreatic cancer, colorectal cancer, renal cancer and lung cancer.

The terms "cell," "cell line," and "cell culture" as used herein may be used interchangeably. All of these terms also include their progeny, which are any and all subsequent generations. It is understood that all progeny may not be identical due to deliberate or inadvertent mutations.

The term "cell binding element" as used herein is defined as a portion of a protein, which is capable of binding to a receptor on a cell membrane.

The term "DNA" as used herein is defined as deoxyribonucleic acid.

The term "dendritic cell" or "DC" as used herein is defined as an example of an antigen presenting cell derived from bone marrow.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly 5 amino acids or sugars in size. One skilled in the art understands that generally the overall three-dimensional structure, rather than the specific linear sequence of the molecule, is the main criterion of antigenic specificity.

The term "expression" as used herein is defined as the transcription and/or translation of a particular nucleotide sequence driven by its promoter.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well and are described infra.

The term "helper T-cell" as used herein is defined as effector T-cells whose primary function is to promote the activation and functions of other B and T lymphocytes and of macrophages. Most are CD4 T-cells.

The term "heterologous" as used herein is defined as DNA or RNA sequences or proteins that are derived from the different species.

The term "homologous" as used herein is defined as DNA or RNA sequences or proteins that are derived from the same species.

The term "host cell" as used herein is defined as cells that are expressing a heterologous nucleic acid sequence.

The term "immunoglobulin" or "Ig", as used herein is defined as a class of proteins, which functions as antibodies. The five members included in this class of proteins are IgA, IgG, IgM, IgD, and IgE. IgA functions as the primary antibody that is present in body secretions, such as saliva, tears, breast milk, gastrointestinal secretions and mucus secretions of the respiratory and genitourinary tracts. IgG functions as the most common circulating antibody. IgM is the main immunoglobulin produced in the primary response. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "major histocompatibility complex", or "MHC", as used herein is defined as a specific cluster of genes, many of which encode evolutionarily related cell surface proteins involved in antigen presentation, which are among the most important determinants of histocompatibility. Class I MHC, or MHC-I, function mainly in antigen presentation to CD8 T lymphocytes. Class II MHC, or MHC-II, function mainly in antigen presentation to CD4 T lymphocytes.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means. Furthermore, one skilled in the art is cognizant that polynucleotides include with limitation mutations of the polynucleotides, including but not limited to, mutation of the nucleotides, or nucleosides by methods well known in the art.

The term "polypeptide" as used herein is defined as a chain of amino acid residues, usually having a defined sequence. As used herein the term polypeptide is mutually inclusive of the terms "peptides" and "proteins".

The term "promoter" as used herein is defined as a DNA sequence recognized by the synthetic machinery of the cell, or introduced synthetic machinery, required to initiate the specific transcription of a polynucleotide sequence.

The term "retrogen" or "retrogen fusion protein" as used herein, means a polypeptide having an epitope that is capable of eliciting an immune response in a mammal when expressed and processed as described herein, wherein the polypeptide is fused to a cell binding element.

The term "retrogen expression vector" as used herein refers to the expression vector comprising at least a polypeptide sequence encoding a signal sequence, an antigen and a cell binding element.

The term "RNA" as used herein is defined as ribonucleic acid.

The term "recombinant DNA" as used herein is defined as DNA produced by joining pieces of DNA from different sources.

The term "recombinant polypeptide" as used herein is defined as a hybrid protein produced by using recombinant DNA methods.

The term "T-cell" as used herein is defined as a thymus-derived cell that participates in a variety of cell-mediated immune reactions.

The term "transfected" or "transformed" or "transduced" as used herein refers to a process by which exogenous nucleic acid is transferred or introduced into the host cell. A transformed cell includes the primary subject cell and its progeny.

The phrase "under transcriptional control" or "operatively linked" as used herein means that the promoter is in the correct location and orientation in relation to the polynucleotides to control RNA polymerase initiation and expression of the polynucleotides.

The term "vaccine" as used herein is defined as material used to provoke an immune response after administration of the materials to a mammal and thus conferring immunity.

The term "virus" as used herein is defined as a particle consisting of nucleic acid (RNA or DNA) enclosed in a protein coat, with or without an outer lipid envelope, which is only capable of replicating within a whole cell and spreading from cell to cell.

One embodiment of the present invention is an expression vector comprising a polynucleotide promoter sequence, a polynucleotide encoding a signal sequence, a polynucleotide encoding an antigen, a polynucleotide encoding a cell binding element, and a polynucleotide polyadenylation sequence all operatively linked.

In specific embodiments, the nucleic acid sequence encoding a fusion protein (antigen-cell binding element) is under transcriptional control of a promoter. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 genes, a discrete element overlying the start site itself helps to fix the place of initiation.

Additional promoter elements, i.e., enhancers, regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. No. 4,683,202, U.S. Pat. No. 5,928,906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (1989). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

A promoter sequence exemplified in the experimental examples presented herein is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (EV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue specific promoter, which promoter is active only in a desired tissue. Tissue specific promoters are well known in the art and include, but are not limited to, the HER-2 promoter and the PSA associated promoter sequences.

In specific embodiments of the present invention, the expression vector comprises a polynucleotide encoding a signal sequence, which directs processing of the protein encoded thereby to the appropriate cellular machinery in order that the protein is secreted from the cell. Exemplary signal sequences include, but are not limited to, hepatitis B virus E antigen signal sequence, inununoglobulin heavy chain leader sequences, cytokine leader sequences, and the like, can be used. Essentially, any signal sequence that directs secretion of a protein from a cell is suitable for use in the expression vector of the invention. In addition to signal sequences, other mechanisms for secretion may be employed, such as but not limited to, truncation or deletion of sequences inhibiting protein secretion, point mutations of sequences inhibiting protein secretion, and linkage of the protein to a viral gene to be assembled into viral particles.

An embodiment of the present invention is an expression vector wherein the polynucleotide encoding an antigen comprises a polynucleotide sequence for at least one epitope, wherein said at least one epitope induces a B cell response in a mammal.

A further embodiment of the present invention is an expression vector wherein the polynucleotide encoding an antigen comprises a polynucleotide sequence for at least one epitope, wherein said at least one epitope induces a CD4+ T-cell response in a mammal.

Another embodiment of the present invention is an expression vector wherein the polynucleotide encoding an antigen comprises a polynucleotide sequence for at least one epitope, wherein said at least one epitope induces a CD8+ T-cell response in a mammal.

A specific embodiment of the present invention is an expression vector wherein the polynucleotide sequence encoding an antigen comprises a polynucleotide sequence for at least one epitope, wherein said at least one epitope induces a B cell response, a CD4+ T-cell response and a CD8+ T-cell response in a mammal into which said antigen is introduced.

A further specific embodiment of the present invention is an expression vector wherein the polynucleotide sequence encoding an antigen comprises a polynucleotide sequence for a plurality of epitopes, wherein said plurality of epitopes induces a B cell response, a CD4+ T-cell response and a CD8+ T-cell response in a mammal into which said antigen is introduced.

In specific embodiments of the present invention, the expression vector comprises a polynucleotide sequence encoding an antigen. The polynucleotide sequences encoding an antigen are selected from at least one polynucleotide sequence associated with a disease, wherein said disease is selected from the group consisting of infectious disease, cancer and autoimmune disease. More particularly, the polynucleotide sequence encoding the antigen is a polynucleotide sequence selected from the group of pathogenic microorganisms that cause infectious disease consisting of virus, bacterium, fungus and protozoan. These DNA sequences encoding known proteins or fragments thereof include viral antigens, such as but not limited to, hepatitis B and hepatitis C virus antigens, human immunodeficiency virus antigens, including but not limited to, gp160, gp120 and gag proteins, papillomavirus antigens, including but not limited to the E7 and E6 proteins. Herpes virus proteins, such as for example, proteins encoded by Epstein-Barr virus, cytomegalovirus, herpes simplex virus types 1 and 2, and human herpes viruses 6, 7 and 8, are also contemplated in the invention as useful retrogen fusion proteins. In further embodiments, the polynucleotide encoding an antigen is a polynucleotide selected from the group consisting of breast cancer, cervical cancer, melanoma, renal cancer and prostate cancer. In addition, the protein can be one, which induces activation of an immune response directed against tumor cells for the purpose of inhibiting their growth and replication, i.e., tyrosinase that activates an immune response against melanocytes in melanoma. Other tumor-associated proteins include, but are not limited to, MART, trp, MAGE-1, MAGE-2, MAGE-3, gp100, HER-2, PSA, the Ras antigen associated with lung cancer and any other tumor specific, tissue specific or tumor associated antigens. One skilled in the art is aware of known polynucleotide sequences, which encode tumor associated antigens, as well as, are well documented in the scientific literature and heretofore unknown polynucleotide sequences are being discovered with great rapidity. In a further embodiment, the polynucleotide sequence encoding an antigen is selected from an autoimmune disease including, but not limited to, rheumatoid arthritis, systemic lupus erythematosus, multiple sclerosis, psoriasis and Crohn's disease. In addition, the invention should be construed to include DNA that encodes an autoantigen in order to induce immune tolerance in situations in which such tolerance is of benefit to the mammal. Further, the invention should be construed to include DNA that encodes an antigen, which is capable of inducing a generalized immune response in a mammal where a generalized immune response is of benefit to the mammal. A generalized immune response may be of benefit to the mammal in instances wherein the mammal is immunosuppressed, i.e., as a result of HIV infection, chemotherapy, or other immunosuppressive procedures. Such antigens may include, but are not limited to, Fc antibody fragments which when bound to Fc receptors on antigen presenting cells serve to upregulate antigen presentation by these cells. In addition, interleukins, such as, but not limited to, interleukin 5 may be used to generate a similar adjuvant effect in mammals in which induction of a generalized immune response is desired. The present invention should therefore be construed to include any known or heretofore unknown polynucleotide sequences which when included in the expression vector of the invention are capable of activating the immune response when the vector, or the fusion protein encoded thereby, is introduced into a mammal.

One skilled in the art is cognizant that it is not necessary that the nucleic acid sequence encode a full-length protein. It is simply necessary that the expressed protein comprise an epitope, which elicits the desired immune response when processed in antigen presenting cells. Thus, it is apparent from this information that the nucleic acid sequence may encode any antigen which can elicit an immune response in the animal into which the expression vector is introduced. Thus, the invention should in no way be limited to the type of nucleic acid sequences contained within the expression vector, but should include any and all nucleic acid sequences which are obtained by any means available in the art, including, without limitation, recombinant means, including also without limitation, the cloning of nucleic acid sequences from a recombinant library or a cell genome, using ordinary cloning technology and PCR™, and the like, and by synthetic means. The invention also should not be construed to be limited in any way to the source of the nucleic acid sequence, in that nucleic acid sequence may be obtained from any available source. One skilled in the art is aware that protocols for obtaining a nucleic acid sequence are well known in the art and are described, for example in Sambrook et al. (1989), and in Ausubel et al. (1997).

In specific embodiments of the present invention, the expression vector further comprises a polynucleotide sequence encoding a cell binding element. The cell binding element is a portion of a polypeptide, which facilitates binding of a protein to a cell receptor. A polynucleotide encoding any ligand that binds to a cell receptor protein may be used in the expression vector of the invention. Exemplary cell binding elements include, but are not limited to, immunoglobulin Fc fragment, toxin receptor protein cell binding domains, such as for example, the pseudomonas exotoxin cell binding domain, a cytokine, for example, interleukin 5, and interleukin 6, any type of an antibody molecule, and the like. A skilled artisan is cognizant that any antibody is capable of binding to cell surface markers on the surface of antigen presenting cells initiating internalization of the antigen/antibody complex. Thus, an antibody or a fragment thereof can be used as a cell binding element to initiate internalization. Exemplary antibodies include, but should not be limited to, antiCDC11, antiCD54, antiCD80, and antiCD86. Furthermore, one skilled in the art is cognizant that the cell binding element can be homologous or heterologous. For example, the Fc fragment can be homologous or heterologous. Thus, the invention should not be construed to be limited in any way to the source of the cell binding element in that the sequence for a cell binding element may be obtained from any available source including, without limitation, the cloning of DNA from a recombinant library or a cell genome, using ordinary cloning technology and PCR™, and the like, and by synthetic means.

In addition to using portions of known binding elements, a skilled artisan is cognizant that small peptides could be identified via a typical screening procedure well known in the art. A DNA library (cDNA or genomic) is screened to identify small peptides that bind efficiently to antigen presenting cells. Once these peptides are identified, the peptide is sequenced and used as a cell binding element in the present invention.

In expression, one will typically include a polyadenylation sequence to effect proper polyadenylation of the transcript. The nature of the polyadenylation sequence is not believed to be crucial to the successful practice of the invention, and/or any such sequence may be employed. Preferred embodiments include the SV40 polyadenylation sequence, LTR polyadenylation sequence, and/or the bovine growth hormone polyadenylation sequence, convenient and/or known to function well in various target cells. Also contemplated as an element of the expression vector is a transcriptional termination site. These elements can serve to enhance message levels and/or to minimize read through from the inserted polynucleotide sequences encoding the antigen and cell binding elements into other sequences of the vector.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast. In instances wherein it is beneficial that the expression vector replicate in a cell, the vector may integrate into the genome of the cell by way of integration sequences, i.e., retrovirus long terminal repeat sequences (LTRs), the adeno-associated virus ITR sequences, which are present in the vector, or alternatively, the vector may itself comprise an origin of DNA replication and other sequence which facilitate replication of the vector in the cell while the vector maintains an episomal form. For example, the expression vector may optionally comprise an Epstein-Barr virus (EBV) origin of DNA replication and sequences which encode the EBV EBNA-1 protein in order that episomal replication of the vector is facilitated in a cell into which the vector is introduced. For example, DNA constructs having the EBV origin and the nuclear antigen EBNA-1 coding are capable of replication to high copy number in mammalian cells and are commercially available from, for example, Invitrogen (San Diego, Calif.).

It is important to note that in the present invention it is not necessary for the expression vector to be integrated into the genome of the host cell for proper protein expression. Rather, the expression vector may also be present in a desired cell in the form of an episomal molecule. For example, there are certain cell types in which it is not necessary that the expression vector replicate in order to express the desired protein. These cells are those which do not normally replicate, such as muscle cells, and yet are fully capable of gene expression. An expression vector may be introduced into non-dividing cells and express the protein encoded thereby in the absence of replication of the expression vector.

To identify cells that contain thee nucleic acid constructs of the present invention, the cells are identified in vitro or in vivo by including a marker in the expression vector. Such markers confer an identifiable change to the cell permitting easy identification of cells containing the expression vector. Generally, a selectable marker is one that confers a property that allows for selection. A positive selectable marker is one, in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers in conjunction with FACS analysis. For example, NGFR (nerve growth factor receptor) is included in the expression vector to facilitate selection of cells comprising the vector by using a flow cytometric assay detecting NGFR expression on the cell surface. The marker used is not believed to be important, so long as it is capable of being expressed simultaneously with the nucleic acid encoding a gene product. Further examples of selectable and screenable markers are well known to one of skill in the art.

The expression vector may also comprise a prokaryotic origin of DNA replication and a gene encoding a detectable marker for selection of prokaryotic cells comprising the expression vector, for example, an antibiotic resistance gene, such as, for example, the ampicillin resistance gene.

In addition, the expression vector may be provided to the cell in the form of RNA instead of DNA. The core components of the vector are the same as those described herein for a DNA vector, and in addition, other components may be added which serve to stabilize the RNA in bodily fluids and in tissues and cells.

The actual methods of ligating together the various components described herein to generate the expression vector of the invention are well known in the art and are described, for example, in Sambrook et al. (1989), Ausubel et al. (1994), and in Gerhardt et al. (1994). in specific embodiments, the expression vector is selected from the group consisting of viral vectors, bacterial vectors and mammalian vectors. Numerous expression vector systems exist that comprise at least a part or all of the compositions discussed above. Prokaryote- and/or eukaryote-vector based systems can be employed for use with the present invention to produce nucleic acid sequences, or their cognate polypeptides, proteins and peptides. Many such systems are commercially and widely available.

The insect celUbaculovirus system can produce a high level of protein expression of a heterologous nucleic acid segment, such as described in U.S. Pat. Nos. 5,871,986, 4,879,236 and can be bought, for example, under the name MAXBAC® 2.0 from INVITROGEN® and BACPACK™ BACU-LOVIRUS EXPRESSION SYSTEM FROM CLONTECH®.

Other examples of expression vector systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

A transformed cell comprising an expression vector is generated by introducing into the cell the expression vector. The introduction of DNA into a cell or host cell is well known technology in the field of molecular biology and is described, for example, in Sambrook et al. (1989), Ausubel et al. (1994), and in Gerhardt et al., (1994). Methods of transfection of cells include calcium phosphate precipitation, liposome mediated transfection, DEAE dextran mediated transfection, electroporation and the like. Alternatively, cells may be simply transduced with the retrogen expression vector of the invention using ordinary technology described in the references and examples provided herein. The host cell includes a prokaryotic or eukaryotic cell, and it includes any transformable organism that is capable of replicating a vector and/or expressing a heterologous gene encoded by a vector. A host cell can, and has been, used as a recipient for vectors. Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). It is well within the knowledge and skill of a skilled artisan to determine an appropriate host. Generally this is based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla, Calif.). Alternatively, bacterial cells such as *E. coli* LE392 could be used as host cells for phage viruses. Eukaryotic cells that can be used as host cells include, but are not limited to yeast, insects and mammals. Examples of mammalian eukaryotic host cells for replication and/or expression of a vector include, but are not limited to, HeLa, NIH3T3, Jurkat, 293, Cos, CHO, Saos, and PC12. Examples of yeast strains include, but are not limited to, YPH499, YPH500 and YPH501. Many host cells from various cell types and organisms are available and would be known to one of skill in the art. Similarly, a viral vector may be used in conjunction with either an eukaryotic or prokaryotic host cell, particularly one that is permissive for replication or expression of the vector.

Further, the expression vector may be provided to a cell in the form of a viral vector. Viral vector technology is well known in the art and is described, for example, in Sambrook et al. (1989), and in Ausubel et al. (1994), and in other virology and molecular biology manuals. Viruses, which are useful as vectors include, but are not limited to, retroviruses, adenoviruses, adeno-associated viruses, herpes viruses, and lentiviruses.

Some vectors may employ control sequences that allow it to be replicated and/or expressed in both prokaryotic and eukaryotic cells. One of skill in the art would further understand the conditions under which to incubate all of the described host cells to maintain them and to permit replication of a vector. Also understood and known are techniques and conditions that would allow large-scale production of vectors, as well as production of the nucleic acids encoded by vectors and their cognate polypeptides, proteins, or peptides.

A specific embodiment of the present invention is a fusion protein comprising a signal sequence an antigen and a cell binding element. The invention also includes the use of the retrogen protein or fusion protein as a vaccine. The retrogen protein may be obtained by expressing the retrogen protein in any cell comprising the expression vector and separating the retrogen protein from the cell, cell debris and cell medium. Affinity column purification procedures may be especially useful for purification of the retrogen of the invention because the retrogen, by definition comprises a cell binding element. An affinity column comprising the matching cellular receptor, or a generic protein such as protein A or protein G, may be used to separate the retrogen from the cellular components. Another embodiment is a vaccine comprising antigen presenting cells that are transduced in vitro with the fusion protein.

In further embodiments, a vaccine comprises the expression vector, wherein said expression vector comprises a polynucleotide sequence encoding a promoter sequence, a polynucleotide sequence encoding a secretion signal sequence, a polynucleotide encoding an antigen, a polynucleotide encoding a cell binding element, and a polynucleotide encoding a polyadenylation sequence, all operatively linked. The vaccine comprising the expression vector is administered directly to the mammal to sites in which there are cells into which the sequences contained within the vector may be introduced, expressed and an immune response against the desired protein may be elicited. In this instance, the expression vector is administered in a pharmaceutical carrier and in a formulation such that the DNA is capable of entering cells, and being expressed therein. The expressed protein may then enter antigen presenting cells for processing and MHC presentation as described herein. A skilled artisan realizes that the DNA may be given in a variety of ways and, depending upon the route of injection, the composition of DNA may need to be manipulated. Exemplary routes of parenteral injections include, but are not limited to, intramuscular, intraperitoneal, intravenous, subcutaneous and intradermal. Further, it is not necessary that the DNA of the expression vector be introduced into the cells of the mammal by direct injection of the same into the tissues of the mammal. Rather, other means of introduction of the expression vector into the mammal may be used, including, but not limited to non-invasive pressure injection, nasal, oral, etc.

The amount of DNA which is to be introduced into the mammal is an amount sufficient for efficient expression of the DNA in the cell, such that a sufficient amount of protein is expressed and secreted therefrom, which protein is then taken up by antigen presenting cells and expressed thereon as an MHC complex. Such an amount of DNA is referred to herein as a "therapeutic amount" of DNA. The precise concentration of DNA which constitutes a therapeutic amount may be easily determined by one skilled in the art of administration of such compounds to mammals, and will of course vary depending on the components contained therein, and other factors including, but not limited to, the tissue into which the DNA is being introduced and the age and health of the mammal.

Another specific embodiment of the present invention is a vaccine comprising cells that are transduced with the expression vector. These transduced cells are in the form of a pharmaceutical composition for administration to a mammal for the purpose of eliciting an immune response therein. Expression of the retrogen protein in the cells results in secretion of the retrogen protein from the cells. Secreted retrogen protein may then be taken up by antigen presenting cells in the mammal for processing therein and expression therefrom as a MHC-I or a MHC-II complex. When the eukaryotic cell is an antigen presenting cell, the retrogen protein may be expressed therein, secreted therefrom and may reenter the cell for processing and antigenic MHC presentation. When the eukaryotic cell is not an antigen presenting cell, the cell expresses and secretes the retrogen protein, which is subsequently taken up by an antigen presenting cell for antigenic MHC presentation. Non-antigen presenting cells useful in the invention include any cell which does not process antigens for MHC presentation, i.e., muscle cells. Antigen presenting cells include dendritic cells (DC), macrophages, monocytes and the like. Tumor cells, which are also included, may be cells, which are or are not capable of processing antigens for MHC presentation.

The expression vector may also be introduced into stem cells of a mammal, either directly in vivo in the mammal, or more preferably, ex vivo in cells which are removed from the mammal and are reintroduced into the mammal following introduction of the vector into the cells. The expression vector may also be introduced into other cells in the mammal in an ex vivo approach. When the vector is introduced into cells in the mammal, it is not necessary that the vector express the protein encoded thereby immediately, in that, it may be more desirable that the protein be expressed in the cells at some later time. In this instance, the expression vector preferably comprises an inducible promoter, which is activated upon administration of the appropriate inducer to the mammal or to cells of the mammal. Ex vivo technology is well known in the art and is described, for example, in U.S. Pat. No. 5,399,346.

A further embodiment is an expression vector comprising at least a polynucleotide encoding a signal sequence, a polynucleotide encoding an antigen and a polynucleotide encoding a cell binding domain.

Another embodiment of the present invention is a method to elicit an immune response directed against an antigen. More particularly, this method utilizes the expression vector of the present invention to manipulate cells to produce endogenous antigens as if they were exogenous antigens. This novel antigen presentation strategy involves transducing cells with a novel recombinant expression vector to produce and secrete a fusion-protein consisting of an antigen and a cell-binding element. The secreted fusion protein is endocytosed or "retrogradely" transported into antigen presenting cells via receptor-mediated endocytosis (Daeron, 1997; Serre et al., 1998; Ravetch et al., 1993). As a result, the fusion protein, or "retrogen" as termed in the present disclosure because of its retrograde transport following secretion, is processed in the endosomal pathway and is presented on the cell surface of the antigen presenting cells as an MHC-II restricted exogenous antigenic fragments even though it has been produced endogenously. The MHC-II bound antigenic fragments of the antigen on the surface of the antigen presenting cells activate CD4+–T-cells that in turn stimulate CD8+ T-cells and macrophages, as well as B-cells to induce both cellular and humoral immunity.

It has also been discovered in the present invention that the retrogen protein may also be processed in the cytosolic pathway during the fusion protein synthesis, secretion and endocytosis and become associated with MHC-I on the surface of the antigen presenting cells to directly activate CD8+ T-cells. Activation of CD8+ T cells by internalized antigens is described in the art and for example, in Kovacsovics-Bankowski et al., 1995. In addition, as noted above and described in more detail elsewhere herein, B cells may be activated by the secreted retrogen. Thus, B cell activation is enhanced markedly in the present system in that CD4+ cells also activates B cells. Thus, this strategy uses a unifying mechanism to activate all of the arms of the immune system.

In specific embodiments, the expression vector is introduced into a cell to produce a transduced cell. Expression of the retrogen protein in the cells results in secretion of the retrogen protein from the cells. Secreted retrogen protein may then be taken up by antigen presenting cells in the mammal for processing therein and expression therefrom as a MHC-I or a MHC-II complex. Thus, one skilled in the art realizes that the transduced cell or first cell, secretes the antigen and the secreted antigen is internalized into a cell, a second cell, either the same cell or a different cell. When the eukaryotic cell is an antigen presenting cell, the retrogen protein may be expressed therein, secreted therefrom and may reenter the cell for processing and antigenic MHC presentation. When the eukaryotic cell is not an antigen presenting cell, the cell expresses and secretes the retrogen protein, which is subsequently taken up by an antigen presenting cell for antigenic MHC presentation. Non-antigen presenting cells useful in the invention include any cell which does not process antigens for MHC presentation, i.e., muscle cells. Antigen presenting cells include dendritic cells (DC), macrophages, monocytes and the like. Tumor cells, which are also included, may be cells, which are or are not capable of processing antigens for MHC presentation.

A further embodiment of the present invention, is a method to elicit an immune response directed against an antigen comprising the step of administering the expression vector directly to a mammal.

The invention also includes a method of screening or identifying a polynucleotide sequence which encodes at least one MHC-II restricted epitope that is capable of eliciting an immune response in a mammal. Preferably, the polypeptide, which is identified, is one which elicits an immune response that is beneficial to the mammal. The method comprises obtaining a population of isolated DNA molecules and screening for those isolated DNA molecules which encode at least one MHC-II restricted epitope that is capable of activating CD4+ helper T-cells. The DNA molecules are referred to herein as "test DNA" or "test polynucleotide sequence." The test polynucleotide sequences are cloned into the expression vector of the present invention, in the vector which is positioned between the signal sequence and the cellular binding element as depicted, for example, in FIG. 25. In the method, antigen presenting cells are transduced by introducing the vector comprising the test polynucleotide sequence into the antigen presenting cells, transduced antigen presenting cells are contacted with naive T-cells or primed T-cells and the ability of the transduced cells to activate naive CD4+ T cells in vitro is assessed by assessing whether any naive T-cells or primed T-cells are activated upon contact with said transduced antigen presenting cell. Activation of T cells by transduced antigen presenting cells is an indication that the test polynucleotide sequence contained therein is a polynucleotide sequence, or gene or fragment thereof which encodes at least one epitope capable of activating CD4+ helper T-cells to elicit an immune response in a mammal. Suitable controls which can be used in the assay include cells which are transduced with an expression vector comprising an isolated polynucleotide sequence which is known not to activate the immune response in an mammal (negative control), and cells which are transduced with an expression vector comprising an isolated polynucleotide sequence which is known to activate the immune response in an mammal (positive control). One skilled in the art is cognizant that this screening procedure can be utilized to screen the human genome to identify genes that encode proteins or epitopes that are recognized by CD4+ T-cells that could be used for immunotherapy for cancer or autoimmune disease or for gene therapy. Furthermore, other genomes can be screened including bacterial, viral, or parasitic.

The in vitro T-cell activation assay may be adapted to be a high-throughput automated assay in order to facilitate the testing of many different test polynucleotide sequences at one time. One skilled in the art recognizes that the present invention can be manipulated to transduce cells with expression vectors containing a variety of possible epitope sequences. The transduced cells may be placed in 96-well plates, containing naive T-cells, and the activation of the T-cells may be assessed by automated assessment of incorporation of radioactivity into the DNA of the T-cells, using technology readily available in clinical immunology.

In further embodiments, the protein product encoded by the test polynucleotide sequences may be further evaluated to assess activation of the immune response in a mammal in vivo. This assay is the same as the in vitro assay except, the transduced antigen presenting cells that were transduced by introducing the expression vector comprising the test polynucleotide sequences are administered to a mammal via a parenteral route. In specific embodiments, the expression vector comprising the test polynucleotide sequences is administered directly to a mammal. T-cells are collected from splenocytes and co-cultured with dendritic cells. The activation of T-cells is assessed to determine if the test polynucleotide encoding the test polypeptide is a capable of activating CD4+ helper T cells. Furthermore, one skilled in the art is cognizant that this screening procedure could be utilized to identify MHC-II restricted epitopes that could be use to treat cancer, viral infections and autoimmune disease.

As noted herein, the test polynucleotide sequences may be obtained by any ordinary means common in the art of molecular biology. For example, test polynucleotide sequences may be obtained from an expression library, which library may express proteins whose function is unknown. Test polynucleotide sequences may also be obtained from an expression library which expresses proteins of known function, but which have not heretofore been known to possess the property of activation of the immune system in an mammal. Exemplary expression cDNA libraries include, but are not limited to, tumor cells, viral genomes, bacterial genomes, parasitic genomes, and human genomes. Test polynucleotide sequences may also be obtained using combinatorial methodology, wherein it is not known at the outset whether the polynucleotide sequence encodes a protein, and moreover, it is not known whether the polynucleotide sequence encodes a protein which is capable of activating the immune response. Test polynucleotide sequences may also be obtained by synthetic methods, wherein a polynucleotide sequence is synthesized in an automated synthesizer, fragments of discrete lengths are cloned into the expression vector and are tested as described herein.

It is not always necessary that the immune response be protective, but merely that it be beneficial to the host mammal. For example, it may be beneficial to a mammal to induce immune tolerance in situations wherein an immune response to an antigen is detrimental to the mammal, for example, in certain autoimmune diseases such as rheumatoid arthritis, systemic lupus erythrematosus, psoriasis, multiple sclerosis, Crohn's disease, etc., a diminution in the immune response is desired which can be achieved by inducing immune tolerance against the offensive antigen. In this instance, the DNA comprises DNA encoding the offensive antigen which is then expressed in cells of the mammal and subsequently processed in antigen presenting cells so as to be expressed on the surface thereof as an MHC-I and/or an MHC-II complex in order to induce immune tolerance in the mammal against the antigen.

In a further embodiment, an identified polynucleotide sequence is used as a method of treating cancer, viral infection or an autoimmune disease. More particularly, the identified polynucleotide encoding a test polypeptide is transduced into antigen presenting cells and the transduced antigen presenting cells are administered directly to a mammal via a parenteral route to treat cancer, a viral infection or an autoimmune disease. Furthermore, the expression vector containing at least the polynucleotide encoding a test polypeptide and a cell binding element is administered directly into a mammal via a parenteral route to treat cancer, a viral infection or an autoimmune disease.

A further embodiment of the present invention is a method of producing a vaccine to immunize a mammal comprising the steps of: transducing antigen presenting cell by introducing the expression vector of the present invention into a cell and expressing said vector to produce an antigen under conditions wherein said antigen is secreted from the cell. In specific embodiments, antigen presenting cells are transduced with the antigen in vitro or ex vivo prior to administering the antigen presenting cells to the mammal. All of the vaccines of the present invention can be administered parenterally.

In specific embodiments, the method of inducing an immune response comprises the step of co-administering to an organism the expression vector and a cytokine expression vector. A number of studies have shown that the responses to individual plasmids can be enhanced by co-administration of a cytokine expressing plasmid. It should be noted that picogram to nanogram quantities of locally synthesized cytokine from the expression vector are too low to have systemic effects on the whole mammal, but can still strongly influence the local cytoline environment and thus the immune response to the administered antigen. Examples of cytokines include, but are not limited to, GM-CSF and IL-2. A skilled artisan readily recognizes that the polynucleotide sequences for a cytokine and the polynucleotide sequences for the antigen can be incorporated into one expression vector; thus eliminating the use of two separate vectors. In addition to cytokines, plasmids that contain unmethylated CpG sequences enhance the cell mediated (Th1) response (Carson et al., 1997). CpG sequence motifs include but are not limited to, RRCpGYY. Thus, a skilled artisan realizes that supplementation of a cytokine with the expression vector or addition of a CpG sequence motif in the present invention would result in the enhancement of the immune response.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (poho and encephalomyocarditis) have been described (Pelletier and Sonenberg, 1988), as well an IRES from a mammalian message (Macejak and Samow, 1991). IRES elements can be linked to heterologous open reading frames. Multiple open reading frames can be transcribed together; each separated by an IRES, creating polycistronic messages. By virtue of the IRES element, each open reading frame is accessible to ribosomes for efficient translation. Multiple nucleic acid sequences can be efficiently expressed using a single promoter/enhancer to transcribe a single message (U.S. Pat. Nos. 5,925,565 and 5,935,819). Furthermore, a skilled artisan is cognizant that the entire nucleic acid sequence of a gene does not have to be used. Instead, partial nucleic acid sequences of MHC class I and II restricted epitopes can be fused together, resulting in a chimeric fusion gene transcribed by one promoter. For example, a specific embodiment of the present invention is a method of simultaneously inducing both CD4+ and CD8+ T-cells comprising the steps of administering a fusion protein wherein the protein comprises both a MHC-I and MHC-II epitope fused to a cell binding element. Thus, one skilled in the art recognizes that the use of multiple antigenic sequences results in the treatment of a variety of diseases with the administration of one vaccine.

Another specific embodiment of the present invention is a method of inducing an immune response comprising the steps of administering to a mammal one expression vector, wherein said expression vector comprises a polynucleotide sequence encoding a first fusion protein and a polynucleotide sequence encoding a second fusion protein under transcriptional control of one promoter, wherein said first fusion protein comprises a first signal sequence, a first antigen and a first cell binding element and said second fusion protein comprises a second signal sequence, a second antigen and a first cell binding element. In specific embodiments, the first and second signal sequences are the same signal sequence, the first and second antigens are different antigens and the cell binding elements is a Fc fragment. In further embodiments, the first and second signal sequences are the same, the first and second antigens are different antigens and the first and second cell binding elements are the same cell binding elements. Further embodiments include, the first and second signal sequences are different, the first and second antigens are different antigens and the first and second cell binding elements are the same cell binding elements or the first and second signal sequences are the same, the first and second antigens are different antigens and the first and second cell binding elements are different cell binding elements. An additional embodiment includes that the polynucleotide sequence encoding the first fusion protein and the polynucleotide sequence encoding the second fusion protein are under separate transcriptional control, and wherein the polynucleotide sequence encoding the first fusion protein and the polynucleotide sequence encoding the second fusion protein are in tandem in one expression vector.

One skilled in the art is cognizant that multiple nucleic acid sequences can be cloned into the vector in tandem such that each nucleic acid sequence is a separate entity. Each entity contains a promoter that drives the expression of the individual nucleic acid sequence resulting in expression of separate antigens from one vector. This technique efficiently expresses nucleic acid sequences using multiple promoters to transcribe the individual messages.

A further embodiment of the present invention is a method of producing a fusion protein comprising the steps of introducing the expression vector of the present invention into a cell and expressing said vector to produce a fusion protein under conditions wherein said fusion protein is secreted from the cell. In specific embodiments, antigen presenting cells are transduced with the fusion protein in vitro. More particularly, the fusion protein is administered parenterally to a mammal.

A specific embodiment of the present invention is a method of secreting an intracellular protein comprising the steps of introducing an expression vector into a cell, wherein said expression vector comprises a polynucleotide promoter sequence, a polynucleotide encoding a signal sequence, a polynucleotide encoding an intracellular protein, a polynucleotide encoding a cell binding element, and a polynucleotide polyadenylation sequence, all operatively linked and expressing said vector to produce a fusion protein under conditions wherein said fusion protein is secreted from the cell. More specifically, the polynucleotide sequence encoding the intracellular protein is truncated or mutated to increase efficiency of secretion. In specific embodiments, the intracellular protein is HPV 16 E7.

Another specific embodiment of the present invention is a method of secreting a membrane protein comprising the steps of introducing an expression vector into a cell, wherein said expression vector comprises a polynucleotide promoter sequence, a polynucleotide encoding a signal sequence, a polynucleotide encoding a membrane protein, a polynucleotide encoding a cell binding element, and a polynucleotide polyadenylation sequence, all operatively linked and expressing said vector to produce a fusion protein under. conditions wherein said fusion protein is secreted from the cell. More specifically, the polynucleotide sequence encoding the membrane protein is truncated or mutated to increase efficiency of secretion. In specific embodiments, the membrane protein is EBV nuclear antigen 1.

The invention also includes a kit comprising the composition of the invention and an instructional material that describes adventitially administering the composition to a cell or a tissue of a mammal. In another embodiment, this kit comprises a (preferably sterile) solvent suitable for dissolving or suspending the composition of the invention prior to administering the compound to the mammal.

Dosage and Formulation

The expression vectors, transduced cells and fusion proteins (active ingredients) of this invention can be formulated and administered to treat a variety of disease states by any means that produces contact of the active ingredient with the agent's site of action in the body of the organism. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

The active ingredient can be administered orally in solid dosage forms such as capsules, tablets and powders, or in liquid dosage forms such as elixirs, syrups, emulsions and suspensions. The active ingredient can also be formulated for administration parenterally by injection, rapid infusion, nasopharyngeal absorption or dermoabsorption. The agent may be administered intramuscularly, intravenously, or as a suppository.

Gelatin capsules contain the active ingredient and powdered carriers such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium Ethylenediaminetetraacetic acid (EDTA). In addition, parenteral solutions can contain preservatives such as benzalkonium chloride, methyl- or propyl-paraben and chlorobutanol. Suitable pharmaceutical carriers are described in *Remington's Pharmaceutical Sciences*, a standard reference text in this field.

The active ingredients of the invention may be formulated to be suspended in a pharmaceutically acceptable composition suitable for use in mammals and in particular, in humans. Such formulations include the use of adjuvants such as muramyl dipeptide derivatives (MDP) or analogs that are described in U.S. Pat. Nos. 4,082,735; 4,082,736; 4,101,536; 4,185,089; 4,235,771; and 4,406,890. Other adjuvants, which are useful, include alum (Pierce Chemical Co.), lipid A, trehalose dimycolate and dimethyldioctadecylammonium bromide (DDA), Freund's adjuvant, and IL-12. Other components may include a polyoxypropylene-polyoxyethylene block polymer (Pluronic®), a non-ionic surfactant, and a metabolizable oil such as squalene (U.S. Pat. No. 4,606,91 8).

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylene mylacetate copolymers. In addition to being incorporated, these agents can also be used to trap the compound in microcapsules.

Useful pharmaceutical dosage forms for administration of the compounds of this invention can be illustrated as follows.

Capsules: Capsules are prepared by filling standard two-piece hard gelatin capsulates each with 100 milligram of powdered active ingredient, 175 milligrams of lactose, 24 milligrams of talc and 6 milligrams magnesium stearate.

Soft Gelatin Capsules: A mixture of active ingredient in soybean oil is prepared and injected by means of a positive displacement pump into gelatin to form soft gelatin capsules containing 100 milligrams of the active ingredient. The capsules are then washed and dried.

Tablets: Tablets are prepared by conventional procedures so that the dosage unit is 100 milligrams of active ingredient. 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or to delay absorption.

Injectable: A parenteral composition suitable for administration by injection is prepared by stirring 1.5% by weight of active ingredients in 10% by volume propylene glycol and water. The solution is made isotonic with sodium chloride and sterilized.

Suspension: An aqueous suspension is prepared for oral administration so that each 5 milliliters contain 100 milligrams of finely divided active ingredient, 200 milligrams of sodium carboxymethyl cellulose, 5 milligrams of sodium benzoate, 1.0 grams of sorbitol solution U.S.P. and 0.025 milliliters of vanillin.

Accordingly, the pharmaceutical composition of the present invention may be delivered via various routes and to various sites in an mammal body to achieve a particular effect (see, e.g., Rosenfeld et al., 1991; Rosenfeld et al., 1991a; Jaffe et al., supra; Berkner, supra). One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The active ingredients of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and mammal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular host.

These methods described herein are by no means all-inclusive, and further methods to suit the specific application will be apparent to the ordinary skilled artisan. Moreover, the effective amount of the compositions can be further approximated through analogy to compounds known to exert the desired effect.

Lipid Formulation and/or Nanocapsules

In certain embodiments, the use of lipid formulations and/or nanocapsules is contemplated for the introduction of the expression vector, into host cells.

Nanocapsules can generally entrap compounds in a stable and/or reproducible way. To avoid side effects due to intracellular polymeric overloading, such ultrafine particles (sized around 0.1 $\mu$m) should be designed using polymers able to be degraded in vivo. Biodegradable polyalkylcyanoacrylate nanoparticles that meet these requirements are contemplated for use in the present invention, and/or such particles may be easily made.

In a specific embodiment of the invention, the expression vector may be associated with a lipid. The expression vector associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The lipid or lipid/expression vector associated compositions of the present invention are not limited to any particular structure in solution. For example, they may be present in a bilayer structure, as micelles, or with a "collapsed" structure. They may also simply be interspersed in a solution, possibly forming aggregates which are not uniform in either size or shape.

Lipids are fatty substances which may be naturally occurring or synthetic lipids. For example, lipids include the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes.

Phospholipids may be used for preparing the liposomes according to the present invention and may carry a net positive, negative, or neutral charge. Diacetyl phosphate can be employed to confer a negative charge on the liposomes, and stearylamine can be used to confer a positive charge on the liposomes. The liposomes can be made of one or more phospholipids.

A neutrally charged lipid can comprise a lipid with no charge, a substantially uncharged lipid, or a lipid mixture with equal number of positive and negative charges. Suitable phospholipids include phosphatidyl cholines and others that are well known to those of skill in the art.

Lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Preferably, chloroform is used as the only solvent since it is more readily evaporated than methanol.

Phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition, because of the instability and leakiness of the resulting liposomes.

"Liposome" is a generic term encompassing a variety of single and multilamellar lipid vehicles formed by the generation of enclosed lipid bilayers or aggregates. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). However, the present invention also encompasses compositions that have different structures in solution than the normal vesicular structure. For example, the lipids may assume a micellar structure or merely exist as nonuniform aggregates of lipid molecules. Also contemplated are lipofectamine-nucleic acid complexes.

Phospholipids can form a variety of structures other than liposomes when dispersed in water, depending on the molar ratio of lipid to water. At low ratios the liposome is the preferred structure. The physical characteristics of liposomes depend on pH, ionic strength and/or the presence of divalent cations. Liposomes can show low permeability to ionic and/or polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and/or results in an increase in permeability to ions, sugars and/or drugs.

Liposomes interact with cells via four different mechanisms: Endocytosis by phagocytic cells of the reticuloendothelial system such as macrophages and/or neutrophils; adsorption to the cell surface, either by nonspecific weak hydrophobic and/or electrostatic forces, and/or by specific interactions with cell-surface components; fusion with the plasma cell membrane by insertion of the lipid bilayer of the liposome into the plasma membrane, with simultaneous release of liposomal contents into the cytoplasm; and/or by transfer of liposomal lipids to cellular and/or subcellular membranes, and/or vice versa, without any association of the liposome contents. Varying the liposome formulation can alter which mechanism is operative, although more than one may operate at the same time.

Liposome-mediated oligonucleotide delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the lipid may be associated with a hemagglutinating virus (HVJ). This has been shown to facilitate fusion with the cell membrane and promote cell entry of liposome-encapsulated DNA (Kaneda et al., 1989). In other embodiments, the lipid may be complexed or employed in conjunction with nuclear non-histone chromosomal proteins (HMG-1) (Kato et al., 1991). In yet further embodiments, the lipid may be complexed or employed in conjunction with both HVJ and HMG-1. In that such expression vectors have been successfully employed in transfer and expression of an oligonucleotide in vitro and in vivo, then they are applicable for the present invention. Where a bacterial promoter is employed in the DNA construct, it also will be desirable to include within the liposome an appropriate bacterial polymerase.

Liposomes used according to the present invention can be made by different methods. The size of the liposomes varies depending on the method of synthesis. A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

Liposomes within the scope of the present invention can be prepared in accordance with known laboratory techniques. In one preferred embodiment, liposomes are prepared by mixing liposomal lipids, in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25–50 mM phospholipid in sterile, pyrogen-free water by shaking until all the lipid film is resuspended. The aqueous liposomes can be then separated into aliquots, each placed in a vial, lyophilized and sealed under vacuum.

In the alternative, liposomes can be prepared in accordance with other known laboratory procedures: the method of Bangham et al. (1965), the contents of which are incorporated herein by reference; the method of Gregoriadis, as described in *DRUG CARRIERS IN BIOLOGY AND MEDICINE*, G. Gregoriadis ed. (1979) pp. 287–341, the contents of which are incorporated herein by reference; the method of Deamer and Uster, 1983, the contents of which are incorporated by reference; and the reverse-phase evaporation method as described by Szoka and Papahadjopoulos, 1978. The aforementioned methods differ in their respective abilities to entrap aqueous material and their respective aqueous space-to-lipid ratios.

The dried lipids or lyophilized liposomes prepared as described above may be dehydrated and reconstituted in a solution of inhibitory peptide and diluted to an appropriate concentration with a suitable solvent, e.g., DPBS. The mixture is then vigorously shaken in a vortex mixer. Unencapsulated nucleic acid is removed by centrifugation at 29,000×g and the liposomal pellets washed. The washed liposomes are resuspended at an appropriate total phospholipid concentration, e.g., about 50–200 mM. The amount of nucleic acid encapsulated can be determined in accordance with standard methods. After determination of the amount of nucleic acid encapsulated in the liposome preparation, the liposomes may be diluted to appropriate concentrations and stored at 4° C. until use.

A pharmaceutical composition comprising the liposomes will usually include a sterile, pharmaceutically acceptable carrier or diluent, such as water or saline solution.

Gene Therapy Administration

One skilled in the art recognizes that the expression vector of the present invention can be utilized for gene therapy. For gene therapy, a skilled artisan would be cognizant that the vector to be utilized must contain the gene of interest operatively linked to a promoter. For antisense gene therapy, the antisense sequence of the gene of interest would be operatively linked to a promoter. One skilled in the art recognizes that in certain instances other sequences such as a 3' UTR regulatory sequences are useful in expressing the gene of interest. Where appropriate, the gene therapy vectors can be formulated into preparations in solid, semisolid, liquid or gaseous forms in the ways known in the art for their respective route of administration. Means known in the art can be utilized to prevent release and absorption of the composition until it reaches the target organ or to ensure timed-release of the composition. A pharmaceutically acceptable form should be employed which does not ineffectuate the compositions of the present invention. In pharmaceutical dosage forms, the compositions can be used alone or in appropriate association, as well as in combination, with other pharmaceutically active compounds. A sufficient amount of vector containing the therapeutic nucleic acid sequence must be administered to provide a pharmacologically effective dose of the gene product.

One skilled in the art recognizes that different methods of delivery may be utilized to administer a vector into a cell. Examples include: (1) methods utilizing physical means, such as electroporation (electricity), a gene gun (physical force) or applying large volumes of a liquid (pressure); and (2) methods wherein said vector is complexed to another entity, such as a liposome, aggregated protein or transporter molecule.

Accordingly, the present invention provides a method of transferring a therapeutic gene to a host, which comprises administering the vector of the present invention, preferably as part of a composition, using any of the aforementioned routes of administration or alternative routes known to those skilled in the art and appropriate for a particular application. Effective gene transfer of a vector to a host cell in accordance with the present invention to a host cell can be monitored in terms of a therapeutic effect (e.g. alleviation of some symptom associated with the particular disease being treated) or, further, by evidence of the transferred gene or expression of the gene within the host (e.g., using the polymerase chain reaction in conjunction with sequencing, Northern or Southern hybridizations, or transcription assays to detect the nucleic acid in host cells, or using immunoblot analysis, antibody-mediated detection, mRNA or protein half-life studies, or particularized assays to detect protein or polypeptide encoded by the transferred nucleic acid, or impacted in level or function due to such transfer).

These methods described herein are by no means all-inclusive, and further methods to suit the specific application will be apparent to the ordinary skilled artisan. Moreover, the effective amount of the compositions can be further approximated through analogy to compounds known to exert the desired effect.

Furthermore, the actual dose and schedule can vary depending on whether the compositions are administered in combination with other pharmaceutical compositions, or depending on interindividual differences in pharmacokinetics, drug disposition, and metabolism. Similarly, amounts can vary in in vitro applications depending on the particular cell line utilized (e.g., based on the number of vector receptors present on the cell surface, or the ability of the particular vector employed for gene transfer to replicate in that cell line). Furthermore, the amount of vector to be added per cell will likely vary with the length and stability of the therapeutic gene inserted in the vector, as well as also the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

It is possible that cells containing the therapeutic gene may also contain a suicide gene (i.e., a gene which encodes a product that can be used to destroy the cell, such as herpes simplex virus thymidine kinase). In many gene therapy situations, it is desirable to be able to express a gene for therapeutic purposes in a host cell but also to have the capacity to destroy the host cell once the therapy is completed, becomes uncontrollable, or does not lead to a predictable or desirable result. Thus, expression of the therapeutic gene in a host cell can be driven by a promoter although the product of said suicide gene remains harmless in the absence of a prodrug. Once the therapy is complete or no longer desired or needed, administration of a prodrug causes the suicide gene product to become lethal to the cell. Examples of suicide gene/prodrug combinations which may be used are Herpes Simplex Virus-thymidine kinase (HSV-tk) and ganciclovir, acyclovir or FIAU; oxidoreductase and cycloheximide; cytosine deaminase and 5-fluorocytosine; thymidine kinase thymidilate kinase (Tdk::Tmk) and AZT; and deoxycytidine kinase and cytosine arabinoside.

The following examples are offered by way of example, and are not intended to limit the scope of the invention in any manner.

EXAMPLE 1

Construction and Expression of HBe Antigen in a Retroviral Vector

Figures 1A, 1B:
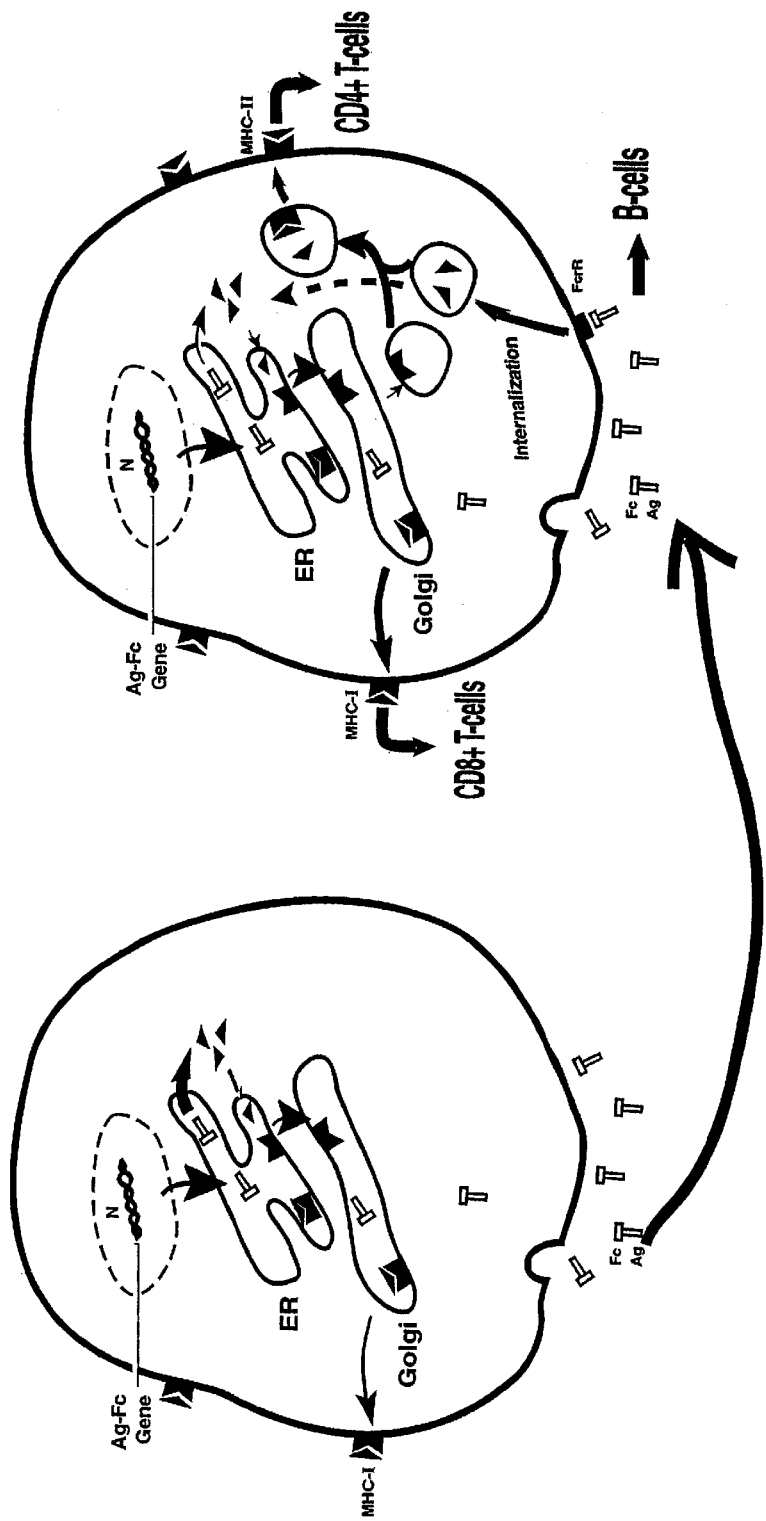
Figure 2A:
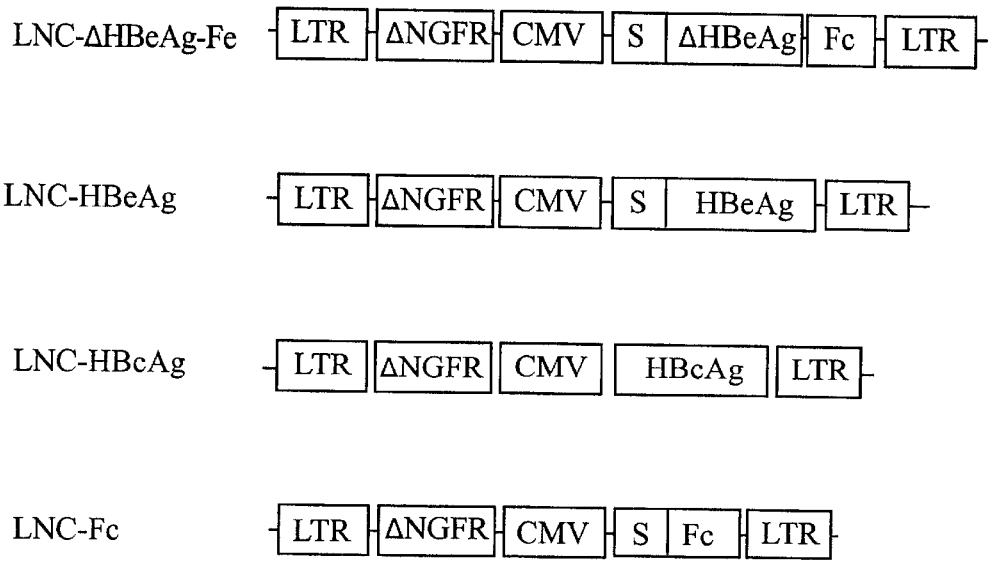

Although both HBcAg and HBeAg proteins are encoded by the HBV pre-CC gene, the secretory HBeAg protein is initiated at a start codon twenty nine residues upstream of the start codon for HBcAg. The HBeAg gene obtained from the American Type Culture Collection (Rockville, Md.) was repaired to correct two mutations. The two mutations were found to occur from a single base pair deletion, which caused a frameshift at codon 74, resulting in two consecutive stop codons at 84 and 85. These mutations were corrected by inserting the deleted base using PCR mutagenesis. The arginine-rich, C'-terminal sequence of HBeAg (aa 150–185) which is cleaved during viral infection was deleted. The truncated HBeAg gene was then fused in-frame with an IgG Fc fragment. The HBe-retrogen fusion gene (HBe-retrogen) was cloned into the retroviral vector (LNC-NGFR), or the expression vector pRc/CMV. The vectors comprising HBcAg (cytosolic) and HBeAg (secretory) were constructed using technology available in the art and described, for example in, Sambrook et al. (1989) and in Ausubel et al. (1997). The IgG Fc fragment gene was fused with an IgG signal leader sequence and was cloned into the expression vectors as shown in FIG. 2A. In this manner, a series of control retroviral vectors containing the HBeAg gene (secretory), the Fc fragment gene with a signal leader sequence (secretory), or the HBcAg gene (cytosolic), were constructed as represented in FIG. 2A.

Figure 3:
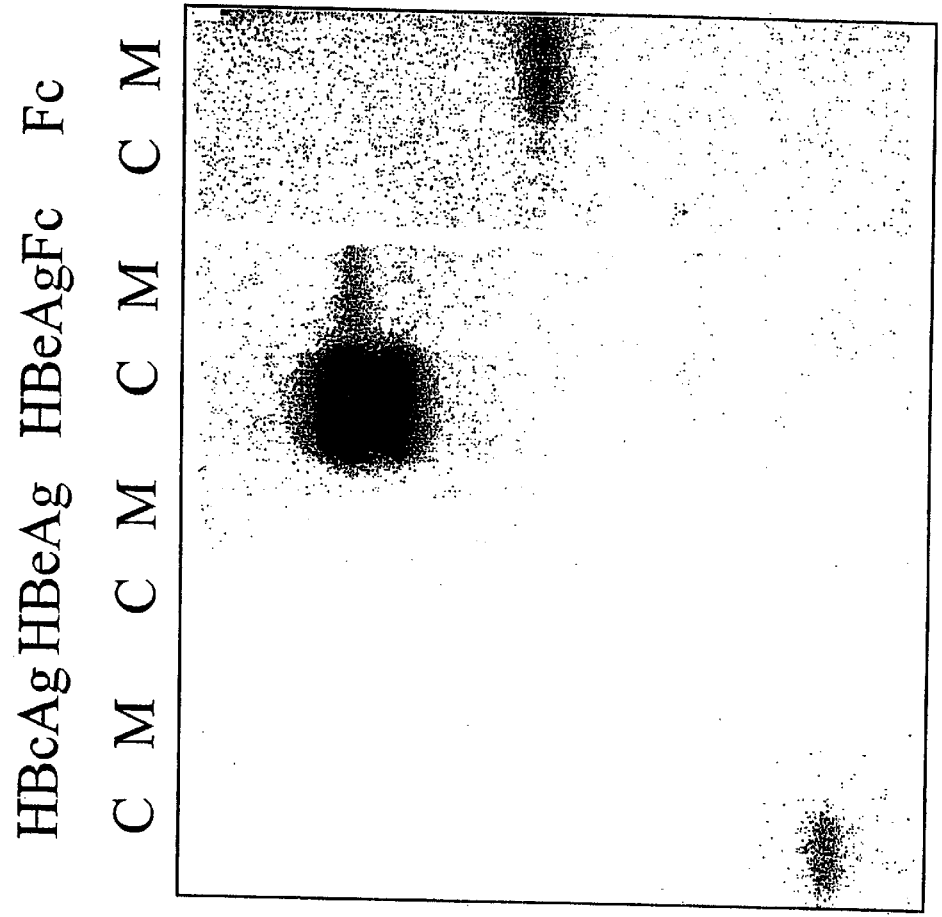
Figure 4A:
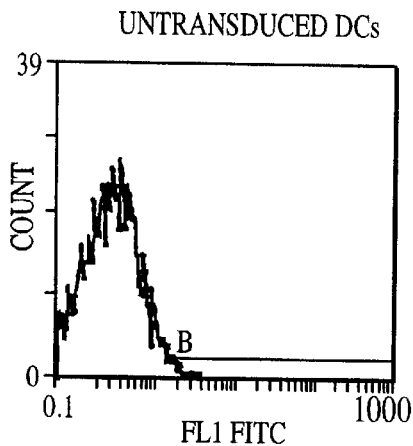
Figure 4B:
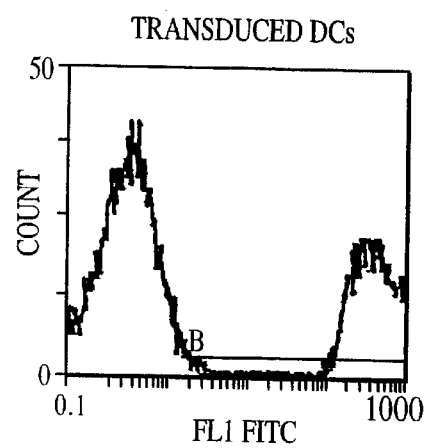
Figure 4C:
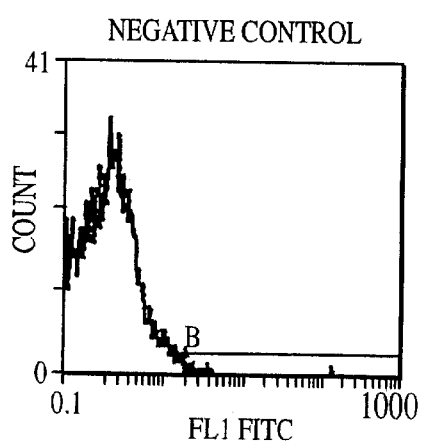
Figure 5A:
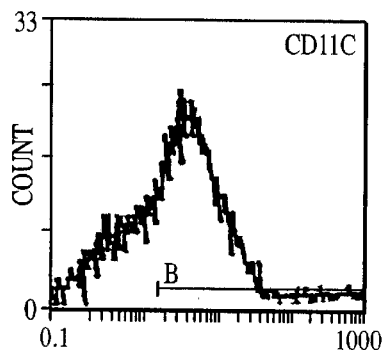
Figure 5B:
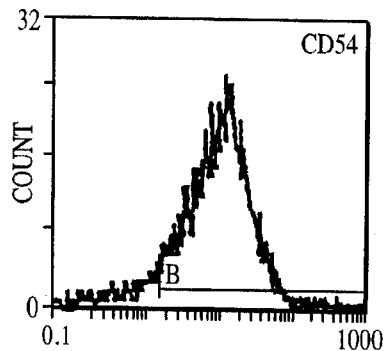
Figure 5C:
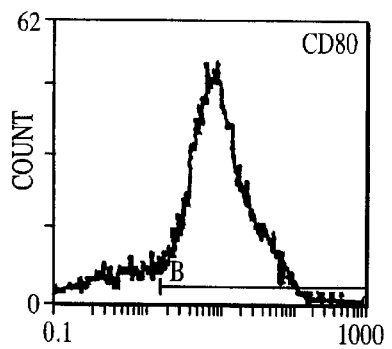
Figure 5D:
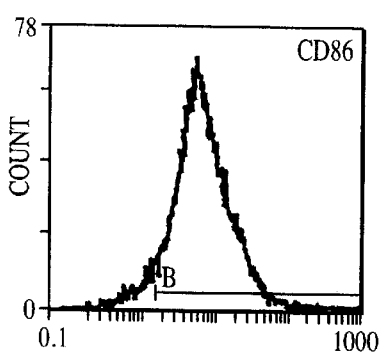
Figure 5E:
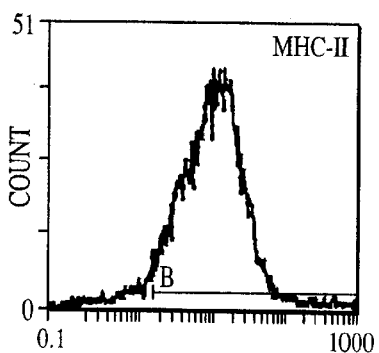

To assess the expression and secretion of the HBe-Fc fusion protein, COS cells were transfected with various expression vectors and 48 hours later, the cells were radio-labeled. As shown in FIG. 3, a protein band corresponding to the HBeAg-Fc fusion protein, was detected in both cell lysates and culture medium when either was precipitated with an anti-human IgG or anti-HBeAg antibody (Sigma Chemical Co. St. Louis, Mo.).

Immunofluorescent staining of transfected cells also exhibited a typical secretory protein pattern. The HBcAg proteins were only observed in the cell lysates obtained from the transfected cells, and the HBeAg and Fc fragment proteins were observed in both the culture medium and the cell lysates. These results indicate that the HBeAg-Fc proteins (HBe-retrogen) are efficiently produced and secreted from cells.

EXAMPLE 2

Transduction and Expression of HBe-Retrogen in Dentritic Cells (DCs)

To assess the "retrogen" strategy in DCs, the retroviral vectors containing the HBe-retrogen or various control genes including a NGFR marker (FIG. 2A) were produced from PA317 packaging cells using the transient transfection. Murine bone marrow cells were obtained from C57BL/B6 mice. The cells were stimulated in culture medium supplemented with murine stem cell factor (SCF) and IL-6, and were transduced with the retroviral vectors as described infra, et al.
Transduction of DCs PA3 17 packaging cells obtained from the American Type Culture Collection (Rockville, Md.) at approximately 40% confluency were cultured in 100 mm culture dishes with Dulbecco's Modified Eagle Media (DMEM) containing 10% fetal bovine serum (FBS). The cells were transfected with 10–15 µm filter.

Murine bone marrow was flushed from the bones of the mouse limbs, passed through a nylon mesh and depleted of red cells with ammonium chloride. After extensive washing with RPMI-1640, the cells were incubated with rabbit complement and a set of cocktail of monoclonal antibodies, anti-CD4+ , anti-CD8+, anti-B cells and anti-MHC class positive cells in RPMI-1640 at 37° C. for 40–60 minutes. After extensive washing with RPMI-1640, $5\times10^5$ cells/ml were suspended in RPMI-1640 supplemented with 6% FBS, 80 ng mSCF/ml and 20 U rmIL-6/ml. The cells were plated in 12-well culture plates (3 ml/well), incubated at 37° C. and 5% $CO_2$ overnight, and then replaced with the fresh medium comprising the same ingredients. After 48-hour incubation, the cells were collected by centrifugation, resuspended in 1.5 ml of the retrovirus supernatants, and placed onto 24-well culture plates, which were coated with Retronectin at a concentration of 10 mg/ml. The cells were centrifuged at 2,500 rpm at 37° C. for 90–120 minutes, and were then incubated at 37° C. and 5% $CO_2$ for an additional 3–4 hours for retroviral transduction. The retrovirus supernatants were then replaced with 2.5 ml of RPMI-1640 supplemented with 5% FBS, 10 ng mSCF/ml, 60 ng mGM-CSF/ml and 100 U mIL-4/ml (R&D Systems, Minneapolis, Minn.) overnight. The transduction procedure was then repeated 2–3 times. After transduction, the cells were washed and cultured in Opti-MEM (GIBCO, Grand Island, N.Y.) containing mGM-CSF and mIL-4 for several days in order to further mature the DCs prior to harvest (Banchereau et al., 1998; Inaba et al., 1992).
Evaluation of Transduction (Measurement of Expression)

After several days in culture, the cells exhibited typical DC morphology and high levels of MHC, adhesion, and co-stimulation molecules (CD11, CD54, CD80 and CD86) were expressed on the bone-marrow-derived DCs (FIGS. 4A–4C and 5A–5E). About 20 to 30% of the cells in the culture were transduced, as determined by anti-NGFR staining. Transcription of the HBe-retrogen gene in the DCs was demonstrated in a RT-PCR assay.

The RT-PCR assay was performed as follows: Cellular RNA was extracted from the DCs using Trizoal (Gibco-BRL Grand Island, N.Y.) and was treated with RNASE-free DNASE at 37° C. for 30 minutes. After reverse transcription, the cDNAs were used as templates for a PCR reaction using a pair of primers corresponding to the HBeAg gene. The PCR products were analyzed by electrophoresis through agarose.

Taken together, these results indicate that the HBe-retrogen fusion gene was efficiently transduced into murine bone marrow cells and was expressed in bone-marrow-derive DCs. Interestingly, the surface expression of MHC-II and costimulation molecules on DCs comprising transduced HBe-retrogen were significantly higher than the expression of the molecules on DCs transduced with HBeAg or HBcAg. This observation suggests that binding of the Fc to receptor activated the DCs.

EXAMPLE 3

In vitro Activation of Naive CD4+−T-cells

To evaluate whether the transduced DCs were capable of priming naive CD4+−T-cells in cell culture, naive CD4+−T-cells isolated from C57BL/B6 mouse spleen cells were co-cultured with murine DCs transduced with the retroviral vectors of Example 1 at a ratio of 1:20 (DCs:T-Cells). CD4+ T cells were isolated from the suspension of mouse spleens using a CD4+ T cell enriching column (R&D Systems, Minneapolis, Minn.). CD8+ T cells were isolated from the suspension of mouse spleens using a CD8+ T cell enriching column (R&D System, Minneapolis, Minn.). Purified CD4+ or CD8+ T cells were cultured in RPMI-1640 supplemented with 10% FBS at 37° C. and 5% $CO_2$.

Figure 6A:
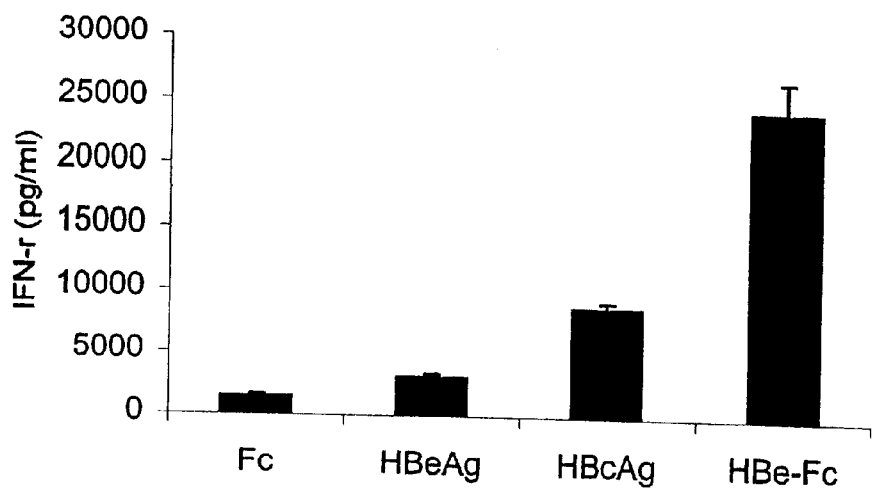
Figure 6B:
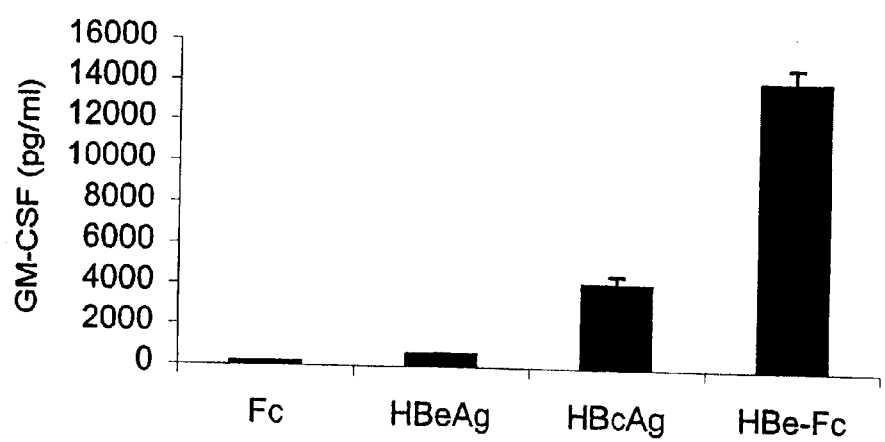

When naive CD4+−T-cells were co-cultured with the DCs transduced with either HBcAg, HBeAg or Fc fragment gene, only low or background levels of granulocyte-macrophage colony-stimulating factor (GM-CSF) and interferon (IFN)-γ were detected by ELISA in the culture medium. Further, no apparent T-cell proliferation was observed when either cell numbers or the incorporation rate of $^3$H-thymidine was monitored. In contrast, when naive CD4+ T-cells were co-cultured with the DCs transduced with the HBe-retrogen for 5 days, T-cells actively proliferated and high levels of GM-CSF and IFN-γ were detected in the culture medium (FIGS. 6A and 6B). These results suggest that secretory HBeAg or cytosolic HBcAg could not be efficiently processed and presented to MHC-II by DCs. In contrast, secretory HBe-retrogens could be efficiently processed following Fc-receptor-mediated internalization and presentation to MHC-II in DCs, leading to the vitro activation of naive CD4+ T-cells.

No apparent naive CD8+ T-cell activation was detected in the co-culture with the transduced DCs. The failure to detect naive CD8+ T-cell activation in the cell-culture may be due to the fact that there is only one known MHC-I restricted epitope in the HBe Ag and that CD4+–T-cells are required for efficient activation of CD8+ T-cells (Ridge et al., 1998).

Figure 7A:
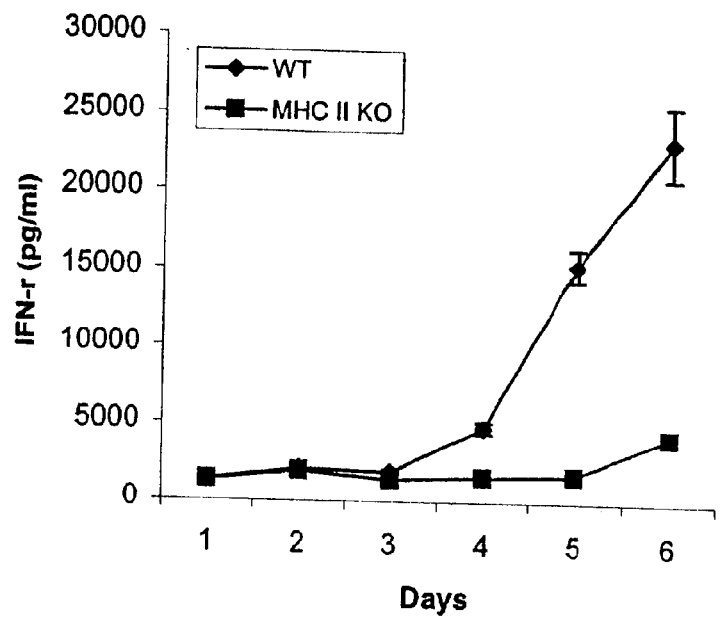
Figure 7B:
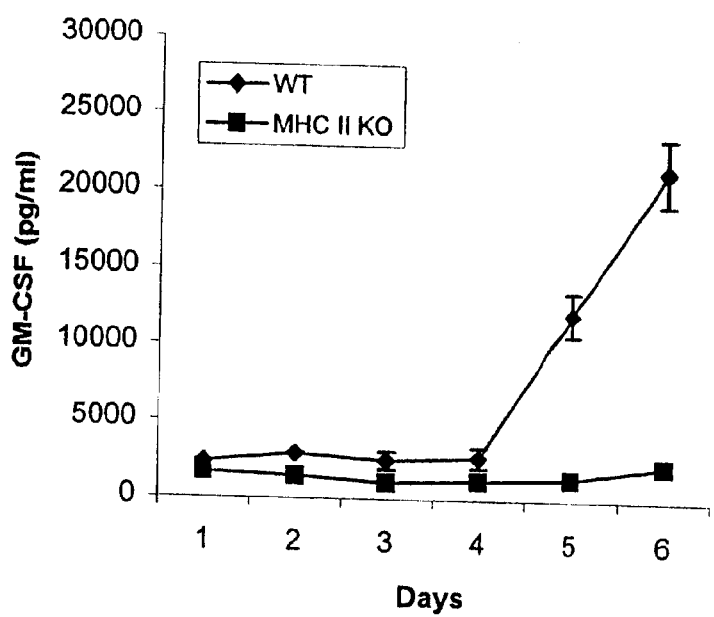

To further demonstrate MHC-II-restricted antigen presentation using the retrogen strategy, MHC-II knockout (KO) C57BL/6 mice, in which MHC-II antigen presentation by DCs was abolished, were used (Charles River, NY). DCs derived from wild-type (WT) or MHC-II KO mice were transduced with the HBe-retrogen and were then co-cultured with CD4+ T-cells obtained from WT mice at a ratio of 1:20. As shown in FIGS. 7A and 7B, only low levels of GM-CSF and IFN-γ were detected in the medium of the co-culture containing the transduced KO-DCs, and no apparent T-cell proliferation was observed. In contrast, when CD4+ T-cells were co-cultured with the transduced WT DCs for 5 days, the T-cells actively proliferated and high levels of GM-CSF and IFN-γ in the culture medium were detected (FIGS. 7A and 7B).

EXAMPLE 4

In vivo Induction of Helper and Cytotoxic T-cell, and B-cell Immune Response

The potential of the retrogen antigen presentation strategy was evaluated in vivo. Mice (C57BL/B6) were divided into four groups (4 to 6 mice/group) and each mouse was administered about a half a million of the DCs that were transduced with HBcAg, HBeAg, Fc, or HBe-retrogen in 0.2 ml PBS containing 50,000 U IL-2 (Chiron Corp. Emmeryville, Calif.) by intraperitoneal injection. At the different times post-final administration, the mice were sacrificed and peripheral blood, spleens and other organs were collected. T-cells were isolated for analysis using the CD4 or CD8+ T-cell enriching columns (R&D System, Minneapolis, Minn.).

Three months after the first injection, mice were sacrificed and the peripheral blood, spleen, and other tissue samples were collected. From gross examination, the lymph nodes in the peritoneal cavity were significantly enlarged in the mice administrated the HBe-retrogen-transduced DCs, while in normal mice and mice administrated other constructs, the lymph nodes were too small to be visible. Histologic examination also revealed active proliferation of T-cells and B-cells in the peritoneal lymph nodes of mice administered the HBe-retrogen-DCs.

EXAMPLE 5

Induction of $T_H1$ and $T_H2$ Helper T-Cells

Mice immunized as in Example 4 were used to determine the induction of $T_H1$ and $T_H2$ helper T-cells. -Skilled artisans are cognizant of the importance of determining the induction of $T_H1$ and $T_H2$ cells. It is well known that CD4+–T-cells perform the following functions: 1) they help B-cells develop into antibody producing plasma cells; 2) they help CD8+–T-cells to become activated cytotoxic T-cells; and 3) they effect delayed hypersensitivity. These functions are performed by two subpopulations of CD4 cells: $T_H1$ cells mediate delayed hypersensitivity and produce primarily IL-2 and gamma interferon (IFN-γ), whereas $T_H2$ cells perform the B-cell helper function and primarily produce IL-4 and IL-5.

CD4+–T-cells were isolated from the spleens of the immunized mice using an anti-CD4 column (R&D Systems, Minneapolis, Minn.) and these cells were then co-cultured with DCs of mice that were pulsed with a recombinant HBeAg protein. After only 2 days in co-culture of cells having a ratio of T-cells:DCs of 1000:1, the CD4+–T-cells from mice administered the HBe-retrogen-DCS actively proliferated. High levels of GM-CSF and IFN-γ (stimulate macrophages and CD8+–T-cells), as well as IL-4 and IL5 (stimulate B-cells), were detected in the co-culture medium. Anti-CD4 antibodies, but not anti-CD8 antibodies, dramatically blocked cytokine production in these co-cultured T-cells. In contrast, when the CD4+–T-cells obtained from mice immunized with HBeAg-, HBcAg- or Fc-DCs were co-cultured with HBeAg-DCs, only low levels of GM-CSF, IFN-γ, IL-4, and IL-5 were detected in the co-culture medium, and no active T-cell proliferation was observed. Since IL-4 and IL-5 are mainly produced by $T_H2$ and GM-CSF and IFN-γ by $T_H1$ cells, the results demonstrate that HBe-retrogen-transduced DCs effectively activate both $T_H1$ and $T_H2$ T-cells.

EXAMPLE 6

Induction of High Titers of Anti-HBeAg Antibodies

Figure 8:
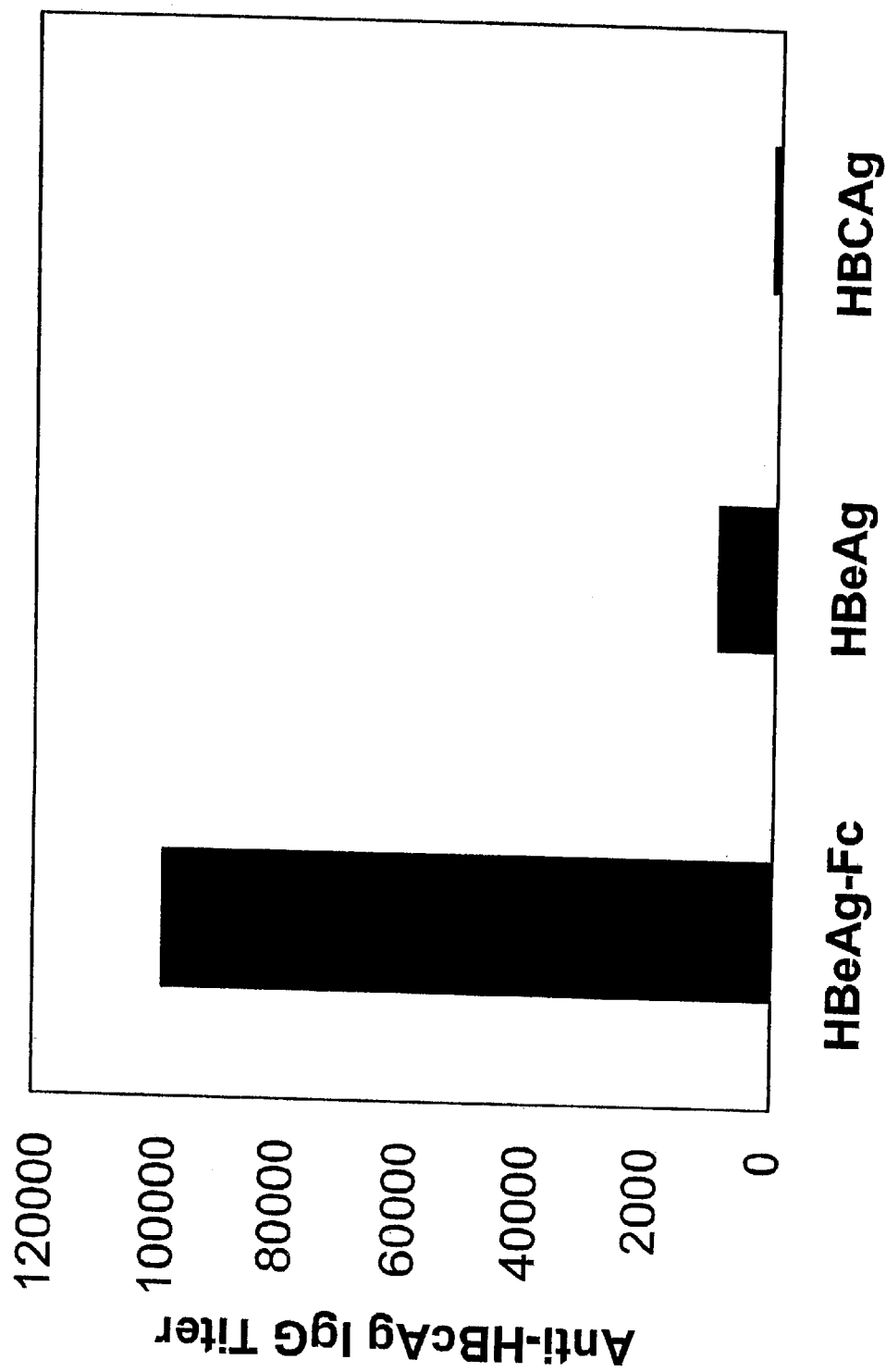

Mice were immunized as in Example 4 to determine the level of antibodies. Immunization of mice with HBe-retrogen-transduced DCs induced high-titer, long-lasting anti-HBe/cAg antibody responses in mice. As shown in FIG. 8, significantly higher titers of anti-HBeAg antibodies were detected in the sera of the mice administered the HBe-retrogen-transduced DCs than in the mice administered HBeAg-transduced DCs. The levels of anti-HBcAg antibodies in the sera of immunized mice were assessed using an ELISA. Briefly, microtitre plates coated with HBcAg recombinant proteins (50 ng/well) were incubated with serially diluted sera in a blocking buffer at 4° C. for 2 hours. Bound antibody was detected after incubation with peroxidase-conjugated antibodies to mouse IgG diluted in blocking buffer. A polyclonal anti-HBcAg antibody obtained from Chiron Corp. (Emmergyville, Calif.) was used as positive control, and normal mouse sera was used as a negative control. The antibody titer was defined as the highest dilution having an $OD_{450}$ value, which was two times above the negative level.

The fold increase of the antibody production observed may be due to the stronger activation of CD4+ helper T-cells. The significantly lower levels of anti-HBe/cAg antibodies in the sera of the mice immunized with HBcAg-transduced DCs may be due to the cytosolic location of HBcAg and lack of CD4+ T-cell activation. Thus, the HBe-retrogen is significantly superior to other HBeAg and HBcAg constructs for the induction of an antibody response in mammals immunized with the same. Taken together, the results of the mouse model study demonstrate that DCs transduced with HBe-retrogen induced vigorous CD4+– and CD8+–T-cell activation, as well as, B-cell activation.

EXAMPLE 7

Vector Construction of an Intracellular Tumor Antigen

Figure 9A:
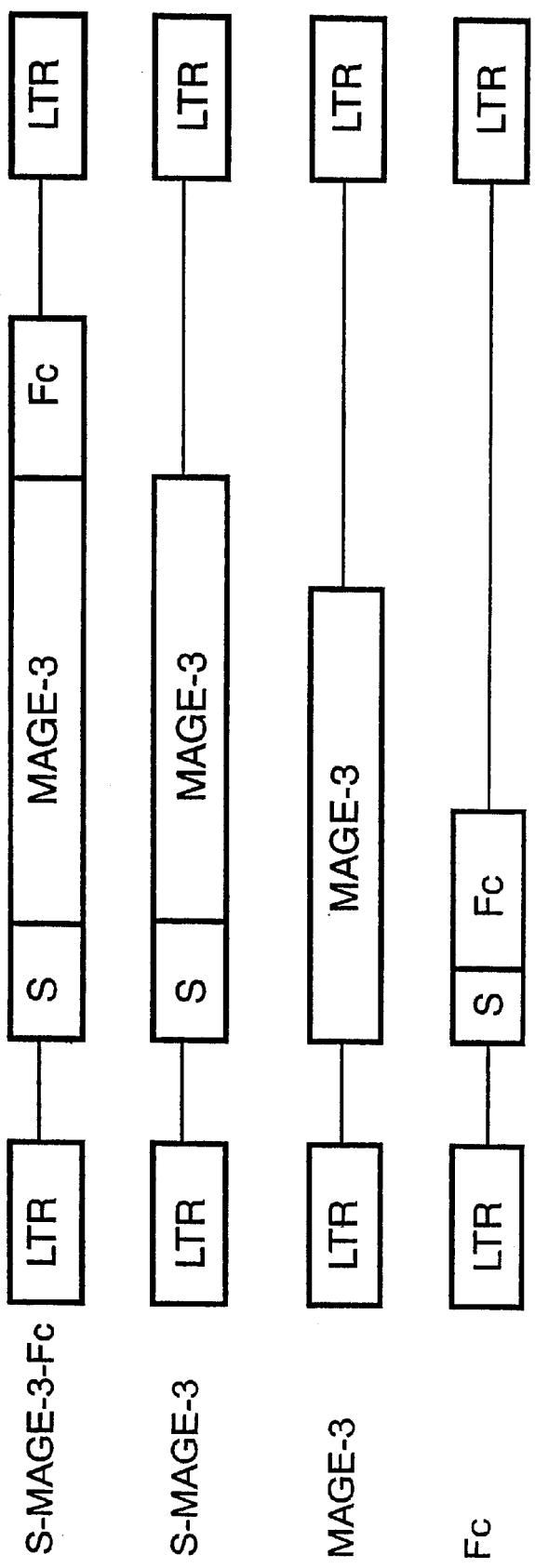

MAGE-3 is a cytosolic and nuclear protein lacking a targeting sequence for the endogenous MHC-II presentation pathway, which makes its presentation on MHC-II unlikely or difficult. Since there is no mouse homolog, a human MAGE-3 gene was linked to a signal leader sequence derived from a human chemokine RANTES gene to allow the secretion of MAGE-3. A plasmid encoding the full-length MAGE-3 gene was used as a template to amplify the MAGE-3 DNA with a pair of primers: 5'-primer (A): (SEQ. ID. No. 1) 5'-ACGCGTCGACATGCCTCTTGAGCAGAG GAGTCAG-3', corresponding to the polynucleotide sequence 1 to 24 of the MAGE-3 gene with an additional Sal I restriction site, and 3'-primer (B): (SEQ. ID. No. 2) 5'-CCGCTCGAGTCACTCTTCCCCCTCTCTCAAAAC-3', corresponding to the polynucleotide sequence 921 to 945 of the MAGE-3 with a Xho I site. The addition of the signal leader sequence derived from the human RANTES gene was generated by PCR amplification with a pair of primers: 5'-primer (C): (SEQ. ID. No. 3) 5'-ACGCGTCGACAT GAAGGTCTCCGCGGCAGCCCTCGCTGTCATCCT CATTGCTACTGCCCTCTGCGCTCCTGCATCTGCCAT GCCTCTTGAGCAGAGGAGTCAG-3', corresponding to the RANTES signal leader sequence and to the polynucleotide sequence 1 to 24 of the MAGE-3 gene with a Sal I site, and 3'-Primer-B. The signal-MAGE-3 fragment (s-MAGE-3) without the stop codon was generated by PCR with 5'-Primer-C and 3'-primer (D): (SEQ. ID. No. 4) 5'-ATAAG AATGCGGCCGCTCTCTTCCCCCTCTCTCAAAAC-3', corresponding to the polynucleotide sequence 921 to 942 of the MAGE-3 with a Not I site). DCs, the most potent APCs, express IgG Fc receptors (FcγRs), which mediate a privileged antigen internalization route for efficient MHC-II as well as MHC-I-restricted antigen. Hence, a Fc fragment cDNA derived from a human IgG1a that can efficiently bind to Fc receptors on murine DCs was fused in frame with the modified MAGE-3 gene to mediate MAGE-3 internalization by DCs (FIG. 9A). The secretory MAGE-3 fusion gene (s-MAGE-3-Fc) was then cloned into a murine retroviral vector pFB-Neo (Stratagene) (FIG. 9A). The human IgG cDNA Fc fragment was generated by PCR amplification with the plasmid pEE6/CLL-1 containing human IgG1a heavy chain cDNA as a template. The pair of primers for the PCR reaction are: 5'-primer (E), (SEQ. ID. No. 5) 5'-ATAAGCGGCCGCTAAAAC TCACACATGCCCA-3', corresponding to the polynucleotide sequence 785 to 802 of the heavy chain with an additional Not I site, and 3'-primer (F), (SEQ. ID. No. 6) 5'-CCGCTCGAGTCAT TTACCCGGAGACAGGGAGAG-3', corresponding to the polynucleotide sequence 1447 to 1468 of the heavy chain with a Xho I site. A murine retroviral vector, pFB-Neo (Stratagene), was used for this study. The retroviral vector s-MAGE-3-Fc was constructed by a three-piece ligation of the s-MAGE-3 fragment without the stop codon, Fc, and Sal I/Xho I-cut pFB-Neo. The retroviral vector s-MAGE-3 or MAGE-3 was constructed by inserting the s-MAGE-3 or MAGE-3 gene into Sal I/Xho I-cut pFB-Neo, respectively. To construct the IgG Fc expression vector, the human IgG Fc cDNA fragment was linked with an immunoglobulin heavy chain (VH) signal leader sequence by two PCR reactions. In the first PCR reaction, the IgG Fc cDNA was used as a template for the amplification with a pair of primers: 5' primer, (SEQ. ID. No. 7) 5'GCAGCTCCCAGATGGGTC-CTGTCCAAAACTCACACATGCCCACCGTG CCCAGCAC-3', corresponding to the polynucleotide sequence 785 to 815 of the heavy chain and a partial VH-leader sequence, and 3'-Primer F (SEQ. ID. No. 6). The second PCR utilizing the product of the first PCR as a template was carried out with a pair of primers: 5' primer, (SEQ. ID. No. 8) 5'-ACGCGTCGACATG GGAACATCTG TG GTTCTTCCTTCTCCTGGTGGCAGCTCCCA GATGGGTCCTGTCC-3', corresponding to the N-terminal polynucleotide sequence of the VH-secretion signal leader sequence with an additional Sal I site, and 3'-Primer F (SEQ. ID. No. 6). The Fc cDNA with a signal leader sequence was then cloned into the retroviral vector. The expression vector pcDNA3.1-MAGE-3 was constructed by inserting the MAGE-3 into the XhoI/XbaI-cut pcDNA3.1 (Invitrogen). Several control retroviral vectors expressing a native, intracellular MAGE-3, secretory s-MAGE-3, or secretory Fc fragment were also constructed (FIG. 9A). Each resultant vector was identified by restriction enzyme analysis and confirmed by DNA sequencing.

EXAMPLE 8

Production of Retroviruses and Transduction of Bone Marrow-Derived DC

Retroviral vectors were produced by transient transfection. Packaging cells (PA317) were cultured in 100-mm culture dishes with DMEM containing 10% heat-inactivated FBS (Gibco-BRL) and transfected with 10–15 μg of retroviral vector plasmids (from Example 7, i.e., intracellular MAGE-3, secretory s-MAGE-3, or secretory Fc fragment) that were prepared by using endotoxin-free QIAGEN kits by Lipofectin (Gibco-BRL). After overnight incubation, the medium was replaced with DMEM containing 5% FBS. After 48 hours, the culture medium containing recombinant retroviruses was harvested and filtered (0.22 μm), as described previously (Chen et al., 1997). To generate DCs, bone marrow cells were flushed from the bones of mouse limbs, passed through a nylon mesh, and depleted of red cells with ammonium chloride. After extensive washing with RPMI-1640, the cells were incubated with rabbit complements (Calbiochem) and a cocktail of monoclonal antibodies consisting of anti-CD4, anti-CD8, anti-CD45R/B220, and anti-MHC-II (PharMingen and BioSource International) in RPMI-1640 at 37° C. for 40–60 min. After extensive washing with RPMI-1640, cells ($5\times10^5$ cells/ml) in RPMI-1640 supplemented with 6% FBS, 80 ng mSCF/ml (R&D Systems), and 20 Units (U) mIL-6/ml (BioSource International) were plated in 12-well culture plates (2.5 ml/well), incubated at 37° C., 5% $CO_2$ overnight, and then referred with fresh medium. After 48-hour incubation, the cells were spun down, resuspended in 1.5 ml of the retrovirus supernatants, placed onto 24-well culture plates coated with Retronectin (PanVera) at a concentration of 10–20 ng/ml, and incubated at 37° C., 5% $CO_2$ for 3–4 hour. The supernatants were then replaced with 1.5 ml of RPMI-1640 supplemented with 5% FBS, 10 ng murine stem cell factor (mSCF)/ml, 60 ng mGM-CSF/ml (BioSource International) and 100 U mIL-4/ml (R & D Systems) overnight. The transduction procedure was repeated 2–3 times and about 30% of BM cells were usually transduced by this procedure. After the final transduction, the cells were washed cultured in Opti-MEM (Gibco-B containing mGM-CSF and mIL-4 for several days to allow further DC differentiation. DCs were further enriched with a 50% FCS-RPMI-1640 sedimentation procedure, as described previously (Inaba et al., 1992).

Figure 9B:
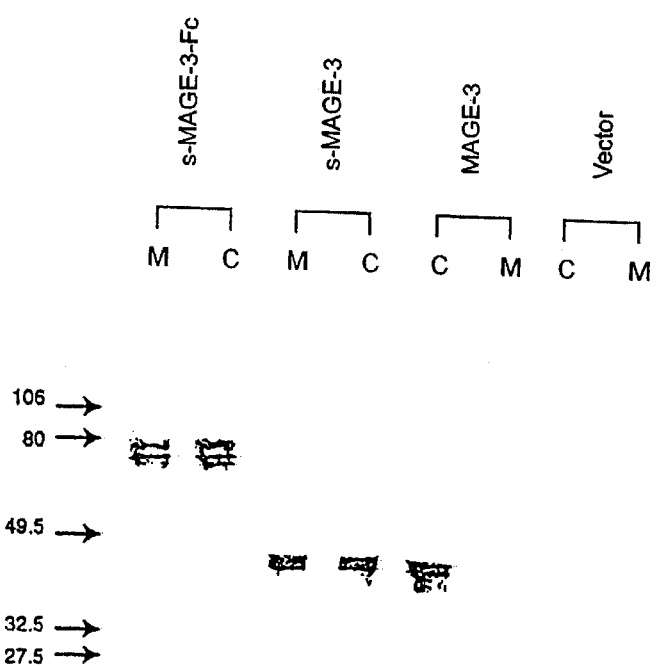
Figure 9C:
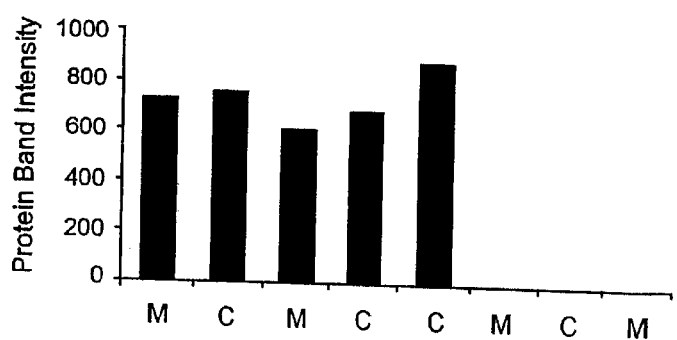

After several days of culture, a substantial fraction of the cells showed distinct DC morphology. The s-MAGE-3-Fc, s-MAGE-3, MAGE-3, or Fc gene in the transduced DCs was transcribed, as demonstrated by reverse transcription (RT)-PCR assays. Quantitative Western blotting analysis was used to demonstrate protein expression and secretion by the constructs in transduced DCs. Briefly, the transduced DCs were lysed with a buffer (Boehringer Mannheim) (10 mM Tris 150 mM NaCl (pH 7.4), 1% TX-100 (Sigma), 0.5 mM PMSF, and protease inhibitor cocktail tablets) on ice for 10 min. Cell lysates and culture media were then precipitated with a rabbit polyclonal antibody against MAGE-3, followed by incubation with Protein A-Sepharose (Sigma). The precipitates were then resuspended in 20 µl loading buffer. The protein samples (20 µl) were loaded onto a 10% SDS-PAGE gel and transferred to a Hybond PVDF membrane (Amersham Pharmacial Biotech), which was blocked by overnight incubation in PBS (pH7.5) containing 5% non-fat dried milk (Carnation) and 0.1% (v/v) Tween-20 (Fisher Scientific) at 4° C. After washing with a buffer (PBS containing 0.1% (v/v) Tween-20), the membrane was incubated with a mouse monoclonal antibody against MAGE-3 diluted in a PBS buffer containing 2.5% non-fat milk and 0.1% Tween-20 (1:400) at room temperature for 1 hour. After washing, the membrane was then incubated with a horseradish peroxidase (HRP) labeled anti-mouse IgG (Amersham Pharmacia Biotech) in the buffer (1:10,000) at room temperature for 1 hour. After a final wash, the membrane was visualized with an ECL-Plus chemiluminescent detection kit (Amersham Pharmacia Biotech) and exposed on a Kodak film. Protein band intensity of the Western blot on the film was determined and analyzed by a Phosphorimager (Molecular Dynamics) with an Image-Quant software 1.2 version. It was found that the s-MAGE-3-Fc and s-MAGE-3 proteins were efficiently produced and secreted from DCs, while MAGE-3 was retained intracellularly (FIGS. 9B and 9C). Comparable levels of s-MAGE-3-Fc, s-MAGE-3, and MAGE-3 proteins were expressed in the transduced DCs.

EXAMPLE 9

Interaction of Fc on DC

Figure 9D:
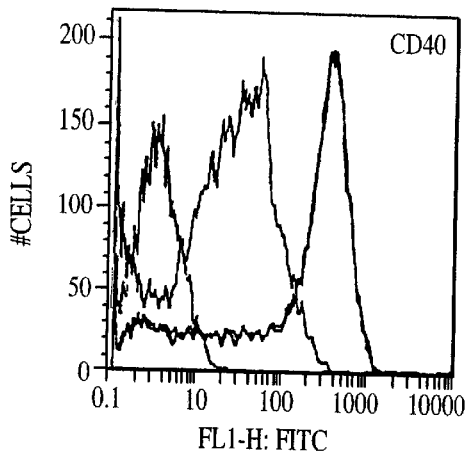
Figure 9E:
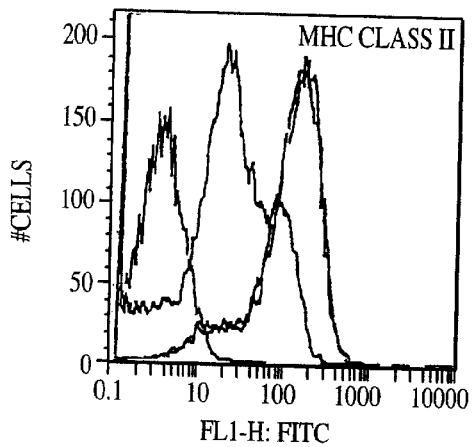
Figure 9F:
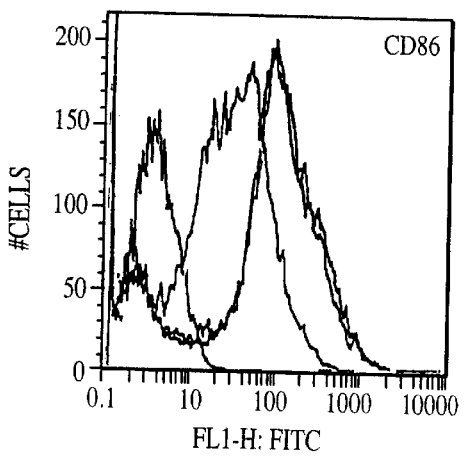
Figure 10A:
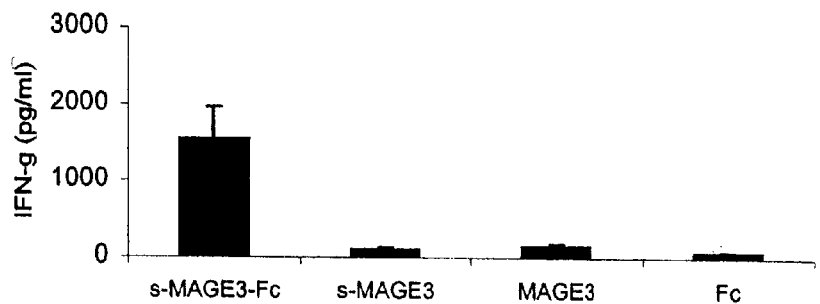
Figure 10B:
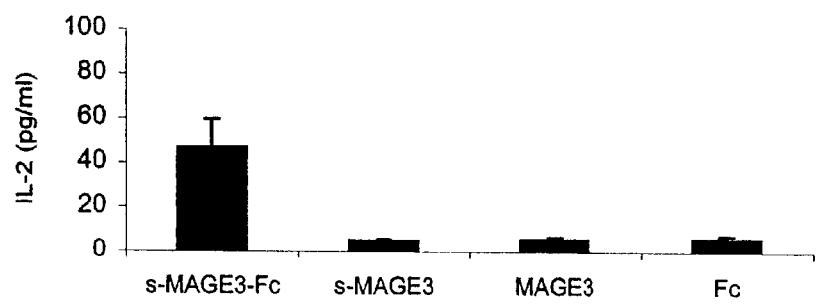
Figure 10C:
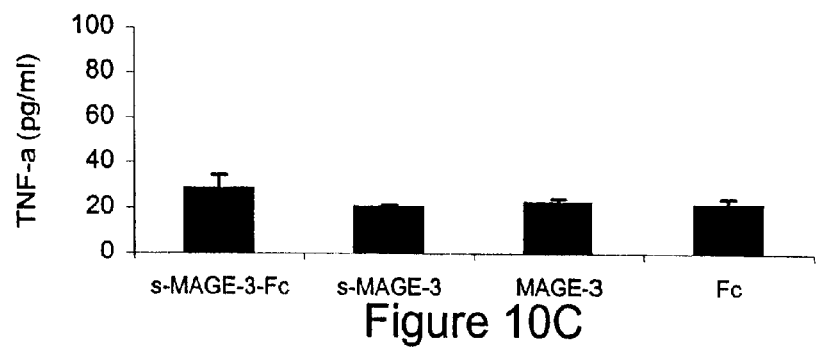
Figure 10D:
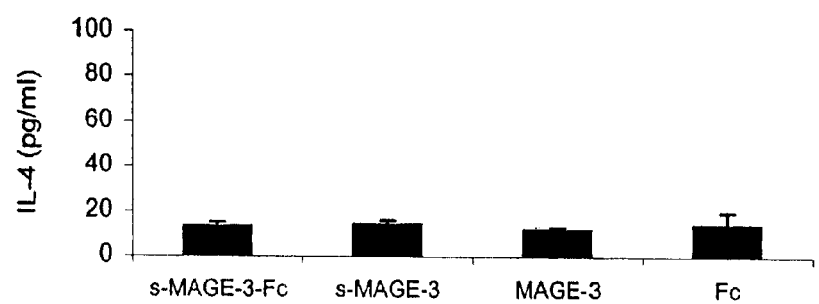

Interaction of Fc with FcγRs on DCs triggers cell activation, causing the up-regulation of cell surface molecules involved in antigen presentation. Surface markers were examined to evaluate whether the expression of s-MAGE3-Fc in the transduced DCs could induce DC activation. Surface markers of DCs transduced with s-MAGE-3-Fc, s-MAGE-3, or vector, were measured by flow cytometric assays. Briefly, the DCs were pre-incubated with an anti-CD16/CD32 antibody (2.4G2, PharMingen) for blocking FcγRs at 4° C. for 30–60 min. The DCs were then incubated with primary antibodies at 4° C. for 30 min, followed by incubation with an anti-mouse or -rabbit IgG-FITC conjugate. After extensive washing, the DCs were analyzed by a FACScan (Becton Dickinson) with CellQuest software. As shown in FIGS. 9D, 9E and 9F, higher levels of MHC class-II, CD40, and CD86 were expressed on DCs derived from BM cells transduced with s-MAGE-3-Fc and on DCs in the presence of LPS than on DCs transduced with s-MAGE-3 or vector control. These results suggest that the secretion and subsequent interaction of the fusion protein Fc with FcγR activate DCs.

EXAMPLE 10

Induction of Potent $T_H1$ in vivo

To evaluate whether the secretion and subsequent internalization of MAGE-3 can enhance the immunogenicity of this antigen in vivo, DCs were transduced with s-MAGE-3-Fc, s-MAGE-3, MAGE-3, or Fc by retroviral vectors, and then administered i.v. once into C57BL/6 mice (0.5–1×10$^5$ DC in 30 µl PBS containing 50,000 u2135 IL2(chiron) per mouse). Four to six weeks after immunization, the mice were sacrificed and peripheral bloods, spleens, and other tissue samples were collected. Lymph nodes were substantially enlarged in the mice immunized with s-MAGE-3-Fc-DCs, reminiscent of pathogen infection, but not in the mice administered with DCs transduced with s-MAGE-3, MAGE-3, or Fc.

Figure 11A:
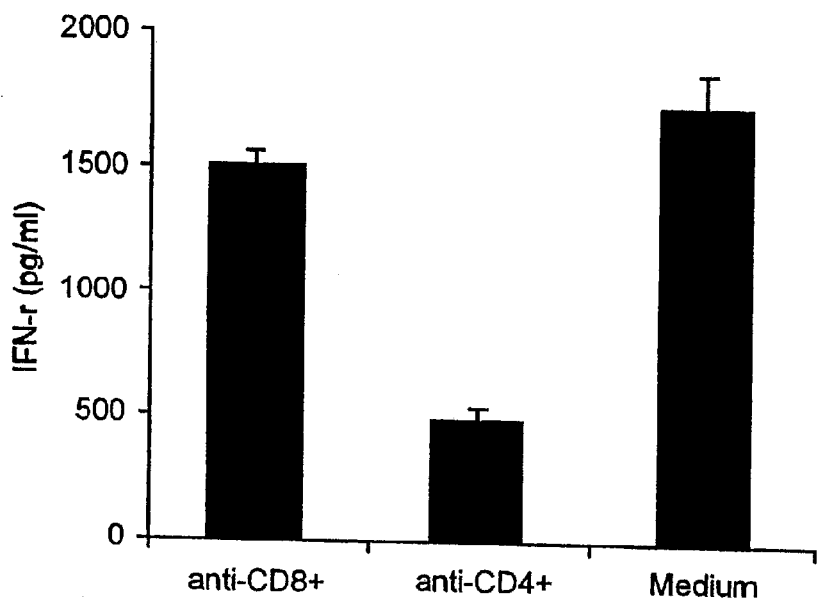
Figure 11B:
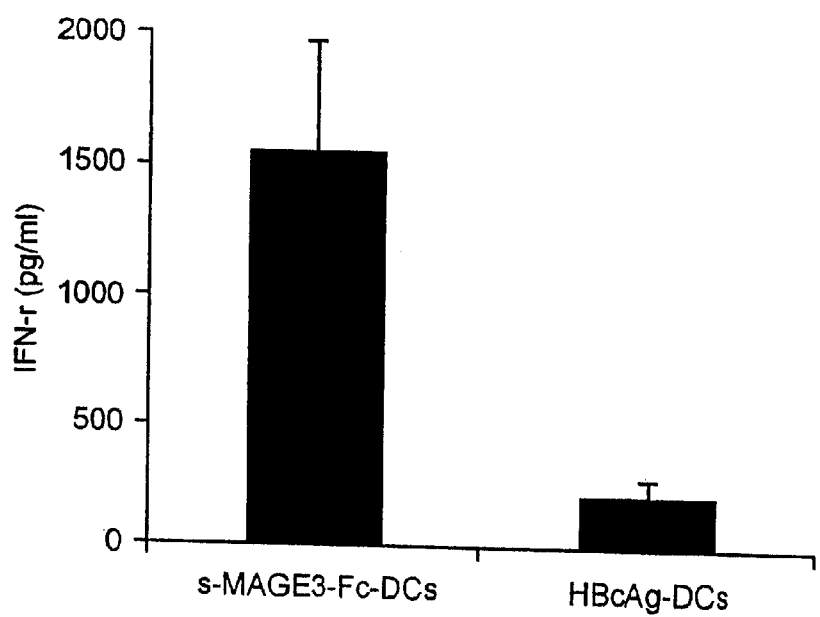
Figure 12A:
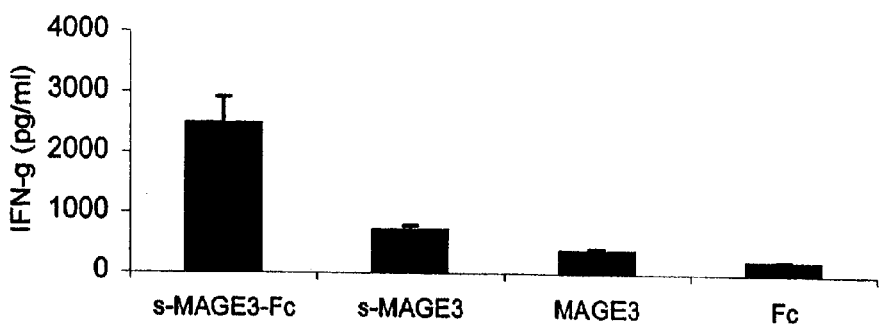
Figure 12B:
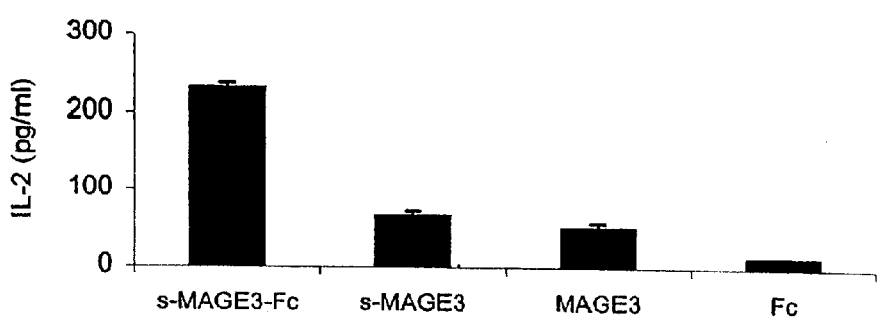
Figure 12C:
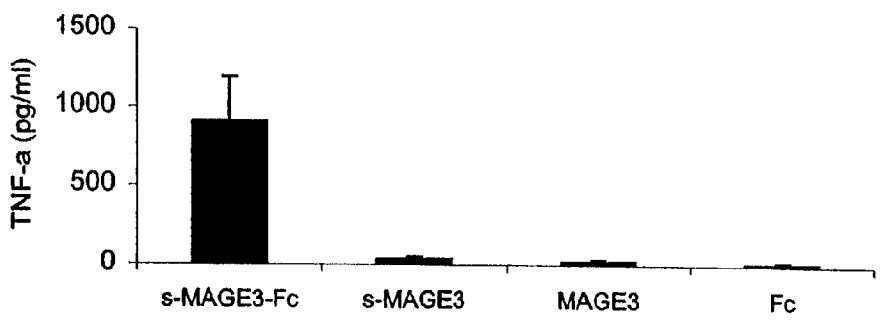
Figure 12D:
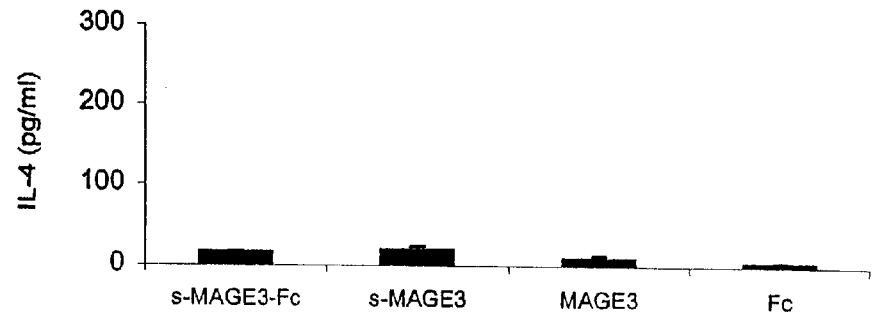

To determine if immunization with transduced DCs can induce CD4+ helper T cell responses, CD4+ T-cells from splenocytes of the immunized mice were isolated and then co-cultured them with bone-marrow (BM)-derived DCs transduced with s-MAGE-3-Fc. Briefly, CD4+ or CD8+ T-cells were isolated from spleen suspensions with CD4+ or CD8+ T cell enrichment columns (R & D Systems) and then cultured in RPMI-1640 supplemented with 10% FBS for 24 to 48 hours before further analysis. Draining lymph nodes from immunized mice were digested with a cocktail of 0.1% DNase I (fraction IX, Sigma) and 1 mg/ml collagenase (Roche Molecular Biochemicals) at 37° C. for 40–60 min. DCs were positively isolated from the cell suspensions of lymph nodes or spleens with anti-CD11c (N418) Micro-Beads (Miltenyi Biotec Inc) for further study. During two weeks of co-culture with different ratios of CD4+ T-cells vs DCs, the CD4+ T-cells from mice immunized with s-MAGE-3-DCs, MAGE-3-DCs, or Fc-DCs did not actively proliferate, and only low levels of IL-2, IFN-γ, TNF-A, and IL-4 were detected in the co-culture media (FIGS. 10A, 10B, 10C and 10D). CD4+ T cells from immunized mice were co-cultured with DCs at a rate of 1000:1 (T cell:DC, $2\times10^5:2\times10^2$) for various times. Supernatants of the co-cultures were harvested and subsequently assayed for cytokine concentrations by ELISA (PharMingen) according to the manufacturer's instructions (PharMingen). In contrast, in the co-cultures with CD4+ T-cells from mice immunized with s-MAGE-3-Fc-DCs, high levels of IL-2 and IFN-γ were detected in the co-culture media after only 48-hour of co-culture even at a 1:1000 (DC:T-cell) ratio. Anti-CD4, but not anti-CD8 antibodies, blocked the cytokine production by the co-cultured cells (FIG. 11A). Repeated experiments showed similar results. To further determine the specificity of the T-cell responses, BM-derived DCs transduced with a retroviral vector expressing an irrelevant hepatitis B virus core antigen (HBcAg) were co-cultured with CD4+ T cells from s-MAGE-3-Fc-DCs-immunized mice. Only low levels of IFN-γ, and other cytokines were detected in the co-culture media (FIG. 11B). Furthermore, DCs from the lymph nodes of mice six weeks after immunization were isolated with anti-CD11c microbeads (Miltenyi Biotec, Inc.) and co-cultured with CD4+ T cells from the same immunized mice. As shown in FIGS. 12A, 12B, 12C, and 12D, high levels of IL-2, IFN-γ, and TNF-α were only detected in the co-cultures of the cells from s-MAGE-3-Fc-DCs-immunized mice. These results indicate that the DCs transduced with s-MAGE-3-Fc can home to lymphoid organs or tissues, and activate Th1 responses more efficiently than do DCs transduced with the native MAGE-3 or s-MAGE-3.

EXAMPLE 11

Induction of CTLs in vivo

The JAM or "just another method" test was performed to determine whether immunization with s-MAGE-3-Fc-DCs can induce strong CTL responses. The JAM test was used to measure cytotoxic activities. Briefly, mice were sacrificed at different times after immunization and a single-cell suspension of splenocytes was cultured in RPMI 1640 10% FBS. A total of $4 \times 10^6$ splenocytes was restimulated with $8 \times 10^4$ γ-irradiated (10,000 rad) syngeneic EL4-MAGE-3 cells or EL4-HBcAg cells/2 ml in 24-well plates (Costar) for 4–6 days in 5% $CO_2$ at 37° C., pooled, and then resuspended to $1 \times 10^7$ cells/ml. To label the target cells, $^3$H-thymidine was added into $5 \times 10^5$/ml EL4-MAGE-3 or EL4-HBcAg cells at a final concentration of 2 μCi/ml. After 6 hour incubation, the cells were gently washed once with PBS and resuspended in the culture medium ($1 \times 10^5$ cells/ml). Different numbers of effector cells were then co-cultured with a constant number of target cells ($1 \times 10^4$/well) in 96-well round-bottomed plates (200 μl/well) for 4 hour at 37° C., after which the cells and their media were then aspirated onto fiber glass filters (Filter Mate Harvester, Packard) that were then extensively washed with water. After the filters were dried and placed onto 96-well plates, 25 μl MicroScint 20 (Packard) were added to each well. The plates were counted in a TopCount NXT Microplate Scintillation and Luminescence Counter (Packard). In some experiments, the restimulated effector cell populations were incubated with the anti-CD4 or anti-CD8 antibodies (30 μl/well, PharMingen) for 30–60 min to deplete CD4+ or CD8+ T-cells before cytotoxicity assays. The percent of specific killing was defined as: (Target cell DNA retained in the absence of T-cells (spontaneous)—Target cell DNA retained in the presence of T-cells)/spontaneous DNA retained ×100. The value of total $^3$H-thymidine incorporation is often similar to the spontaneous retention. Splenocytes from immunized mice were restimulated in vitro in RPMI-1640, 10% FBS with syngeneic cells EL4-MAGE-3, and then co-cultivated with $^3$H-thymidine labeled EL4-MAGE-3 cells at various effector/target ratios to measure the specific killing. EL4-MAGE-3 cells were established by transfection with the MAGE-3 expression vector (pcDNA3.1-MAGE-3) and Zeocin (Invitrogen) selection, and shown to express MAGE-3 by PCR and immunoprecipitation assays.

Figure 13:
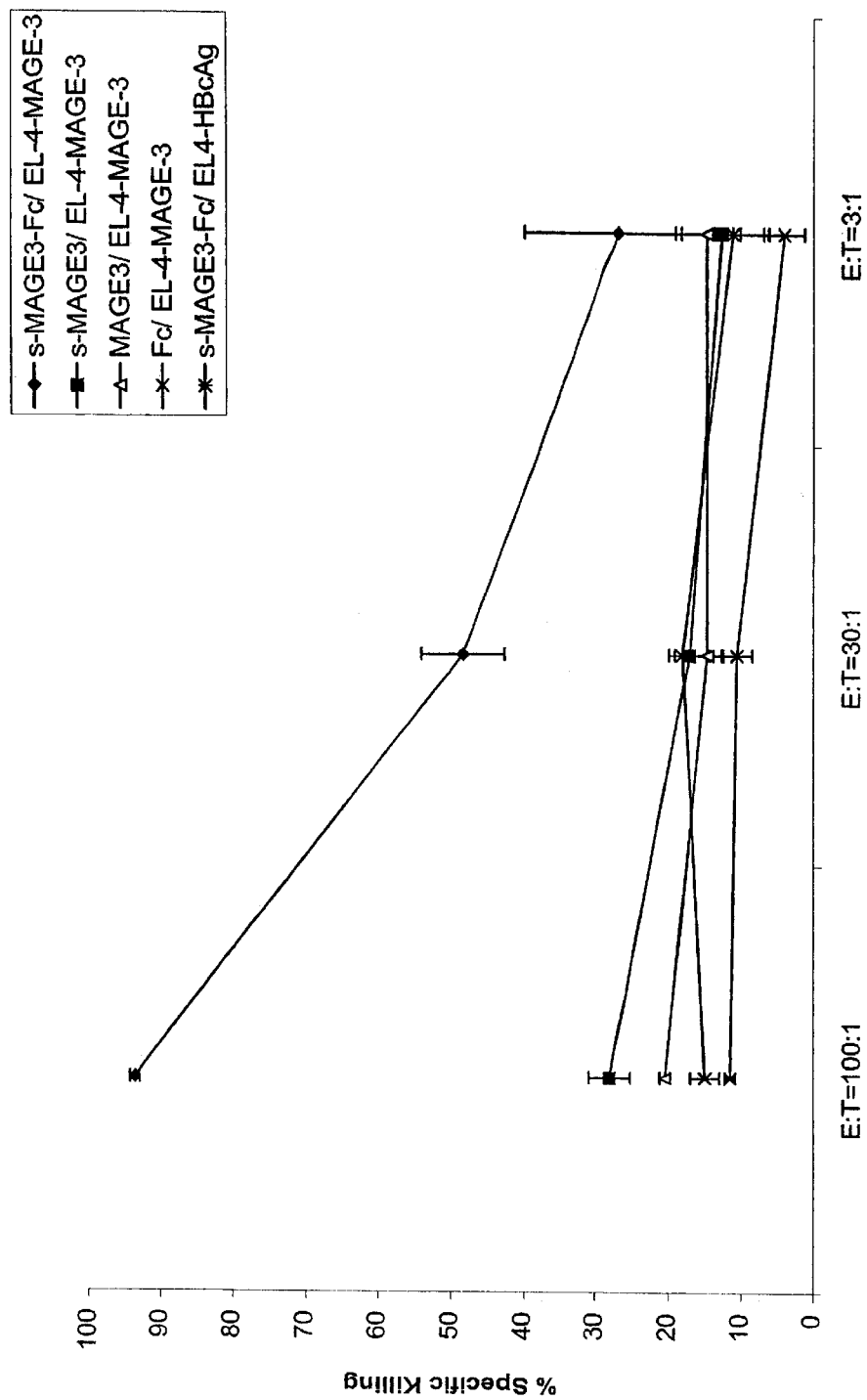
FIG. 13 shows the in vivo induction of cytotoxicity responses from splenocytes isolated from immunized mice which were re-stimulated (E) in vitro with irradiated EL4-MAGE-3 cells and co-cultured with the $^3$H-thymidine labeled target cells, EL4-MAGE-3 or EL4-HBcAg (control) (T).

Splenocytes from mice immunized with s-MAGE-3-Fc-DCs killed target cells much more efficiently than those from mice immunized with s-MAGE-3, MAGE-3, or Fc (FIG. 13). The specificity of killing was further demonstrated by the inability of the splenocytes of s-MAGE-3-Fc-DCs-immunized mice to kill EL4-HBcAg cells that express the irrelevant HBcAg (FIG. 13), and by the inhibition of killing with the anti-CD8, but not the anti-CD4 antibody. Thus, these results demonstrate the superior ability of s-MAGE-3-Fc-DCs to induce CTL responses, due to the enhanced $T_H1$ and cross-priming of receptor-mediated antigen internalization.

EXAMPLE 12

Induction of Antibody

Since antibodies can also play a role in antitumor immunity, anti-MAGE-3 antibody titers in the sera of immunized mice (similar to Example 10) were measured by ELISA. Anti-MAGE-3 antibodies in the sera of immunized mice were detected by ELISA. Briefly, microtiter plates (Dynatech) coated with a recombinant MAGE-3 proteins (50 ng each/well) were incubated with serially diluted sera in a blocking buffer (KPL, Gaithersburg, Md.) at room temperature for 2 hour. Bound antibody was detected after incubation with a peroxidase-conjugated antibody against mouse IgG (Sigma) diluted in the blocking buffer. A monoclonal antibody against MAGE-3 was used as a positive control and normal mouse sera as a negative control. The antibody titer was defined as the highest dilution with an $OD_{A450}$ greater than 0.2. The background $OD_{A450}$ of normal mouse sera was lower than 0.1. Anti-MAGE-3 antibodies were induced 2 weeks after DC immunization and reached the peak 4–6 weeks after immunization.

Figure 14:
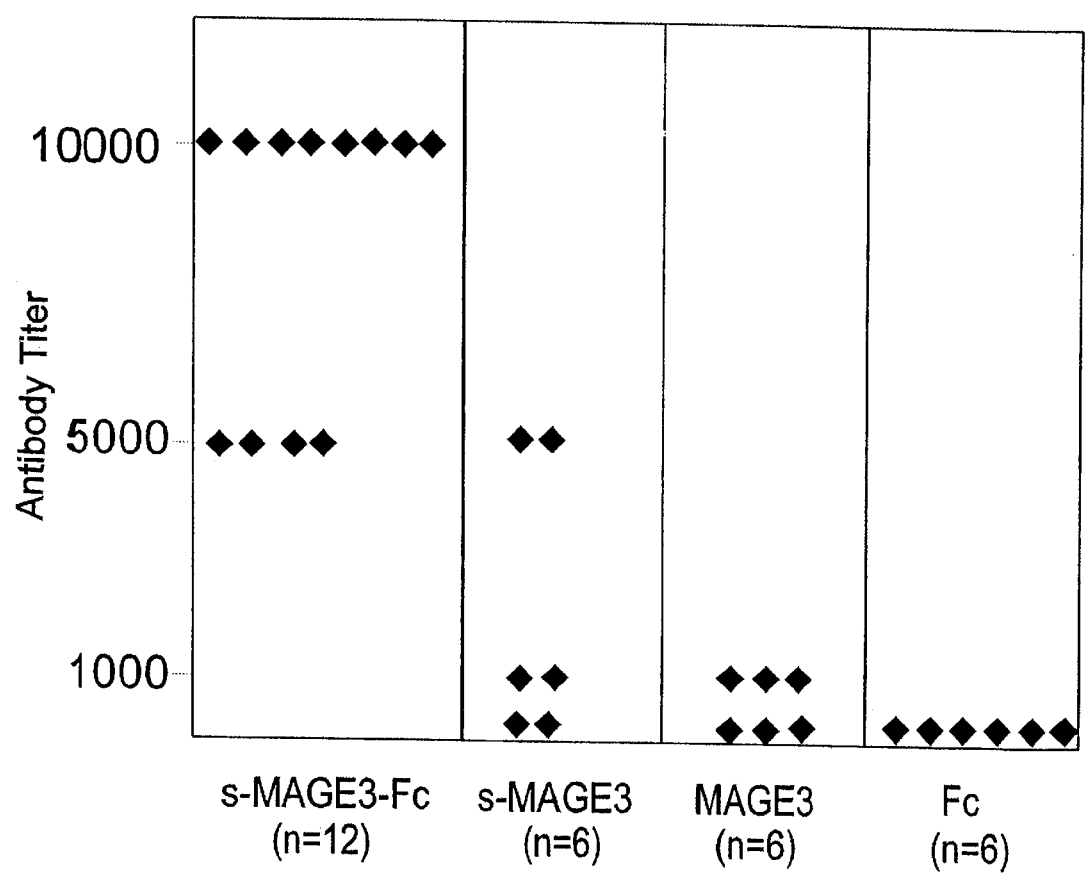
FIG. 14 shows the induction of antibody responses 6 weeks after dendritic cell immunization.

As shown in FIG. 14, significantly higher titers of anti-MAGE-3 antibodies were detected in the sera of s-MAGE-3-Fc-DC immunized mice than in mice immunized with s-MAGE-3-DCs or MAGE-3-DCs. The specificity of the antibody responses was demonstrated by the lack of antibody against the irrelevant HBcAg in the immunized mice. Taken together, the findings indicate that s-MAGE-3-Fc-DCs are superior to MAGE-3-DCs or s-MAGE-3-DCs in inducing CD4+ Th, CD8+ CTL, as well as B-cell responses.

EXAMPLE 13

Enhanced Interaction of Helper T-Cells

Figure 15:
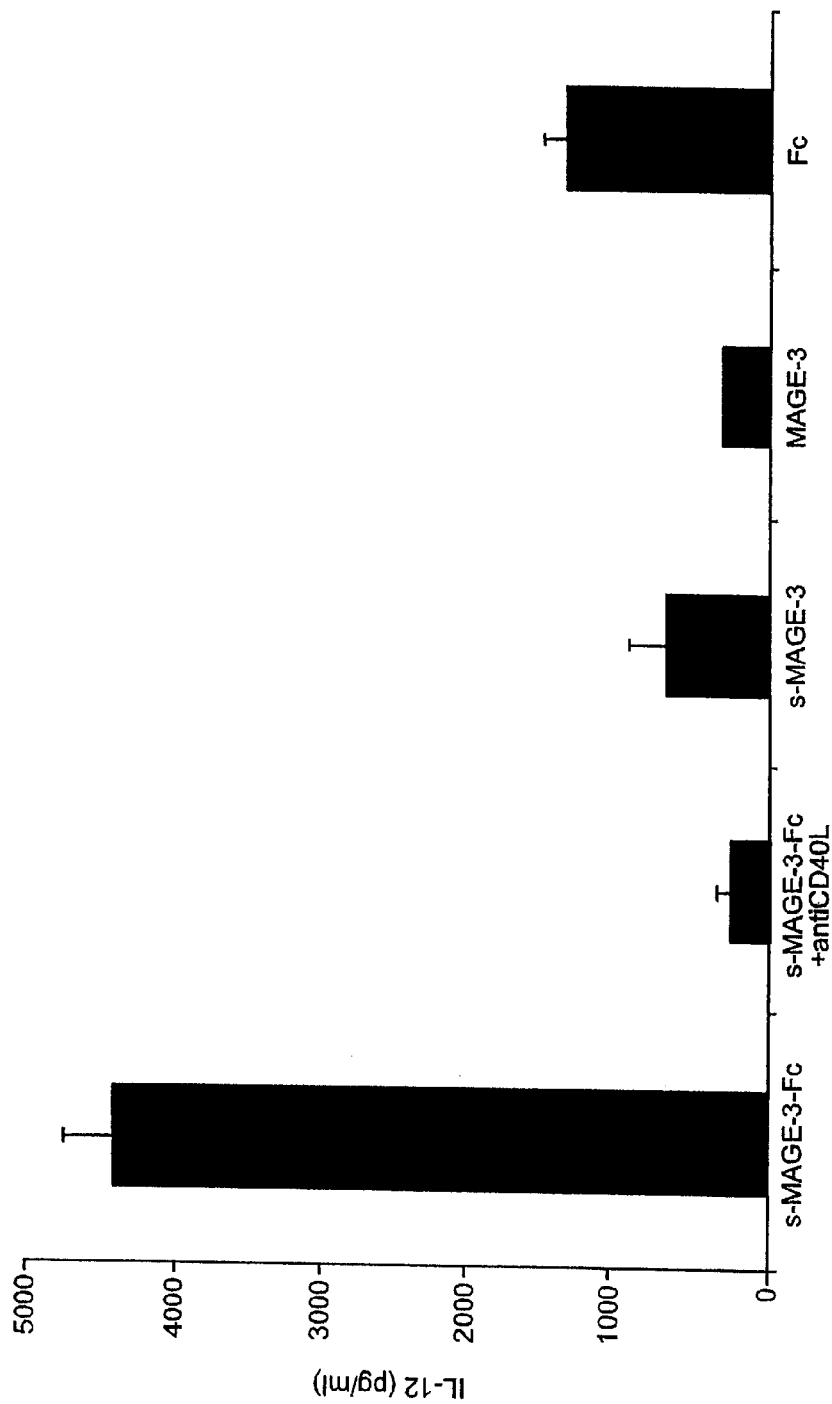
FIG. 15 shows the enhanced interaction of T-cells with s-MAGE-3-Fc-dendritic cells by measuring the IL-12 levels in the co-culture in the presence or absence of an anti-CD40L antibody (MR1, PharMingen) measured by ELISA.

Primed CD4+ TH cells that recognize their specific peptides in the context of MHC-II on DCs greatly increase their interaction with conditioned DCs. This interaction via CD40-CD40L can trigger DC production of IL-12 and is critical for generating T-cell helper for CTL responses. To test if this approach can enhance CD4+ $T_H$ interaction with s-MAGE-3-Fc-DCs, IL-12 production by transduced DCs in co-culture with primed CD4+ T-cells was measured. Primed CD4+ T-cells were isolated from mice immunized with s-MAGE-3-Fc-DCs and then co-cultured with BM-derived DCs transduced with s-MAGE-3-Fc, s-MAGE-3, MAGE-3, or Fc. As shown in FIG. 15, a significant increase in IL-12 production was observed in the CD4+ T-cell co-culture with s-MAGE-3-Fc-DCs, but not in the co-cultures with s-MAGE-3-DCs or MAGE-3-DCs. The IL-12 production by s-MAGE-3-Fc-DCs was inhibited by blocking with CD40L on the primed CD4+ T-cells. The expression of Fc in DCs also non-specifically enhanced IL-12 production to a lesser degree. These results, together with the in vivo results of Example 10, 11, and 12 data, indicate that the secretion and subsequent FcγRs-mediated -internalization of MAGE-3 lead to the cross-presentation of MAGE-3 on DCs for the induction of $T_H1$ and CTL responses.

EXAMPLE 14

Protective Immunity Induced by s-MAGE-3-Fc-DCs

To examine if the enhanced anti-MAGE-3 immune responses could lead to effective anti-tumor immunity, challenge experiments were performed. The EL4-MAGE-3 cell line was derived from the parental tumor EL-4 line that grows rapidly in syngeneic mice and used for challenge experiments. When intradermally implanted into syngeneic C57BL/6 mice, EL4-MAGE-3 cells (0.5 to $1 \times 10^6$ cells) showed aggressive tumor growth similar to that of parental EL-4 cells, producing visible tumors in mice by only 3–5 days after inoculation and resulting in mouse death usually within one month after inoculation. To test the ability of s-MAGE-3-Fc-DCs to inhibit EL4-MAGE-3 tumor growth, mice were immunized i.v. twice (7 day interval) with $1 \times 10^5$ DCs tranduced with s-MAGE-3-Fc, s-MAGE-3, MAGE-3 or Fc, followed by challenge with the EL4-MAGE-3 cells ($1 \times 10^6$). C57BL/6 mice were immunized by i.v. injection with $1 \times 10^5$ transduced DCs on day 0 and day 7, and then intradermally challenged with $1 \times 10^6$ exponentially growing EL4-MAGE-3 or EL4-HBcAg cells 1 week after the second immunization. Tumor sizes were measured every 2 to 3 days, with tumor volumes calculated as follows: (longest diameter)×(shortest diameter)$^2$.

As shown in FIG. 16A, tumor growth was inhibited to a much greater extent in mice immunized with s-MAGE-3-Fc-DCs, although immunization with s-MAGE-3-DCs, MAGE-3-DCs, or even Fc-DCs (a non-specific immune stimulator) did confer some degree of protection. The potency of the antitumor activity shown by these constructs correlated with their abilities to induce immune responses. Consistently, the mice immunized with s-MAGE-3-Fc-DCs survived considerably longer than mice immunized with other vector-transduced DCs (FIG. 16B). The antitumor activity induced by the s-MAGE-3-Fc-DCs was specific, since mice immunized with s-MAGE-3-Fc-DCs and challenged with wild type EL4 or EL4-HBcAg cells also developed lethal tumors and died within one month. S-MAGE-3-Fc-DCs also partially inhibited the growth of established EL4-MAGE-3 tumors in mice, even though the immune system may not have sufficient response time to effectively control rapidly lethal tumor growth in this model.

EXAMPLE 15

Construction of an HBe Antigen in a Mammalian Expression Vector

A plasmid encoding the full-length HBV (adw subtype) genome was obtained from the American Type Culture Collection (ATCC). The HBV precore/core gene was found to contain a single base pair deletion, which causes a frameshift at codon 79, resulting in two consecutive stop codons at 84 and 85. This gene was repaired by inserting the deleted base using PCR mutagenesis and confirmed by DNA sequencing. The full-length HBeAg gene was generated by PCR amplification of the repaired HBV genome with a pair of primers (5'-primer (P-A): (SEQ. ID. No. 9) 5'-TTAA GCTTATGCAACTTTTTCACCTCTGCCTAATC-3', corresponding to the polynucleotide sequence 1904 to 2020 of the HBV genome with an additional HindIII restriction site, and 3'-primer (P-B): (SEQ. ID. No. 10) 5'-TTTCTAGA ATCGATTAACATTGAGATTCCCGAGA-3', corresponding to the polynucleotide sequence 2437 to 2457 of the HBV genome with additional Xba I and Cla I sites). The truncated HBeAg gene with the deletion of the arginine-rich, C'-terminal sequence of HBeAg (aa 150–185) that is cleaved during viral infection, was generated by PCR amplification with a pair of primers (5'-primer: P-A (SEQ. ID. No. 9) and 3 -primer (SEQ. ID. No. 11) 5'-GTGCGGCCGC TCTAACAACAGTAGTTTCCGGAAGTGT-3', corresponding to the polynucleotide sequence 2324 to 2350 of the HBV genome with an additional Not I restriction site). The full-length HBcAg gene was generated by PCR amplification with a pair of primers (5'-primer: (SEQ. ID. No. 12) 5'-TTAAGCTTATGGACATTGACCCTTATAAAGAATTT GGAGC-3', corresponding to the polynucleotide sequence 1901 to 1932 of the HBV genome with an additional Hind III restriction site, and the primer P-B (SEQ. ID. No. 10)). The human IgG cDNA Fc fragment was generated by PCR amplification with the plasmid pEE6/CLL-1 containing human IgG heavy chain cDNA as a template. The pair of primers for the PCR reaction are: 5'-primer ( SEQ. ID. No. 13) 5'-ATAAGCGGCCGCTAAAACTCACACATGCCCA-3', corresponding to the polynucleotide sequence 785 to 802 of the heavy chain with an additional Not I site, and 3'-primer (P-C) (SEQ. ID. No. 14) 5'-TATTCTA GATCGATCACTCATTTACCCGGAGACAGG-3', corresponding to the polynucleotide sequence 1447 to 1468 of the heavy chain with a Cla I site. pRc/CMV vector (Invitrogen) was used for this study. The expression vector HBe-Fc, which expresses the secretory HBe-Fc fusion protein consisting of the truncated HBeAg fused in-frame to the IgG Fc, was constructed by a three-piece ligation of the truncated HBe fragment, IgG Fc, and Hind III/Cla I-cut pRc/CMV vector. The expression vector HBeAg, which expresses a secretory HBeAg protein, was constructed by inserting the HBeAg gene into the HindIII/ClaI cut-pRc/CMV vector. The expression vector HBcAg, which expresses a cytosolic HBcAg protein, was constructed by inserting the HBcAg gene into the HindIII/ClaI cut-pRc/CMV vector. To construct the IgG Fc expression vector, the human IgG Fc cDNA fragment was linked with a mouse VH signal leader sequence by two PCR reactions. In the first PCR reaction, the IgG Fc cDNA was used as a template for the amplification with a pair of primers (5' primer (SEQ.ID. No. 15), 5'-GCAGCTCCCAGATGGGTCCTGTCCAAAACTCAC ACATGCCCACCGTGCCCAGCAC-3', corresponding to the polynucleotide sequence 785 to 815 of the heavy chain and a partial VH-leader sequence, and the 3'-primer P-C (SEQ. ID. No. 14)). The second PCR utilizing the product of the first PCR as a template was carried out with a pair of primers (5' primer, (SEQ. ID. No. 16) 5'-TTAAGCTT CATATGGGAACATCTGTGGTTCTTCCTTCTCCTGG TGGCAG CTCCCAGATGGGTCCTGTCC-3', corresponding to the N-terminal polynucleotide sequence of the VH-leader sequence with additional HindIII and NdeI sites, and the 3' primer P-C (SEQ. ID. No. 14)). The Fc cDNA with a leader sequence was cloned into the HindIII/ClaI cut-pRc/CMV vector. These resultant vectors were identified by restriction enzyme analysis and confirmed by DNA sequencing. Plasmids were transformed into *E. coli* strain (XL-1 blue) and grown from a single colony for 16–20 hours at 37° C. in the presence of 50 ug/ml ampicillin. DNA was isolated using the Endotoxin-free purification kit (Qiagen) according to standard protocol. DNA was resuspended in endotoxin-free PBS (Sigma) at a final concentration of 1 mg/ml. The ratio of OD260/280 ranged from 1.8 to 2.0. DNA was stored –200° C. and analyzed by restriction digestion before the day of immunization.

The Fc fragment derived from a human IgG1a was used as a cell-binding element to enhance the internalization of the model HBV nucleocapsid protein, since DCs express IgG Fc receptors (FcγRs), which mediate a privileged antigen internalization route for efficient MHC-II as well as I-restricted antigen presentation. Although both HBcAg and HBeAg are encoded by the HBV pre-C/C gene, the secretory HBeAg protein is initiated at a start codon 29 residues upstream of the start codon for HbcAg. The HBeAg was fused in frame with a human IgG1a Fc fragment cDNA gene, and then cloned into the pRc/CMV. The human IgG Fc fragment can efficiently bind to the Fc receptors on mouse APCs. Control vectors containing the HBeAg gene (secretory), Fc fragment gene with a secretion signal leader sequence (secretory), or HBcAg gene (cytosolic) were constructed (FIG. 18). Murine marrow-derived DCs were generated. In brief, bone marrow stem cells were cultured in RPMI-1640 supplemented with 6% of FBS, 60 ng mGM-CSF/ml, and 100 U mIL-4/ml for 4 days. DCs were then cultured in medium containing a mixture of the recombinant HBeAg (100 µg/ml) and HBcAg (100 µg/ml) proteins (American Research Products, Boston, Mass.) for an additional 4 days. Pulsed-DCs (PDCs) were washed twice with 1×PBS at 1000 rpm for 5 min and resuspended in RPMI 1640 for further analysis. By using radiolabeling and immunoprecipitation/SDS-polyacrylamide gel analyses (PAGE), it was found that the HBeAg-Fc proteins (HBe-Fc)

were efficiently produced and secreted from transfected cells (FIG. 19A). Both intracellular and secreted HBe-Fc were directly precipitated by Protein A beads, indicating that the fusion protein retains its binding ability to Protein A.

EXAMPLE 16

Induction of $T_H1$, Helper T-Cells by HBe-Fc DNA Vaccine in vivo

Mice were immunized to evaluate this strategy in vivo. C57BL/6 or BALB/c mice were divided into four groups and each mouse was immunized with one i.m. injection of 100 ug (25–50 μg(μl) per quadricep) HBcAg, HBeAg, Fc, or HBe-Fc DNA. After 2–4 weeks of immunization, the mice were sacrificed and peripheral blood, spleens, and other tissue samples were collected.

First, splenocytes from the mice 2–4 weeks after immunization with DNA vaccines were re-stimulated with the recombinant HBe/cAg proteins for 5 days. T-cells were isolated from restimulated splenocytes, and then assessed by using the $^3$H-thymidine incorporation assay. As shown in FIG. 20, T cells from the mice immunized with HBe-Fc DNA construct or with HBe-Fc DNA vaccine primed T cells actively proliferated. In contrast, the T cells from the mice immunized with HBeAg, HBcAg, or Fc DNA vaccine or HBeAg, HBcAg and Fc DNA vaccine primed T cells did not actively proliferate.

CD4+ T-cells from the immunized mice were co-cultured with DCs that were pulsed with recombinant HBeAg and HBcAg, similar to Example 5. During 6 days of co-culture with different ratios of T-cells vs DCs, CD4+ T-cells from the mice immunized with HBeAg, HBcAg or Fc construct did not actively proliferate, and only low levels of IL-2 and IFN-γ were detected in the co-culture media (FIG. 21A and FIG. 21B). In contrast, in the co-cultures with the CD4+ T-cells from the mice immunized with HBe-Fc construct, CD4+ T-cells actively proliferated after only 48-hour co-culture even at a 1:1000 (DC:T-cells) ratio. Further, levels of IL-2 and IFN-γ in the co-culture media were significantly higher than those in the co-cultures with the CD4+ T-cells from the mice administered with HBeAg or HBcAg construct (FIG. 21A and FIG. 21B). Anti-CD4, but not anti-CD8 antibodies, dramatically blocked the production of these cytokines by the co-cultured cells (FIG. 21C and FIG. 21D). In addition, an irrelevant antigen, the recombinant HBsAg protein (American Research Product, Boston, Mass.), was used to pulse DCs in parallel with HBe/cAg. The HBsAg-pulsed DCs were unable to stimulate the CD4+ T-cells of HBe-Fc construct immunized mice in the described assay, demonstrating the specificity of CD4+ T helper 1 cell responses induced by HBe-Fc construct immunization. These results indicate that the HBe-Fc construct can more efficiently activate $T_H1$ than can the HBeAg or HBcAg constructs. Significant levels of IL-4 were not detected in any of the experiments. Since IL-2 and IFN-γ are mainly produced by $T_H1$ cells. The results indicate that HBe-Fc construct induces $T_H1$ response.

EXAMPLE 17

Induction of CTLs in vivo

To determine whether immunization with HBe-Fc construct can induce CTL responses, a JAM test was performed, similar to Example 11. Splenocytes from different immunized mice were restimulated in vitro for 4–6 days in medium containing synthetic peptide HBcAg13–27 and then co-cultivated with $^3$H-labeled, peptide (HBcAg13–27)-pulsed target cells EL-4 (H-2$^b$) and p815 (H-2$^d$) at varied effector/target ratios to measure target cell killing. As shown in FIG. 22, splenocytes from mice immunized with HBe-Fc construct demonstrated significantly higher target cell killing than those from mice immunized with HBeAg or HBcAg. The specificity of the killing was demonstrated by the inability of the splenocytes to kill HBcAg-pulsed p815 target cells with an H-2$^d$ background, and the inhibition of the killing by the anti-CD8, but not anti-CD4 antibody. Furthermore, HBsAg was also used to restimulate splenocytes from HBe-Fc construct immunized mice, and no significant killing to HBcAg-pulsed target cells was observed by the HBsAg-restimulated splenocytes. The superior cytotoxicity response induced by HBe-Fc construct is due to the enhanced T-helper 1 and the direct MHC class-I presentation of internalized HBe-Fc fusion protein by DCs.

EXAMPLE 18

Induction of Antibody

To determine whether HBe-Fc-DC immunization can induce antibody responses, anti-HBe/cAg antibody titers were measured in the pooled sera of mice immunized with different vectors, similar to Example 6. As shown in FIG. 23, anti-HBe/cAg antibodies were detected in the sera of mice immunization with HBe-Fc construct. The specificity of the antibody responses was demonstrated by the lack of antibody against HBsAg in the immunized mice. By contrast, significantly lower antibody titers were detected in mice immunized with HBeAg or HBcAg construct (FIG. 23). Taken together, HBe-Fc DNA is significantly superior to DNAs expressing native HBeAg or HBcAg in inducing CD4+ T helper 1 and CD8+ cytotoxic T-cell, as well as B-cell responses.

EXAMPLE 19

Systemic Activation of DCs by HBe-Fc DNA Vaccination

To evaluate the possibility of the HBe-Fc or HBeAg proteins being secreted from the transduced cells and circulating throughout the body to perform antigen presentation, a DC transfer experiment was performed. DCs were isolated from immunized mice and transferred into naive mice to assess whether the transferred DCs can prime naive CD4+ and CD8+ T-cells. Mice immunized with the HBeAg-Fc, PEA-HBe, or control DNA vaccine were sacrificed one month later. Mouse CD11c (N418) MicroBeads (Miltenyi Biotec) were used to isolate DCs from mouse spleens. CD11c+ DCs were injected (IP or IV) into naive mice (about 1–5×10$^5$/mouse). Two to four weeks after the DC transfer, the mice were sacrificed and the antigen-specific CD4+ and CD8+ T-cell responses of different mice are monitored. As shown in FIG. 24, DCs from splenocytes of HBe-Fc immunized mice efficiently activate naive T-cell responses, while DCs from splenocytes of HBe or HBc immunized mice failed to activate T-cell in naive mice. This result, together with results of the PCR and internalization assays, indicate that DC antigen presentation is enhanced by FcγR-mediated antigen endocytosis.

EXAMPLE 20

Secretion of Altered Membrane and Intracellular Proteins

Membrane proteins and intracellular proteins, which contain a sequence to prevent protein membrane translocation and secretion or lack a signal sequence for secretion, can be used for the strategy of the present invention without further modification. It is envisioned that deletion or mutation of the sequence which blocks a protein from secretion results in protein secretion. Membrane proteins often contain a high proportion of hydrophobic amino acids, thus altering the hydrophobicity of these proteins allows them to be targeted for secretion. One skilled in the art recognizes that the retrogen strategy also can be used to enhance immunogenicity of these proteins. Two examples for the deletion or mutation of membrane proteins are HPV E7 and EBV proteins.

E7 is a cytosolic protein. The presence of a string of charged residues hamper the secretion of the protein. Elimination of these residues facilitate the protein secretion and stabilize the protein (FIG. 17). Accordingly, the string of charged residues of HPV 16 E7 proteins was deleted in current construct (solid box) by two PCR reactions. As a result, secretion of the truncated E7 proteins after linking with a leader signal (IL-2) was dramatically enhanced.

EBV nuclear antigen 1 is a nuclear protein, which contains a stretch of hydrophobic amino acid residues which would interfere with protein membrane translocation and secretion. In a study, the stretch of hydrophobic amino acid residues in the EBNA1 protein was deleted. As a result, the truncated EBNA1 protein was efficiently secreted from cells after linking with a leader signal sequence.

In addition to deletion or truncation of the sequence, one skilled in the art recognizes that the sequence can also be mutated to reduce the hydrophobicity of the protein. Site-directed mutagenesis provides for the preparation and testing of sequence variants by introducing one or more polynucleotide sequence changes into a selected DNA.

In general, one first obtains a single-stranded vector, or melts two strands of a double-stranded vector, which includes within its sequence a DNA sequence encoding the desired protein or genetic element. An oligonucleotide primer bearing the desired mutated sequence, synthetically prepared, is then annealed with the single-stranded DNA preparation, taking into account the degree of mismatch when selecting hybridization conditions. The hybridized product is subjected to DNA polymerizing enzymes such as *E. coli* polymerase I (Klenow fragment) in order to complete the synthesis of the mutation-bearing strand. Thus, a heteroduplex is formed, wherein one strand encodes the original non-mutated sequence, and the second strand bears the desired mutation. This heteroduplex vector is then used to transform appropriate host cells, such as *E. coli* cells, and clones are selected that include recombinant vectors bearing the mutated sequence arrangement.

Site-directed mutagenesis is disclosed in U.S. Pat. Nos. 5,220,007; 5,284,760; 5,354,670; 5,366,878; 5,389,514; 5,635,377; and 5,789,166.

In addition to membrane proteins, intracellular proteins are modified, resulting in secretion. One such modification is merely the addition of a signal leader sequence. For example, MAGE is an intracellular protein that lacks a signal sequence for secretion. In Example 7, a signal sequence was added to MAGE by using PCR techniques. The addition of the signal sequence to MAGE enabled this intracellular protein to be secreted. Another modification of an intracellular protein is to alter the precursor, which is typically an intracellular protein, so that it is secreted similar to the mature protein. For example, the IL-1 beta precursor protein is cytosolic, but the mature protein is secreted. Thus, Siders and Mizel (J. Biol. Chem., 1995) truncated amino acid residues in the precursor protein. They illustrated that deletion of a few amino acids between 100 and 104 increased the secretion level of the truncated protein to the level of the mature IL-1 betas. Thus, one skilled in the art would be able to utilize this information to alter other intracellular proteins.

A further modification includes the use of viral particles, which are released from cells. Thus, the retrogen is fused to a viral gene and assembled into viral particles for release. A virus particle consists of a nucleic acid genome surrounded by a shell of protein. Packing of viral particles is performed by any of the methods well-known in the art.

EXAMPLE 21

Protein Glycosylation

Glycosylation of IgG-$F_c$ is known in the art to be essential for optimal activation of effector cells via $F_c\gamma R$ recognition. Thus, recombinant fusion proteins containing the Fc moiety must be generated in a system capable of gycoslylation if binding to Fc$\gamma$R is essential for its potential utility. The baculovirus-insect cell system is commonly used to generate high yield recombinant protein. The ability of this system to add a core oligosaccharide and outer arm sugar residues to glycoproteins is well known by the skilled artisan and makes it a suitable system for expression and purification of the HBe-Fc fusion protein.

The 1230 bp HBeFc fragment contained in the tHBeAgFc plasmid, which expresses the secretory HBe-Fc protein consisting of the truncated HBeAg in-frame fused to the IgG Fc, was constructed. Briefly, recombinant HBe-Fc baculovirus was generated using the pFastBac system (Gibco BRL) with the pFB 1 donor plasmid . The HBe-Fc fragment was first PCR amplified from tHBeAgFc template using the 5' primer (SEQ. ID. No. 17) 5'-GATCGAATTCATGCAA CTTTTTCACCTCTGC-3' and the 3' primer (SEQ. ID. NO. 18) 5'-GATCAAGCTTTCATTTACCCGGAGACAGGGA-3' to introduce EcoRI and HindIII restriction sites to the 5' and 3' ends, respectively. This PCR product was gel purified, digested, and ligated into EcoRI/HindIII cut pFB1 donor plasmid. The resultant vector (pFB1-HBeFc) was identified by restriction enzyme analysis and confirmed by DNA sequencing. Site-specific transposition of the HBe-Fc expression cassette from the donor plasmid into the baculovirus genome was performed by transforming DH10Bac *E. coli* with the pFB1-HBeFc donor plasmid. Recombinant baculovirus were identified by X-gal selection, as transposition into the bacmid disrupts expression of the lacZ$\alpha$ peptide. Recombinant bacmid DNA was isolated by miniprep and used to transfect Sf9 insect cells according to the manufacturers' instructions.

The viral stock obtained from the initial transfection was amplified by infecting a 50 ml suspension culture of Sf9 cells at $2\times10^6$ cells/ml with 0.5 ml of the viral stock, and collecting the supernatant after 48 hours. This stock was then subjected to two additional rounds of amplification at which point >90% of cells were producing recombinant HBe-Fc as monitored by immunofluorescent staining of infected cells. The amplified stock was then used to infect four 100 ml cultures of Sf9 cells for 72–90 hours. Supernatants were harvested and clarified by centrifugation for 20 minutes at 14,000 RPM, 4° C. The clarified supernatant was then passed twice over a 5 ml Detergent Absorber Gel Column (Boehringer Mannheim) to remove pluronic that could interfere with protein recovery, Recombinant HBe-Fc protein was then purified from the supernatant by passage over a protein G column (Pharmacia) at a flow rate of 1 ml/minute. The column was washed sequentially with 10 volumes of 100 mM Tris pH 6.0 and 10 mM Tris pH 6.0, and the protein eluted in 1 ml fractions with 10 volumes of 100 mM Glycine pH 2.7. The pH of all fractions was immediately adjusted to neutral by addition of 1/10 volume 1M Tris pH 8.0. Protein containing fractions were determined by $A_{280}$ and separated by 12% SDS-PAGE to determine purity. Purified fractions were then subjected to Western Blot. Briefly, 15 μg of the major protein containing eluted fraction was separated by 12% SDS-PAGE under reducing (R) or non-reducing (NR) conditions, transferred to nitrocellulose, blotted, and developed using ECL Western blotting detection reagents. Primary antibody, rabbit anti-HBc; secondary antibody, mouse anti-rabbit-peroxidase conjugate.

EXAMPLE 22

Identifications of MHC-II-Restricted Antigens

The present invention is used to identify MHC-II-restricted viral antigens, HIV, HCV, EBV, bacterial antigens, other pathogen antigens, tumor antigens, and self antigens related to autoimmune diseases. The expression vector in the present invention has been modified to include "test" polynucleotides. The polynucleotide sequences that are not known to elicit an immune response. This strategy of the present invention identifies new antigens/epitopes that are used to develop new vaccines.

First, a cDNA library is constructed using mRNA from selected cells, i.e., tumor cells. When cDNA is prepared from cells or tissue that express the polynucleotide sequences of interest at extremely high levels, the majority of cDNA clones that contain the polynucleotide sequence, which can be selected with minimal effort. For less abundantly transcribed polynucleotide sequences, various methods can be used to enrich for particular mRNAs before making the library. Retroviruses are used as a vector for the library. Retroviral libraries provide the ideal way to deliver a high-complexity library into virtually any mitotically active cell type for expression cloning. Because the viral particles infect with high efficiency, they deliver a more complex library than transfection-based methods. One skilled in the art realizes that any vector can be used for the library. A cDNA library is constructed by using methods well known in the art. Briefly, tumor cell lines are established from tumor samples. CD4+ T-cells from the same mammal peripheral bloods are expanded by co-culture with the mammal tumor lysate-pulsed DCs derived from monocytes/macrophages. These tumor cells that are recognized by expanded autologous CD4+ T-cells are identified. Next, the cell lines are plated in 96 wells. Expanded autologous CD4+ T-cells are added into the 96-wells, and the IFN-γ or GM-CSF concentrations in the 96-well co-cultures are monitored. The next step is to culture and extract mRNA from the positive tumor cells. The isolated mRNA is converted to cDNA and inserted into a vector, for example, lentiviral vector with a GFP marker or the test cDNAs are cloned into the expression vector of the present invention. The test cDNAs are cloned into the vector between the signal sequence and the cellular binding element as depicted, for example, in FIG. 25. Once the cDNA library is constructed, the viral vectors are transfected into packaging cells. Next, immature DCs derived from monocytes from the mammal with the same MHC-II genotype are transduced with the recombinant vectors and efficiency is determined. Transduced DCs are co-cultured with expanded autologous CD4+ T-cells. Positive clones are identified by ELISA (GM-CSF) or IL2 surface expression by flow cytometric array. The positive clone is PCR amplified and sequenced to determine the protein (FIG. 26).

The human genome is screened to identify the polynucleotide sequences that encode proteins and epitopes that are recognized by CD4+ T-cells. These polynucleotide products are used for cancer therapy or to induce immune tolerance for autoimmune disease therapy, or gene therapy. This basic screening procedure provides for the identification of epitopes for designing small therapeutic molecules.

Thus, a skilled artisan is cognizant that this screening procedure is modified to screen a variety of genomes, i.e., human, viral, bacterial, or parasitic. Construction of cDNA libraries are well known in the art. Thus, a skilled artisan is capable of utilizing this information to alter the present invention to identify antigens.

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

REFERENCES CITED

Abbas, A. K., Murphy, K. M. & Sher, A., *Nature* 383, 787–93 (1996).

Albert, M. L., Sauter, B. & Bhardwaj, N., *Nature* 392, 86–9 (1998).

Ausubel et al. (1997, *Current Protocols in Molecular Biology*, John Wiley & Sons, New York).

Banchereau, J. & Steinman, R. M., *Nature* 392, 245–52 (1998).

Bangham et al., *J. Mol. Biol.*, 13:238, 1965.

Bei R, Schlom J, Kashmiri S V S., *J Immunol Meth*; 186:245–255 (1995).

Bennett, S. R., Carbone, F. R., Karamalis, F., Miller, J. F. & Heath, W. R., *Journal of Experimental Medicine* 186, 65–70 (1997).

Bennett, S. R. et al., *Nature* 393, 478–80 (1998).

Bird et al., *Science* 242:423–426 (1988).

Bona, C. A., Casares, S. & Brumeanu, T. D., *Immunology Today* 19, 126–33 (1998).

Chaux, P. et al., *J. Experimental Medicine* 189, 767–78 (1999).

Chen, J. D., Bai, X., Yang, A. G., Cong, Y. & Chen, S. Y., *Nature Medicine* 3, 1110–6 (1997).

Cyster, J. G., Hartley, S. B. & Goodnow, C. C., *Nature* 371, 389–95 (1994).

Daeron, M., *Annual Review of Immunology* 15, 203–34 (1997).

De Veerman, M. et al., *Journal of Immunology* 162, 144–51 (1999).

Deamer and Uster, "*Liposome Preparation: Methods and Mechanisms*," LIPOSOMES, M. Ostro ed. (1983).

Ferrari, C. et al., *J. Immunol.* 145, 3442–9 (1990).

Gallagher, S., Winston, S. E., Fuller, S. A. & Hurrell, J. G. R. *Current Protocols in Immunology* (Supplement 26), Vol. 2 (ed. Coico, R.) 8.100.1–8.10.21 (John Wiley & Sons, Inc., 1998).

Gaugler, B. et al., *Journal of Experimental Medicine* 179, 921–30 (1994).

Gerhardt et al. (eds., 1994, *Methods for General and Molecular Bacteriology, American Society for Microbiology*, Washington, D.C.).

Ghosh and Bachhawat, In: Wu G. Wu C ed., Liver diseases, targeted diagnosis and therapy using specific receptors and ligands, New York: Marel Dekker, pp. 87–104, 1991.

Gilboa, E., *Immunity* 11, 263–70 (1999).

Greenberg, P. D., Cheever, M. A. & Fefer, A., *Journal of Experimental Medicine* 154, 952–63 (1981).

Gregoriadis, DRUG CARRIERS IN BIOLOGY AND MEDICINE, G. Gregoriadis (ed.), 1979, pp. 287–341.

Haeffier-Cavaillon, N., Klein, M. & Dorrington, K. J., *Journal of Immunology* 123, 1905–13 (1979).

Harlow et al., 1988, *Antibodies: A Laboratory Manual*, Cold Spring Harbor, N.Y.;

Houston et al., 1988, *Proc. Natl. Acad. Sci. USA* 85:5879–5883.

Hsu T A, Takahashi N, Tsukamoto Y, Kato K, Shimada I, Masuda K, Whiteley E M, Fan J Q, Lee Y C, Betenbaugh M J. *J Biol Chem* 1997; 272:9062–9070.

Hu, P. et al., *Human Antibodies & Hybridomas* 6, 57–67 (1995).

Huang, A. Y. et al., *Science* 264, 961–5 (1994).

Hung, K. et al., *Journal of Experimental Medicine* 188, 2357–68 (1998).

Inaba, K. et al., *Journal of Experimental Medicine* 176, 1693–702 (1992).

James, R. F., Edwards, S., Hui, K. M., Bassett, P. D. & Grosveld, F., *Immunology* 72, 213–8 (1991).

Jarvis D, Kawar Z, Hollister J., Curr Opin Biotechnol 1998; 9:528–533.

Kalams, S. A. & Walker, B. D., *Journal of Experimental Medicine* 188, 2199–204 (1998).

Kaneda et al., *Science*, 243:375–378, 1989.

Kato et al., *J. Biol. Chem.*, 266:3361–3364, 1991.

Kovacsoics-Bankowski, M. & Rock, K. L., *Science* 267, 243–6 (1995).

Lund J, Takahashi N, Pound J D, Goodall M, Jefferis R., *J Immunol* 1996; 157:4963–4969.

Lund J, Takahashi N, Pound J D, Goodall M, Nakagawa H, Jefferis R., *FASEB J* 1995; 9:115–119.

Mackey, M. F. et al., *Cancer Research* 57, 2569–74 (1997).

Manici, S. et al., *Journal of Experimental Medicine* 189, 871–6 (1999).

Matzinger, P., *Journal of Immunological Methods* 145, 185–92 (199 1).

Mellman, I., Turley, S. J. & Steinman, R. M., *Trends in Cell Biology* 8, 231–7 (1998).

Mumberg, D. et al., *Proceedings of the National Academy of Sciences of the United States of America* 96, 8633–8 (1999).

Nestle, F. O. et al., *Nature Medicine* 4, 328–32 (1998).

Nicolau et al., *Methods Enzymol.*, 149:157–176, 1987.

Nuchtem, J. G., Biddison, W. E. & Klausner, R. D., *Nature* 343, 74–6 (1990).

Ossendorp, F., Mengede, E., Camps, M., Filius, R. & Melief, C. J., *Journal of Experimental Medicine* 187, 693–702 (1998).

Ou, J. H., Laub, O. & Rutter, W. J., *Proc. Natl Acad. Sci. USA* 83, 1578–82 (1986).

Pardoll, D. M. & Topalian, S. L., *Current Opinion in Immunology* 10, 588–94 (1998).

Ravetch et al., 1993, *Ann. Rev. Immunol.* 9:457–492)

Regnault, A. et al., *Journal of Experimental Medicine* 189, 371–80 (1999).

Reynolds, S. R. et al., *International Journal of Cancer* 72, 972–6 (1997).

Ridge, J. P., Di Rosa, F. & Matzinger, P., *Nature* 393, 474–8 (1998).

Rosenberg, S. A., *Immunity* 10, 281–7 (1999).

Rosenfeld et al., *Clin. Res.*, 39(2), 311A (1991a);

Sambrook et al. (1989, *Molecular Cloning: A Laboratory Manual*, Cold Spring Harbor Laboratory, N.Y.).

Sanderson, S., Frauwirth, K. & Shastri, N., *Proceedings of the National Academy of Sciences of the United States of America* 92, 7217–21 (1995).

Schoenberger, S. P., Toes, R. E., van der Voort, E. I., Offringa, R. & Melief, C. J., *Nature* 393, 480–3 (1998).

Serre, K. et al., *J. Immunology* 161, 6059–67 (1998).

Sigal, L. J., Crotty, S., Andino, R. & Rock, K. L., *Nature* 398, 77–80 (1999).

Steinman, R. M. & Cohn, Z. A., *J. of Cell Biology* 55, 186–204 (1972).

Steiman, R. M. & Swanson, J., *J of Experimental Medicine* 182, 283–8 (1995).

Syrengelas, A. D. & Levy, R., *J. of Immunology* 162, 4790–5 (1999).

Szoka and Papahadjopoulos, *Proc. Nat'l Acad. Sci. U.S.A.* 75:4194–98 (1978).

Tanaka, F. et al., *Cancer Research* 57, 4465–8 (1997).

Tiollais, P., Pourcel, C. & Dejean, A., *Nature* 31 489–95 (1985).

Valmori, D. et al., *Journal of Experimental Medicine* 189, 895–906 (1999).

van der Bruggen, P. et al., *European Journal of Immunology* 24, 3038–43 (1994).

Van den Eynde, B. J. & van der Bruggen, P., *Current Opinion in Immunology* 9, 684–93 (1997).

Vijayasaradhi, S., Xu, Y., Bouchard, B. & Houghton, A. N, *Journal of Cell Biology* 130, 807–20 (1995).

Watts, C., *Annual Review of Immunology* 15, 821–50 (1997).

Weber, J. S. et al. , *Journal of Immunotherapy* 22, 431–40 (1999).

Wong et al., *Gene*, 10:87–94, 1980.

Wu, T. C. et al. *Proceedings of the National Academy of Sciences of the United States of America* 92, 11671–5 (1995).

Yang, A. G., Bai, X., Huang, X. F., Yao, C. & Chen, S., *Proceedings of the National Academy of Sciences of the United States of America* 94, 11567–72 (1997).

Zajac et al., *Curr. Opin. Immunol.* 10:444 (1998).

One skilled in the art readily appreciates that the present invention is well adapted to carry out the objectives and obtain the ends and advantages mentioned as well as those inherent therein. Vaccines, vectors, methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

We claim:

1. An expression vector comprising a polynucleotide promoter sequence, a polynucleotide encoding a signal sequence, a polynucleotide encoding an antigen, a polynucleotide encoding a cell binding element, and a polynucleotide polyadenylation sequence all operatively linked.

2. The expression vector of claim 1, wherein said polynucleotide promoter sequence is selected from the group consisting of a constitutive promoter, an inducible promoter and a tissue specific promoter.

3. The expression vector of claim 2, wherein said constitutive promoter is selected from the group consisting of a simian virus 40 (SV40) early promoter, a mouse mammary tumor virus promoter, a human immunodeficiency virus long terminal repeat promoter, a Moloney virus promoter, an avian leukemia virus promoter, an Epstein-Barr virus immediate early promoter, a Rous sarcoma virus promoter, a human action promoter, a human myosin promoter, a human hemoglobin promoter, cytomegalovirus (CMV) promoter and a human muscle creatine promoter.

4. The expression vector of claim 2, wherein said inducible promoter is selected from the group consisting of a metallothionine promoter, a glucocorticoid promoter, a progesterone promoter, and a tetracycline promoter.

5. The expression vector of claim 2, wherein said tissue specific promoter is selected from the group consisting of HER-2 promoter and a PSA associated promoter.

6. The expression vector of claim 1, wherein said polynucleotide encoding a signal sequence is selected from the group consisting of a hepatitis B virus E antigen signal sequence, an immunoglobulin heavy chain leader sequence, and a cytokine leader sequence.

7. The expression vector of claim 1, wherein said polynucleotide encoding an antigen comprises a polynucleotide sequence for at least one epitope, wherein said at least one epitope induces a B cell response in a mammal.

8. The expression vector of claim 1, wherein said polynucleotide encoding an antigen comprises a polynucleotide sequence for at least one epitope, wherein said at least one epitope induces a CD4+ T-cell response in a mammal.

9. The expression vector of claim 1, wherein said polynucleotide encoding an antigen comprises a polynucleotide sequence for at least one epitope, wherein said at least one epitope induces a CD8+ T-cell response in a mammal.

10. The expression vector of claim 1, wherein said polynucleotide encoding an antigen comprises a polynucleotide sequence for at least one epitope, wherein said at least one epitope induces a B cell response, a CD4+ T-cell response, and a CD8+ T-cell response in a mammal into which said antigen is introduced.

11. The expression vector of claim 1, wherein said polynucleotide encoding an antigen comprises a polynucleotide sequence for a plurality of epitopes, wherein said plurality of epitopes induces a B cell response, a CD4+ T-cell response, and a CD8+ T-cell response in a mammal into which said antigen is introduced.

12. The expression vector of claim 1, wherein said polynucleotide encoding an antigen is a polynucleotide sequence selected from at least one polynucleotide sequence associated with a disease, wherein said disease is selected from the group consisting of infectious disease, cancer and autoimmune disease.

13. The expression vector of claim 12, wherein said polynucleotide encoding an antigen is a polynucleotide sequence selected from at least one polynucleotide sequence from an infectious disease, wherein said infectious disease is caused by a pathogenic microorganism selected from the group consisting of virus, bacterium, fungus and protozoan.

14. The expression vector of claim 13, where said polynucleotide encoding an antigen is a polynucleotide sequence selected from at least one polynucleotide sequence from a viral gene, wherein said viral gene is selected from the group consisting of hepatitis B virus, hepatitis C virus, human immunodeficiency virus, papillomavirus, and herpesvirus.

15. The expression vector of claim 14, wherein said hepatitis B virus is hepatitis B virus e antigen or the hepatitis B virus core antigen.

16. The expression vector of claim 14, wherein said human immunodeficiency virus is gp160 or gp120.

17. The expression vector of claim 14, wherein said papillomavirus is the papillomavirus E7 or papillomavirus E6.

18. The expression vector of claim 14, wherein said herpesvirus is selected from the group consisting of herpes simplex virus type 1, herpes simplex virus type 2, Epstein-Barr virus, cytomegalovirus, human herpes virus 6, human herpes virus 7 and human herpes virus 8.

19. The expression vector of claim 12, wherein the disease is selected from the roup consisting of breast cancer, cervical cancer, melanoma, renal cancer and rostate cancer.

20. The expression vector of claim 1, wherein said polynucleotide encoding a sequence for an antigen is a polynucleotide sequence selected from the group consisting of polynucleotide sequences encoding tyrosinase, MART, trp, MAGE-1, MAGE-2, MAGE-3, gp 100, HER-2, Ras and PSA.

21. The expression vector of claim 12, wherein the disease is selected from the group consisting of rheumatoid arthritis, systemic lupus erythematosus, multiple sclerosis, psoriasis and Crohn's disease.

22. The expression vector of claim 1, wherein said polynucleotide encoding an antigen encodes a Fc antibody fragment or an interleukin.

23. The expression vector of claim 22, wherein the polynucleotide sequence encodes interleukin 5.

24. The expression vector of claim 1, wherein said polynucleotide encoding a cell binding element is a polynucleotide sequence of a ligand which binds to a cell surface receptor.

25. The expression vector of claim 24, wherein said polynucleotide sequence of a ligand is selected from the group consisting of polynucleotide sequences which encode a Fc fragment, a toxin cell binding domain, a cytokine, a small peptide and an antibody.

26. The expression vector of claim 25, wherein said polynucleotide sequence encodes a pseudomonas exotoxin cell binding domain.

27. The expression vector of claim 25, wherein said polynucleotide sequence encodes interleukin 5 or interleukin 6.

28. The expression vector of claim 1, wherein said polynucleotide encoding a cell binding element is a homologous polynucleotide sequence or a heterologous polynucleotide sequence.

29. The expression vector of claim 28, wherein said polynucleotide encoding a cell binding element is a homologous Fc fragment.

30. The expression vector of claim 28, wherein said polynucleotide encoding a cell binding element is a heterologous Fc Fragment.

31. The expression vector of claim 1, wherein said expression vector further comprises an integration signal sequence which facilitates integration of said expression vector into the genome of the cell.

32. The expression vector of claim 31, wherein the integration signal sequence is a viral long terminal repeat sequence or an adeno-associated virus ITR sequence.

33. The expression vector of claim 1, wherein the vector is selected from the group consisting of viral vector, bacterial vector and mammalian vector.

34. A transformed cell comprising an expression vector, wherein said expression vector comprises a polynucleotide promoter sequence, a polynucleotide encoding a signal sequence, a polynucleotide encoding an antigen, a polynucleotide encoding a cell binding element, and a polynucleotide polyadenylation sequence all operatively linked.

35. The cell of claim 34, wherein said cell is prokaryotic or eukaryotic.

36. The cell of claim 35, wherein said eukaryotic cell is selected from the roup of eukaryotic cells consisting of yeast, insects, and mammals.

37. A fusion protein comprising a signal sequence, an antigen and a cell binding element.

38. A vaccine comprising an expression vector, wherein said expression vector comprises a polynucleotide encoding a promoter sequence, a polynucleotide encoding a secretion signal sequence, a polynucleotide encoding an antigen, a polynucleotide encoding a cell binding element, and a polynucleotide encoding a polyadenylation sequence, wherein said sequences are operatively linked.

39. A vaccine comprising antigen presenting cells, wherein said antigen presenting cells are transduced in vitro with the fusion protein of claim 37.

40. A vaccine comprising antigen presenting cells, wherein said antigen presenting cells are transduced in vitro with the expression vector of claim 1.

41. A vaccine comprising the fusion protein of claim 37.

42. An expression vector comprising at least a polynucleotide encoding a signal sequence, a polynucleotide encoding an antigen and a polynucleotide encoding a cell binding element.

43. A method to elicit an immune response directed against an antigen, comprising the steps of:
   introducing an expression vector into a cell, wherein said expression vector comprises a polynucleotide promoter sequence, a polynucleotide encoding a signal sequence, a polynucleotide encoding said antigen, a polynucleotide encoding a cell binding element, and a polynucleotide polyadenylation sequence, all operatively linked; and
   expressing said vector to produce said antigen under conditions, wherein said antigen is secreted from the cell; said secreted antigen is endocytosed into the cell; said endocytosed antigen is processed inside the cell; and said processed antigen is presented to a cell surface protein, to elicit a T-cell mediated immune response.

44. The method of claim 43 wherein the processed antigen is presented to a cell surface protein selected from the group consisting of MHC-I, MHC-II or B-cells receptors.

45. The method of claim 43 wherein the antigen is secreted by a first cell and internalized by a second cell.

46. The method of claim 45 wherein the first cell and second cell are antigen presenting cells.

47. The method of claim 45 wherein the first cell is a non-antigen presenting cell and the second cell is an antigen presenting cell.

48. The method of claim 47 wherein the first cell is a muscle cell.

49. A method to elicit an immune response directed against an antigen comprising the step of administering the expression vector of claim 1 directly to a mammal via a parenteral route.

50. The method of claim 43, wherein said polynucleotide promoter sequence is selected from the group consisting of a constitutive promoter, an inducible promoter and a tissue specific promoter.

51. The method of claim 50, wherein said constitutive promoter is selected from the group consisting of a simian virus 40 (SV40) early promoter, a mouse mammary tumor virus promoter, a human immunodeficiency virus long terminal repeat promoter, a Moloney virus promoter, an avian leukemia virus promoter, an Epstein-Barr virus immediate early promoter, a Rous sarcoma virus promoter, a human action promoter, a human myosin promoter, a human hemoglobin promoter, cytomegalovirus (CMV) promoter and a human muscle creatine promoter.

52. The method of claim 50, wherein said inducible promoter is selected from the group consisting of a metallothionine promoter, a glucocorticoid promoter, a progesterone promoter, and a tetracycline promoter.

53. The method of claim 50, wherein said tissue specific promoter is selected from the group consisting of HER-2 promoter and a PSA associated promoter.

54. The method of claim 43, wherein said polynucleotide encoding a signal sequence is selected from the group consisting of a hepatitis B virus e antigen signal sequence, an immunoglobulin heavy chain leader sequence, and a cytokine leader sequence.

55. The method of claim 43, wherein said polynucleotide encoding an antigen is a polynucleotide sequence selected from at least one polynucleotide sequence associated with a disease, wherein said disease is selected from the group consisting of infectious disease, cancer and autoimmune disease.

56. The method of claim 55, wherein said polynucleotide encoding an antigen is a polynucleotide sequence selected from at least one polynucleotide sequence from an infectious disease, wherein said infectious disease is caused by a pathogenic microorganism selected from the group consisting of virus, bacterium, fungus and protozoan.

57. The method of claim 56, where said polynucleotide encoding an antigen is a polynucleotide sequence selected from at least one polynucleotide sequence from a viral gene, wherein said viral gene is selected from the group consisting of hepatitis B virus, hepatitis C virus, human immunodeficiency virus, papillomavirus, and herpesvirus.

58. The method of claim 57, wherein said hepatitis B virus is hepatitis B virus e antigen or the hepatitis B virus core antigen.

59. The method of claim 57, wherein said human immunodeficiency virus is gp160 or gp120.

60. The method of claim 57, wherein said papillomavirus is the papillomavirus E7 or papillomavirus E6.

61. The method of claim 57, wherein said herpes virus is selected from the group consisting of herpes simplex virus type 1, herpes simplex virus type 2, Epstein-Barr virus, a cytomegalovirus, a human herpes virus 6, a human herpes virus 7 and a human herpes virus 8.

62. The method of claim 55, wherein the disease is selected from the group consisting of breast cancer, cervical cancer, melanoma, renal cancer and prostate cancer.

63. The method of claim 55, wherein the disease is selected from the group consisting of rheumatoid arthritis, systemic lupus erythematosus, multiple sclerosis, psoriasis and Crohn's disease.

64. The method of claim 43, wherein said polynucleotide encoding an antigen encodes an Fc antibody fragment or an interleulin.

65. The me of claim 64, wherein the polynucleotide sequence encodes interleukin 5.

66. The method of claim 43, wherein said polynucleotide encoding a cell binding element is a polynucleotide sequence of a ligand which binds to a cell surface receptor.

67. The method of claim 66, wherein said polynucleotide sequence of a ligand is selected from a group consisting of polynucleotide sequences which encodes a Fc fragment, a toxin cell binding domain, a cytokine, a small peptide and an antibody.

68. The method of claim 67, wherein said polynucleotide sequence encodes a pseudomonas exotoxin cell binding domain.

69. The method of claim 67, wherein said polynucleotide sequence encodes interleukin 5 or interleukin 6.

70. The method of claim 43, wherein said polynucleotide encoding a cell binding element is a homologous polynucleotide sequence or a heterologous polynucleotide sequence.

71. The method of claim 70, wherein said polynucleotide encoding a cell binding element is a homologous Fc fragment.

72. The method of claim 70, wherein said polynucleotide encoding a cell binding element is a heterologous Fc fragment.

73. The method of claim 43, wherein said expression vector further comprises an integration signal sequence which facilitates integration of said expression vector into the genome of the cell.

74. The method of claim 73, wherein integration signal sequence is a viral long terminal repeat sequence or an adeno-associated virus ITR sequence.

75. The method of claim 43, wherein the vector is selected from the group consisting of viral vector, bacterial vector and mammalian vector.

76. A method to identify a polynucleotide sequence which encodes at least one MHC-II restricted epitope that is capable of activating CD4+ helper T cells, said method comprising the steps of:
  introducing an expression vector into an antigen presenting cell to produce a transduced antigen presenting cell, wherein said expression vector comprises a polynucleotide promoter sequence, a polynucleotide encoding a signal sequence, a polynucleotide encoding a test polypeptide, a polynucleotide encoding a cell binding element, and a polynucleotide polyadenylation sequence, all operatively linked;
  contacting said transduced antigen presenting cell with naive T-cells or primed T-cells; and
  assessing whether any naive T-cells or primed T cells are activated upon contact with said transduced antigen presenting cell wherein activation of said T-cells indicates that the polynucleotide encoding the test polypeptide is a gene or fragment thereof capable of activating CD4+ helper T cells.

77. The method of claim 76, wherein the polynucleotide encoding a test polypeptide is a cDNA library isolated from tumor cell lines.

78. The method of claim 76, wherein the polynucleotide encoding a test polypeptide is selected from the group of cDNA libraries consisting of viral genomes, bacterial genomes, parasitic genomes, and human genomes.

79. A method to identify a polynucleotide sequence which encodes at least one MHC-II restricted epitope that is capable of eliciting an immune response in vivo, said method comprising the steps of:
  introducing an expression vector into antigen presenting cells to produce transduced antigen presenting cells, wherein said expression vector comprises a polynucleotide promoter sequence, a polynucleotide encoding a signal sequence, a polynucleotide encoding a test polypeptide, a polynucleotide encoding a cell binding element, and a polynucleotide polyadenylation sequence, all operatively linked;
  administering said transduced antigen presenting cells to a mammal via a parenteral route;
  collecting T-cells from splenocytes and co-culturing with dendritic cells; and
  assessing activation of T-cells wherein said activation of T-cells indicate that the polynucleotide encoding the test polypeptide is a polynucleotide sequence or fragment thereof capable of activating CD4+ helper T cells.

80. The method of claim 79, wherein the polynucleotide encoding a test polypeptide is a cDNA library isolated from tumor cell lines.

81. The method of claim 79, wherein the polynucleotide encoding a test polypeptide is selected from the group of cDNA libraries consisting of viral genomes, bacterial genomes, parasitic genomes, and human genomes.

82. A method to identify a polynucleotide sequence which encodes at least one MHC-II restricted epitope that is capable of eliciting an immune response in vivo, aid method comprising the steps of:
  administering to a mammal via a parenteral route an expression vector, wherein said expression vector comprises a polynucleotide promoter sequence, a polynucleotide encoding a signal sequence, a polynucleotide encoding a test polypeptide, a polynucleotide encoding a cell binding element, and a polynucleotide polyadenylation sequence, all operatively linked;
  collecting T-cells from splenocytes and co-culturing with dendritic cells; and
  assessing activation of T-cells wherein said activation of T-cells indicate that the polynucleotide encoding the test polypeptide is a polynucleotide sequence or fragment thereof capable of activating CD4+ helper T cells.

83. The method of claim 82, wherein the polynucleotide encoding a test polypeptide is a cDNA library isolated from tumor cell lines.

84. The method of claim 82, wherein the polynucleotide encoding a test polypeptide is selected from the group of cDNA libraries consisting of viral genomes, bacterial genomes, parasitic genomes, and human genomes.

85. A method of treating cancer comprising the steps of:
  identifying a test polypeptide which encodes at least one MHC-II restricted epitope, wherein said polypeptide is identified under the conditions of transducing antigen presenting cells with an expression vector comprising a polynucleotide promoter sequence, a polynucleotide encoding a signal sequence, a polynucleotide encoding a test polypeptide, a polynucleotide encoding a cell binding element, and a polynucleotide polyadenylation sequence, all operatively linked and assessing activation of T-cells wherein said activation of T-cells indicate that the polynucleotide encoding the test polypeptide is a gene or fragment thereof capable of activating CD4+ helper T cells; and
  administering antigen presenting cells to a mammal via a parenteral route, wherein said antigen presenting cells are transduced with the test polypeptide.

86. A method of treating cancer comprising the steps of:
  identifying a test polypeptide which encodes at least one MHC-II restricted epitope, wherein said polypeptide is identified under the conditions of transducing antigen presenting cells with an expression vector comprising a polynucleotide promoter sequence, a polynucleotide encoding a signal sequence, a polynucleotide encoding a test polypeptide, a polynucleotide encoding a cell binding element, and a polynucleotide polyadenylation sequence, all operatively linked and assessing activation of T-cells wherein said activation of T-cells indicate that the polynucleotide encoding the test polypeptide is a gene or fragment thereof capable of activating CD4+ helper T cells; and
  administering to a mammal via a parenteral route an expression vector, wherein said expression vector comprises at least the polynucleotide encoding the test polypeptide and a polynucleotide encoding a cell binding element.

87. A method of treating a viral infection comprising the steps of:
  identifying a test polypeptide which encodes at least one MHC-II restricted epitope, wherein said polypeptide is identified under the conditions of transducing antigen presenting cells with an expression vector comprising a polynucleotide promoter sequence, a polynucleotide encoding a signal sequence, a polynucleotide encoding a test polypeptide, a polynucleotide encoding a cell binding element, and a polynucleotide polyadenylation sequence, all operatively linked and assessing activation of T-cells wherein said activation of T-cells indicate that the polynucleotide encoding the test polypeptide is a gene or fragment thereof capable of activating CD4+ helper T cells; and
  administering antigen presenting cells to a mammal via a parenteral route, wherein said antigen presenting cells are transduced with the test polypeptide.

88. A method of treating a viral infection comprising the steps of:

identifying a test polypeptide which encodes at least one MHC-II restricted epitope, wherein said polypeptide is identified under the conditions of transducing antigen presenting cells with an expression vector comprising a polynucleotide promoter sequence, a polynucleotide encoding a signal sequence, a polynucleotide encoding a test polypeptide, a polynucleotide encoding a cell binding element, and a polynucleotide polyadenylation sequence, all operatively linked and assessing activation of T-cells wherein said activation of T-cells indicate that the polynucleotide encoding the test polypeptide is a gene or fragment thereof capable of activating CD4+ helper T cells; and administering to a mammal via a parenteral route an expression vector, wherein said expression vector comprises at least the polynucleotide encoding the test polypeptide and a polynucleotide encoding a cell binding element.

89. A method of treating an autoimmune disease comprising the steps of:

identifying a test polypeptide which encodes at least one MHC-II restricted epitope, wherein said polypeptide is identified under the conditions of transducing antigen presenting cells with an expression vector comprising a polynucleotide promoter sequence, a polynucleotide encoding a signal sequence, a polynucleotide encoding a test polypeptide, a polynucleotide encoding a cell binding element, and a polynucleotide polyadenylation sequence, all operatively linked and assessing activation of T-cells wherein said activation of T-cells indicate that the polynucleotide encoding the test polypeptide is a gene or fragment thereof capable of activating CD4+ helper T cells; and administering antigen presenting cells to a mammal via a parenteral route, wherein said antigen presenting cells are transduced with the test polypeptide.

90. A method of treating autoimmune disease comprising the steps of:

identifying a test polypeptide which encodes at least one MHC-II restricted epitope, wherein said polypeptide is identified under the conditions of transducing antigen presenting cells with an expression vector comprising a polynucleotide promoter sequence, a polynucleotide encoding a signal sequence, a polynucleotide encoding a test polypeptide, a polynucleotide encoding a cell binding element, and a polynucleotide polyadenylation sequence, all operatively linked and assessing activation of T-cells wherein said activation of T-cells indicate that the polynucleotide encoding the test polypeptide is a gene or fragment thereof capable of activating CD4+ helper T cells; and administering to a mammal via a parenteral route an expression vector, wherein said expression vector comprises at least the polynucleotide sequence encoding the test polypeptide and a polynucleotide encoding a cell binding element.

91. A method of producing a vaccine to immunize an mammal comprising the steps of:

transducing antigen presenting cells by introducing an expression vector into said antigen presenting cells to produce a transduced antigen presenting cell, wherein said expression vector comprises a polynucleotide promoter sequence, a polynucleotide encoding a signal sequence, a polynucleotide encoding an antigen, a polynucleotide encoding a cell binding element, and a polynucleotide polyadenylation sequence, all operatively linked; and expressing said vector to produce an antigen under conditions wherein said antigen is secreted from the cell.

92. A method of administering the vaccine of claim 41, wherein antigen presenting cells are transduced with the vaccine in vitro prior to administering to a mammal.

93. A method of administering the vaccine of claim 38, wherein the vaccine is administered parenterally.

94. A method of administering the vaccine of claim 41, wherein antigen presenting cells are transduced with the vaccine ex vivo prior to administering to a mammal.

95. A method of inducing an immune response comprising the steps of co-administering to a mammal a cytokine expression vector and a retrogen expression vector, wherein the retrogen expression vector comprises a polynucleotide promoter sequence, a polynucleotide encoding a signal sequence, a polynucleotide encoding an antigen, a polynucleotide encoding a cell binding element, and a polynucleotide polyadenylation sequence all operatively linked.

96. The method of claim 95, wherein the cytokine expression vector contains the sequence for GM-CSF.

97. The method of claim 95, wherein the cytokine expression vector contains the sequence for IL-2.

98. A method of inducing an immune response comprising the steps of administering to a mammal one expression vector, wherein said expression vector comprises a polynucleotide sequence encoding a cytokine protein and a polynucleotide sequence encoding a fusion protein under transcriptional control of one promoter, wherein said fusion protein comprises a signal sequence, an antigen and a cell binding element.

99. The method of claim 98, wherein the polynucleotide sequence encoding the cytokine protein and the polynucleotide sequence encoding the fusion protein are under separate transcriptional control, and wherein the polynucleotide sequence encoding the cytokine protein and the polynucleotide sequence encoding the fusion protein are in tandem in the one expression vector.

100. A method of inducing an immune response comprising the steps of co-administering to a mammal two different retrogen expression vectors, wherein a first retrogen expression vector comprises a polynucleotide promoter sequence, a polynucleotide encoding a signal sequence, a polynucleotide encoding a first antigen, a polynucleotide encoding a cell binding element, and a polynucleotide polyadenylation sequence all operatively linked; and a second retrogen expression vector comprises a polynucleotide promoter sequence, a polynucleotide encoding a signal sequence, a polynucleotide encoding a second antigen, a polynucleotide encoding a cell binding element, and a polynucleotide polyadenylation sequence all operatively linked.

101. A method of inducing an immune response comprising the steps of administering to a mammal one expression vector, wherein said expression vector comprises a polynucleotide sequence encoding a first fusion protein and a polynucleotide sequence encoding a second fusion protein under transcriptional control of one promoter, wherein said first fusion protein comprises a first signal sequence, a first antigen and a first cell binding element and said second fusion protein comprises a second signal sequence, a second antigen and a second cell binding element.

102. The method of claim 101, wherein said first and second signal sequences are the same signal sequence, first and second antigens are different antigens and said first and second cell binding elements are an Fc fragment.

103. The method of claim 101, wherein said first and second signal sequences are the same signal sequence, first and second antigens are different antigens and said first and second cell binding elements are the same cell binding element.

104. The method of claim 101, wherein said first and second signal sequences are different signal sequences, first and second antigens are different antigens and said first and second cell binding elements are the same cell binding element.

105. The method of claim 101, wherein said first and second signal sequences are the same signal sequence, first and second antigens are different antigens and said first and second cell binding elements are different cell binding elements.

106. The method of claim 101, wherein said first and second signal sequences are different signal sequences, first and second antigens are different antigens, and said first and second cell binding elements are different cell binding elements.

107. The method of claim 101, wherein the polynucleotide sequence encoding the first fusion protein and the polynucleotide sequence encoding the second fusion protein are under separate transcriptional control, and wherein the polynucleotide sequence encoding the first fusion protein and the polynucleotide sequence encoding the second fusion protein are in tandem in one expression vector.

108. A method of simultaneously inducing both CD4+ and CD8+ T-cells comprising the steps of administering a fusion protein, wherein the protein comprises both a MHC-I and MHC-II epitope fused to a cell binding element.

109. A method of producing a fusion protein comprising the steps of:
   transducing an antigen presenting cell by introducing an expression vector into said antigen presenting cell to produce a transduced antigen presenting cell, wherein said expression vector comprises a polynucleotide promoter sequence, a polynucleotide encoding a signal sequence, a polynucleotide encoding an antigen, a polynucleotide encoding a cell binding element, and a polynucleotide polyadenylation sequence, all operatively linked; and
   expressing said vector to produce a fusion protein under conditions, wherein said fusion protein is secreted from the cell.

110. A method of administering a fusion protein comprising administering antigen presenting cells transduced with the fusion protein in vitro prior to administering to a mammal.

111. A method of administering a fusion protein comprising administering the fusion protein parenterally to a mammal.

112. A method of secreting an intracellular protein comprising the steps of:
   introducing an expression vector into a cell, wherein said expression vector comprises a polynucleotide promoter sequence, a polynucleotide encoding a signal sequence, a polynucleotide encoding an intracellular protein, a polynucleotide encoding a cell binding element, and a polynucleotide polyadenylation sequence, all operatively linked; and
   expressing said vector to produce a fusion protein under conditions, wherein said fusion protein is secreted from the cell.

113. The method of claim 112, wherein a region of said polynucleotide encoding an intracellular protein is truncated to increase the efficiency of secretion.

114. The method of claim 112, wherein a region of said polynucleotide encoding an intracellular protein is mutated to increase the efficiency of secretion.

115. The method of claim 112, wherein said polynucleotide encoding an intracellular protein is HPV 16 E7.

116. A method of secreting a membrane protein comprising the steps of:
   introducing an expression vector into a cell, wherein said expression vector comprises a polynucleotide promoter sequence, a polynucleotide encoding a signal sequence, a polynucleotide encoding a membrane protein, a polynucleotide encoding a cell binding element, and a polynucleotide polyadenylation sequence, all operatively linked; and
   expressing said vector to produce a fusion protein under conditions, wherein said fusion protein is secreted from the cell.

117. The method of claim 116, wherein a region of said polynucleotide encoding a membrane protein is truncated to increase the efficiency of secretion.

118. The method of claim 116, wherein a region of said polynucleotide encoding a membrane protein is mutated to increase the efficiency of secretion.

119. The method of claim 116, wherein said polynucleotide encoding a membrane protein is EBV nuclear antigen 1.

* * * * *

SEQUENCE LISTING

<160> NUMBER OF SEQ ID NOS: 19

<210> SEQ ID NO 1
<211> LENGTH: 34
<212> TYPE: DNA
<213> ORGANISM: Homo sapiens

<400> SEQUENCE: 1
acgcgtcgac atgcctcttg agcagaggag tcag                          34

<210> SEQ ID NO 2
<211> LENGTH: 33
<212> TYPE: DNA
<213> ORGANISM: Homo sapiens

<400> SEQUENCE: 2
ccgctcgagt cactcttccc cctctctcaa aac                           33

<210> SEQ ID NO 3
<211> LENGTH: 103
<212> TYPE: DNA
<213> ORGANISM: Homo sapiens

<400> SEQUENCE: 3
acgcgtcgac atgaaggtct ccgcggcagc cctcgctgtc atcctcattg ctactgccct    60
ctgcgctcct gcatctgcca tgcctcttga gcagaggagt cag                    103

<210> SEQ ID NO 4
<211> LENGTH: 38
<212> TYPE: DNA
<213> ORGANISM: Homo sapiens

<400> SEQUENCE: 4
ataagaatgc ggccgctctc ttcccctct ctcaaaac                       38

<210> SEQ ID NO 5
<211> LENGTH: 31
<212> TYPE: DNA
<213> ORGANISM: Homo sapiens

<400> SEQUENCE: 5
ataagcggcc gctaaaactc acacatgccc a                             31

<210> SEQ ID NO 6
<211> LENGTH: 33
<212> TYPE: DNA
<213> ORGANISM: Homo sapiens

<400> SEQUENCE: 6
ccgctcgagt catttacccg gagacaggga gag                           33

<210> SEQ ID NO 7
<211> LENGTH: 55
<212> TYPE: DNA
<213> ORGANISM: Homo sapiens

<400> SEQUENCE: 7
gcagctccca gatgggtcct gtccaaaact cacacatgcc caccgtgccc agcac       55

<210> SEQ ID NO 8
<211> LENGTH: 68

```
<212> TYPE: DNA
<213> ORGANISM: Homo sapiens

<400> SEQUENCE: 8
acgcgtcgac atgggaacat ctgtggttct tccttctcct ggtggcagct cccagatggg    60
tcctgtcc                                                              68

<210> SEQ ID NO 9
<211> LENGTH: 35
<212> TYPE: DNA
<213> ORGANISM: Hepatitis B virus

<400> SEQUENCE: 9
ttaagcttat gcaactttt cacctctgcc taatc                                 35

<210> SEQ ID NO 10
<211> LENGTH: 34
<212> TYPE: DNA
<213> ORGANISM: Hepatitis B virus

<400> SEQUENCE: 10
tttctagaat cgattaacat tgagattccc gaga                                 34

<210> SEQ ID NO 11
<211> LENGTH: 37
<212> TYPE: DNA
<213> ORGANISM: Hepatitis B virus

<400> SEQUENCE: 11
gtgcggccgc tctaacaaca gtagtttccg gaagtgt                              37

<210> SEQ ID NO 12
<211> LENGTH: 40
<212> TYPE: DNA
<213> ORGANISM: Hepatitis B virus

<400> SEQUENCE: 12
ttaagcttat ggacattgac ccttataaag aatttggagc                           40

<210> SEQ ID NO 13
<211> LENGTH: 31
<212> TYPE: DNA
<213> ORGANISM: Homo sapiens

<400> SEQUENCE: 13
ataagcggcc gctaaaactc acacatgccc a                                    31

<210> SEQ ID NO 14
<211> LENGTH: 36
<212> TYPE: DNA
<213> ORGANISM: Homo sapiens

<400> SEQUENCE: 14
tattctagat cgatcactca tttacccgga gacagg                               36

<210> SEQ ID NO 15
<211> LENGTH: 55
<212> TYPE: DNA
<213> ORGANISM: Homo sapiens (first 30)/Murine (last 25)

<400> SEQUENCE: 15
gcagctccca gatgggtcct gtccaaaact cacacatgcc caccgtgccc agcac          55
```

```
<210> SEQ ID NO 16
<211> LENGTH: 69
<212> TYPE: DNA
<213> ORGANISM: Murine

<400> SEQUENCE: 16
ttaagcttca tatgggaaca tctgtggttc ttccttctcc tggtggcagc tcccagatgg      60
gtcctgtcc                                                             69

<210> SEQ ID NO 17
<211> LENGTH: 31
<212> TYPE: DNA
<213> ORGANISM: Hepatitis B virus

<400> SEQUENCE: 17
gatcgaattc atgcaactt ttcacctctg c                                     31

<210> SEQ ID NO 18
<211> LENGTH: 31
<212> TYPE: DNA
<213> ORGANISM: Homo sapiens

<400> SEQUENCE: 18
gatcaagctt tcatttaccc ggagacaggg a                                    31

<210> SEQ ID NO 19
<211> LENGTH: 98
<212> TYPE: PRT
<213> ORGANISM: Human papillomavirus type E7

<400> SEQUENCE: 19

Met His Gly Asp Thr Pro Thr Leu His Glu Tyr Met Leu Asp Leu Gln
  1               5                  10                  15

Pro Glu Thr Thr Asp Leu Tyr Cys Tyr Glu Gln Leu Ser Asp Ser Ser
                 20                  25                  30

Glu Glu Glu Asp Glu Ile Asp Gly Pro Ala Gly Gln Ala Glu Pro Asp
             35                  40                  45

Arg Ala His Tyr Asn Ile Val Thr Phe Cys Cys Lys Cys Asp Ser Thr
         50                  55                  60

Leu Arg Leu Cys Val Gln Ser Thr His Val Asp Ile Arg Thr Leu Glu
 65                  70                  75                  80

Asp Leu Leu Met Gly Thr Leu Gly Ile Val Cys Pro Ile Cys Ser Gln
                 85                  90                  95

Lys Pro
```